US008790619B2

(12) United States Patent
Wadsworth et al.

(10) Patent No.: US 8,790,619 B2
(45) Date of Patent: *Jul. 29, 2014

(54) INDOLE DERIVATIVES

(75) Inventors: Harry John Wadsworth, Amersham (GB); Bo Shan, Jiangsu (CN); Dennis O'Shea, Amersham (GB); Joanna Marie Passmore, Amersham (GB); William John Trigg, Amersham (GB); Amanda Ewan, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 137 days.

This patent is subject to a terminal disclaimer.

(21) Appl. No.: 13/258,465

(22) PCT Filed: Mar. 26, 2010

(86) PCT No.: PCT/EP2010/053998
§ 371 (c)(1),
(2), (4) Date: Sep. 22, 2011

(87) PCT Pub. No.: WO2010/109007
PCT Pub. Date: Sep. 30, 2010

(65) Prior Publication Data
US 2012/0020884 A1    Jan. 26, 2012

Related U.S. Application Data

(60) Provisional application No. 61/164,131, filed on Mar. 27, 2009.

(30) Foreign Application Priority Data

Mar. 27, 2009    (GB) .................................. 0905328.1

(51) Int. Cl.
*A61K 51/00*    (2006.01)
*A61K 36/14*    (2006.01)
(52) U.S. Cl.
USPC .......................... 424/1.11; 424/1.89; 424/9.1
(58) Field of Classification Search
USPC ................... 424/1.89, 9.1; 548/418, 421, 448
See application file for complete search history.

(56) References Cited

U.S. PATENT DOCUMENTS 6,281,355 B1 *  8/2001  Nakazato et al. ................ 544/14
6,451,795 B1    9/2002  Marguet

FOREIGN PATENT DOCUMENTS

| EP | 0248734 | 12/1987 |
| WO | 99/25340 | 5/1999 |
| WO | 00/44751 | 8/2000 |
| WO | 03/014082 | 2/2003 |
| WO | 03/016277 | 2/2003 |
| WO | 2007/057705 | 5/2007 |
| WO | WO-2007/057705 | * 5/2007 |

OTHER PUBLICATIONS

Kozikowksi et al., Chemistry, binding affinities, and behavioral properties of a new class of antineophobic mitochondrail DBI receptor comples (MDRC) ligands, J of Med. Chem, 1993, 36 (20), 2908-2920.*
Kozikowksi, et.al. "Chemistry, Binding Affinities, and Behavioral Properties of a New Class of 'Antineophobic' Mitochondrial DBI Receiptor Comples (MDRC) Ligands" Journal of Medicinal Chemistry 1993, vol. 36, No. 20, pp. 2908-2920.
Taketoshi Okubo, et.al. "Design Synthesis, and Structure-Activity Relationships of Novel Tetracyclic Compounds as Peripheral Benzodiazepine Receptor Ligands" Bioorganic & Medicinal Chemiistry, Pergamon, GB Linkd, vol. 12, Jan. 1, 2004, pp. 3569-3580.
Da Settimo, et.al. " Isoteric Replacement of the Indole Nucleus by Benzothiophene and Benzofuran in a Series of Indolylglyoxylylamine Derivatives With Partial Agonist Activity at the Benzodiazepine Receptor" European Journal of Medicinal Chemistry, vol. 31, No. 12, Jan. 1, 1996 pp. 951-056.
Da Settimo, et.al. "Synthesis of 3-(2'-Furoyl)Indole Derivatvies as Potential New Ligands at the Benzodiazepine Receptor, Structurally More Restrained Analoguesof Indoleglyoxylylamides" Farmaco 1995, vol. 50, No. 5, pp. 311-320.
Homes, et.al "Synthesis and In Vitro Binding of N, N-Dialkyl-2-Phenylindol-3-Yl-Glyo Xylamides and the Peripheral Benzodiazepine Binding Sites" Bioorganic & Medicinal Chemistry, Pergamon, vol. 14, No. 11 Jun. 1, 2006 pp. 3938-3946.
Bennacef, et.al. "Synthesis and Receptor Binding Studies of Halogenated N,N-Dialkylel-2(2-Phenyl-1H-Indol-3-Yl)Glyo Xylamides to Visualize Peripheral Benzodiazepine Receptors With Spect or Pet" Bioorganic & Medicinal Chemistry, Pergamon, vol. 14, No. 22, Nov. 15, 2006 pp. 7582-7591.
Primofiore, et.al. "N,N-Dialkyl-2-Phenylindol-3-Ylglyoxylamides. A New Class of Potent and Selective Ligands at the Peripheral Renzodiazepine Receptor" Journal of Medicinal Chemistry vol. 47, No. 7, Mar. 25, 2004 pp. 1852-1855.
PCT/EP2010/053998 ISRWO Dated Sep. 24, 2010.
GB0905328.1 Search Report Dated Jun. 9, 2009.

* cited by examiner

*Primary Examiner* — Michael G Hartley
*Assistant Examiner* — Jagadishwar Samala

(57) ABSTRACT

An indole-based in vivo imaging agent is provided by the present invention that binds with high affinity to PBR, has good uptake into the brain following administration, and which has good selective binding to PBR. The invention also includes a precursor compound useful in the synthesis of the in vivo imaging agent of the invention, as well as a method for synthesis of said in vivo imaging agent comprising use of said precursor compound, and a kit for carrying out said method. Also provided is a cassette for automated synthesis of the in vivo imaging agent. Further aspects of the invention include a radiopharmaceutical composition comprising the in vivo imaging agent of the invention, and methods for the use of said in vivo imaging agent.

16 Claims, 19 Drawing Sheets

Imaging Agent 5

Imaging Agent 5 co-eluting with reference standard

Imaging Agent 6

Imaging Agent 6 co-eluting with reference standard

Imaging Agent 7

Imaging Agent 7 co-eluting with reference standard

Imaging Agent 9

Imaging Agent 9 co-eluting with reference standard

Imaging Agent 10

Structural Isomer co-eluted with structural isomer reference standard overlayed with imaging agent 10 formulated trace Imaging Agent 11

Imaging Agent 11 co-eluting with reference standard

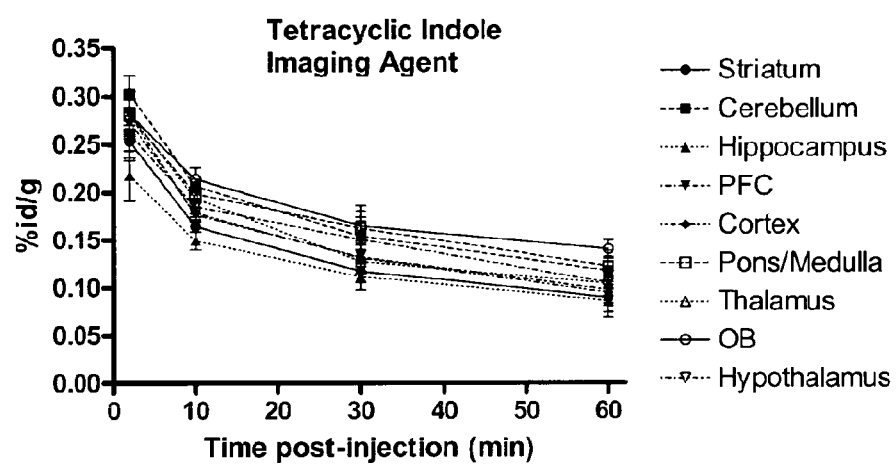
Figure 7: Brain biodistribution of tetracyclic indole imaging agent

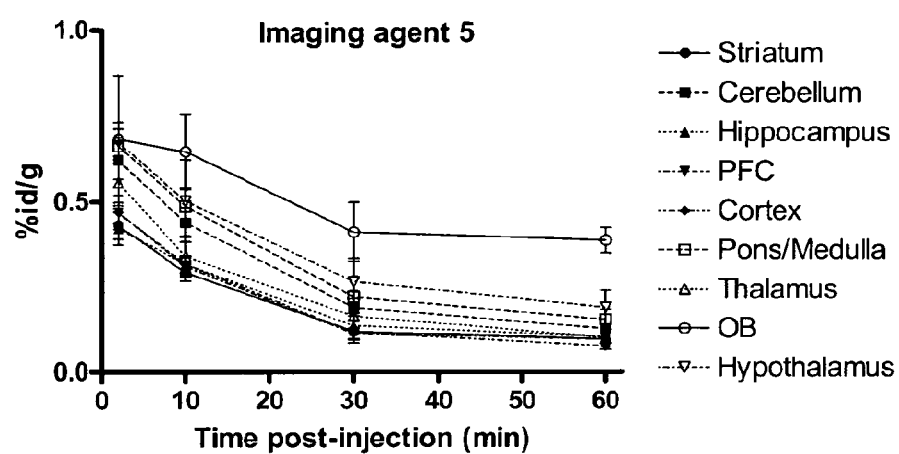
Figure 8: Brain biodistribution of imaging agent 5

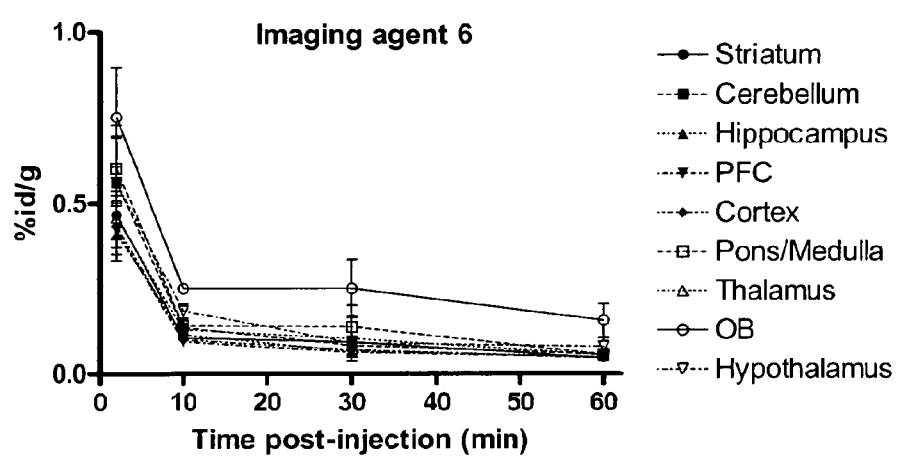
Figure 9: Brain biodistribution of imaging agent 6

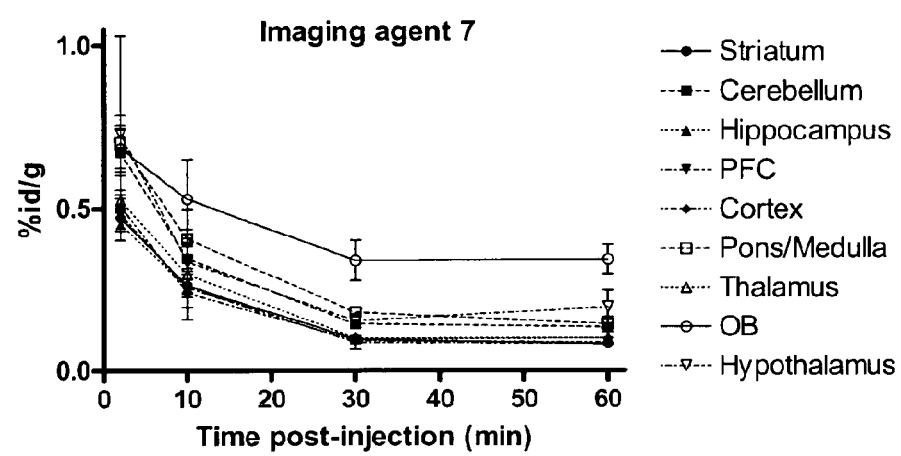
Figure 10: Brain biodistribution of imaging agent 7

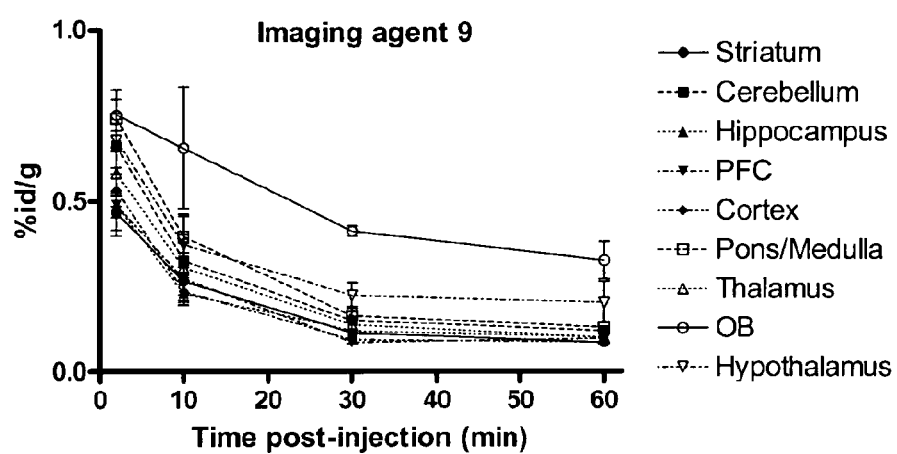
Figure 11: Brain biodistribution of imaging agent 9

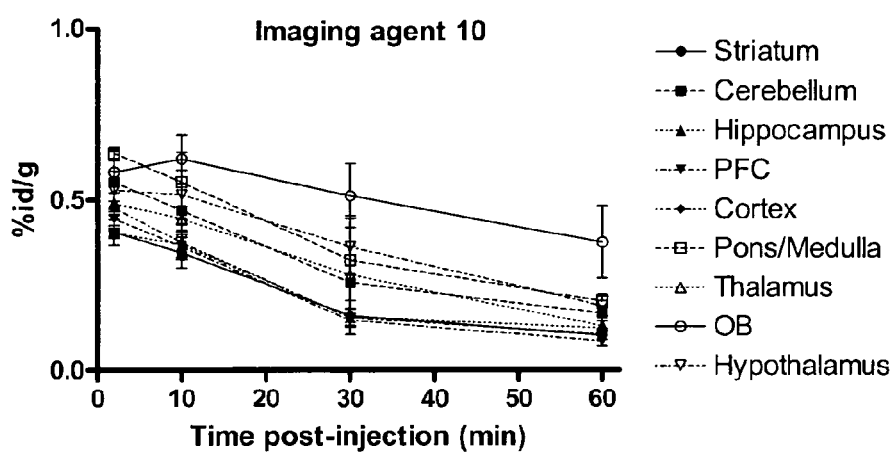
Figure 12: Brain biodistribution of imaging agent 10

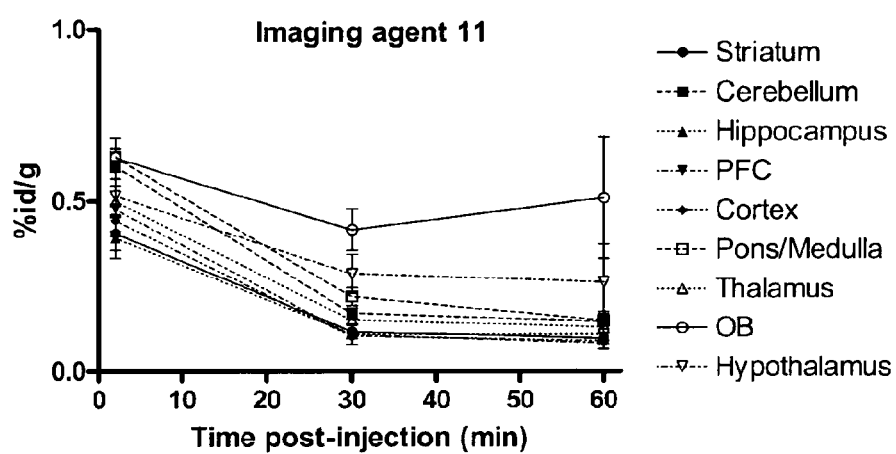
Figure 13: Brain biodistribution of imaging agent 11

INDOLE DERIVATIVES

This application is a filing under 35 U.S.C. 371 of international application number PCT/EP2010/053998, filed Mar. 26, 2010, which claims priority to U.S. application No. 61/164,131 filed Mar. 27, 2009 and Great Britain application number 0905328.1 filed Mar. 27, 2009, the entire disclosure of each of which is hereby incorporated by reference.

TECHNICAL FIELD OF THE INVENTION

The present invention concerns in vivo imaging and in particular in vivo imaging of the peripheral benzodiazepine receptor (PBR). An indole-based in vivo imaging agent is provided that binds with high affinity to PBR, has good uptake into the brain following administration, and which has good selective binding to PBR. The present invention also provides a precursor compound useful in the synthesis of the in vivo imaging agent of the invention, as well as a method for synthesis of said precursor compound. Other aspects of the invention include a method for the synthesis of the in vivo imaging agent of the invention comprising use of the precursor compound of the invention, a kit for carrying out said method, and a cassette for carrying out an automated version of said method. In addition, the invention provides a radiopharmaceutical composition comprising the in vivo imaging agent of the invention, as well as methods for the use of said in vivo imaging agent.

DESCRIPTION OF RELATED ART

The peripheral benzodiazepine receptor (PBR) is known to be mainly localised in peripheral tissues and glial cells but its physiological function remains to be clearly elucidated. Subcellularly, PBR is known to localise on the outer mitochondrial membrane, indicating a potential role in the modulation of mitochondrial function and in the immune system. It has furthermore been postulated that PBR is involved in cell proliferation, steroidogenesis, calcium flow and cellular respiration.

Abnormal PBR expression has been associated with inflammatory disease states of the central nervous system (CNS), including multiple sclerosis (Banati et al 2001 Neuroreport; 12(16): 3439-42; Debruyne et al 2002 Acta Neurol Belg; 102(3): 127-35), Rasmeussen's encephalitis (Banati et al 1999 Neurology; 53(9): 2199-203) cerebral vasculitis (Goerres et at 2001 Am J Roentgenol; 176(4): 1016-8), herpes encephalitis (Cagnin et al 2001 Brain; 124(Pt 10): 2014-27), and AIDS-associated dementia (Hammoud et al 2005 J Neurovirol; 11(4): 346-55).

Also in the CNS, a link with PBR has been documented in degenerative diseases such as Parkinson's disease (Gerhard et al 2006 Neurobiol Dis; 21(2): 404-12; Ouchi et al 2005 Ann Neurol; 57(2): 161-2), corticobasal degeneration (Gerhard et al 2004 Mov Disord; 19(10): 1221-6), progressive supranuclear palsy (Gerhard et al 2006 Neurobiol Dis; 21(2): 404-12), multiple system atrophy (Gerhard et al 2003 Neurology; 61(5): 686-9), Huntington's Disease (Pavese et al 2006 Neurology; 66(11): 1638-43; Tai et al 2007 Brain Res Bull; 72(2-3): 148-51), amyotrophic lateral sclerosis (Turner et al 2004 Neurobiol Dis; 15(3): 601-9), and Alzheimer's disease (Cagnin et al 2001 Lancet; 358(9283): 766; Yasuno et al 2008 Biol Psychiatry; 64(10): 835-41).

A number of CNS ischemic conditions have been shown to be related to abnormal PBR expression, including; ischemic stroke (Gerhard et al 2005 Neuroimage; 24(2): 591-5), peripheral nerve injury (Banati et al 2001 Neuroreport; 12(16):3439-42), epilepsy (Sauvageau 2002 Metab Brain Dis; 17(1): 3-11, Kumar et al 2008 Pediatr Neurol; 38(6)). PBR has been postulated as a biomarker to determine the extent of damage in traumatic brain injury (Toyama et al 2008 Ann Nucl Med; 22(5): 417-24), with an increase in PBR expression reported in an animal model of traumatic brain injury (Venneti et al 2007 Exp Neurol; 207(1): 118-27). Interestingly, acute stress has been correlated with an increase in PBR expression in the brain, whereas chronic stress has been correlated with a downregulation of PBR (Lehmann et al 1999 Brain Res; 851(1-2): 141-7). Delineation of glioma borders has been reported to be possible using [$^{11}$C]PK11195 to image PBR (Junck et al 1989 Ann Neurol; 26(6): 752-8). PBR may also be associated with neuropathic pain, Tsuda et al having observed activated microglia in subjects with neuropathic pain (2005 TINS 28(2) pp 101-7).

In the periphery, PBR expression has been linked with lung inflammation (Branley et al 2008 Nucl. Med. Biol; 35(8): 901-9), chronic obstructive pulmonary disease and asthma (Jones et al 2003 Eur Respir J; 21(4): 567-73), inflammatory bowel disease (Ostuni et al Inflamm Bowel Dis; 2010 online publication), rheumatoid arthritis (van der Laken et al 2008 Arthritis Rheum; 58(11): 3350-5), primary fibromyalgia (Faggioli et al 2004 Rheumatology; 43(10): 1224-1225), nerve injury (Durrenberger et al 2004 J Peripher Nerv Syst; 9(1): 15-25), atherosclerosis (Fujimura et al 2008 Atherosclerosis; 201(1): 108-111), colon, prostate and breast cancer (Deane et al 2007 Mol Cancer Res; 5(4): 341-9; Miettinen et al 1995 Cancer Res; 55(12): 2691-5; Han et al 2003 J Recept Signal Transduct Res; 23(2-3): 225-38), kidney inflammation (Tam et al 1999 Nephrol Dial Transplant; 14(7): 1658-66; Cook et al 1999 Kidney Int; 55(4): 1319-26), and ischemia-reperfusion injury (Zhang et al 2006 J Am Coll Surg; 203(3): 353-64).

Positron emission tomography (PET) imaging using the PBR selective ligand, (R)-[$^{11}$C]PK11195 provides a generic indicator of central nervous system (CNS) inflammation. However, (R)-[$^{11}$C]PK11195 is known to have high protein binding, and low specific to non-specific binding. Furthermore, the role of its radiolabelled metabolites is not known, and quantification of binding requires complex modelling.

Tricyclic indole compounds are known in the art. Davies et al (J. Med. Chem. 1998; 41(4): 451-67) teach a class of tricyclic indole compounds and characterise them as melatonin agonists and antagonists. Napper et al (J. Med. Chem. 2005; 48: 8045-54) teach and discuss the structure-activity relationship for a class of tricyclic indole compounds in the context of selective inhibition of the enzyme SIRT1, a member of the family of enzymes that removes acetyl groups from lysine residues in histones and other proteins. Another class of tricyclic indole compounds are disclosed in U.S. Pat. No. 6,451,795 and are discussed as useful in the treatment of PBR-related disease states. U.S. Pat. No. 6,451,795 discloses IC$_{50}$ values for the most active compounds of between 0.2 nM and 5.0 nM, and states that the compounds are useful for the prevention or treatment of peripheral neuropathies and for the treatment of central neurodegenerative diseases.

Okubu et al (Bioorganic & Medicinal Chemistry 2004 12 3569-80) describe the design, synthesis and structure of a group of tetracyclic indole compounds, as well as their affinity for PBR (IC$_{50}$ values as low as about 0.4 nM). WO 2007/057705, assigned to the present applicant, discloses tetracyclic indole derivatives labelled with a range of in vivo imaging moieties. Preferred in vivo imaging moieties disclosed by WO 2007/057705 are those which are suitable for positron emission tomography (PET) or single-photon emission tomography (SPECT) imaging, most preferably PET.

In addition, co-pending patent application PCT/EP2009/062827 describes tetracyclic indole-derived in vivo imaging agents similar to those of WO 2007/057705.

The tetracyclic indole derivatives described in WO 2007/057705 and in co-pending patent application PCT/EP2009/062827 have good affinity for the PBR receptor, and a high proportion of radioactivity in the brain at 60 minutes post-injection represents the parent in vivo imaging agent. Although these tetracyclic indole derivatives also achieve a reasonable initial concentration in the rat brain in biodistribution studies, the uptake is still relatively low and could be improved upon. The present inventors have also found that the relative retention in the olfactory bulb (the brain region having the highest concentration of PBR receptor) of these prior art tetracyclic indole derivatives is not as high as desirable for in vivo imaging. There is therefore scope for a PBR in vivo imaging agent that retains the advantageous properties of the above-described prior art tetracyclic indole in vivo imaging agents, but that has improved brain uptake and improved specific binding to the PBR receptor.

BRIEF DESCRIPTION OF THE DRAWINGS

FIG. 7 shows brain biodistribution of tetracyclic indole imaging agent.

FIG. 8 shows brain biodistribution of imaging agent 5.
FIG. 9 shows brain biodistribution of imaging agent 6.
FIG. 10 shows brain biodistribution of imaging agent 7.
FIG. 11 shows brain biodistribution of imaging agent 9.
FIG. 12 shows brain biodistribution of imaging agent 10
FIG. 13 shows brain biodistribution of imaging agent 11.

SUMMARY OF THE INVENTION

Figure 1:
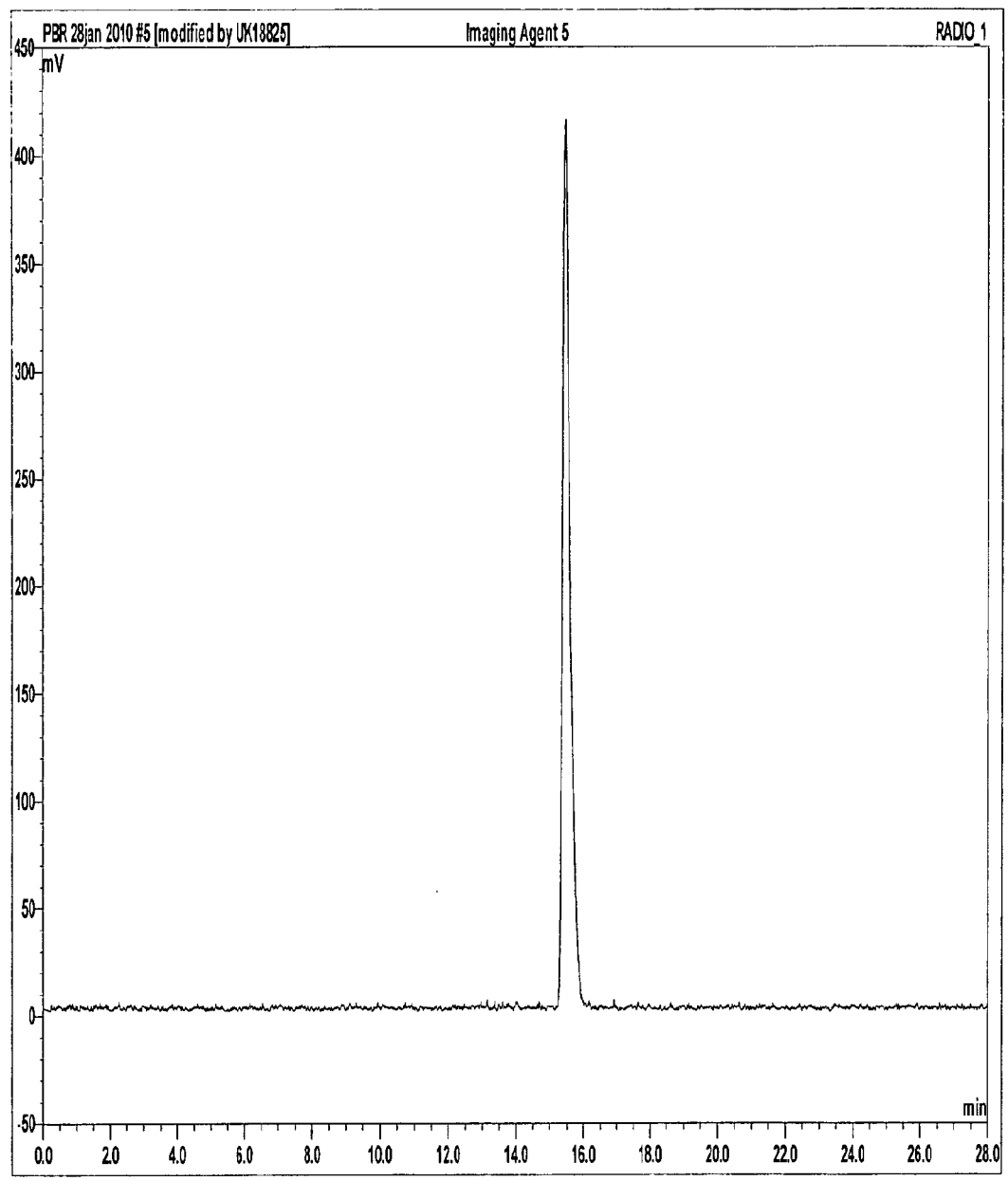
FIG. 1 shows co-elution of imaging agent 5 and non-radioactive imaging agent 5.
Figure 1:
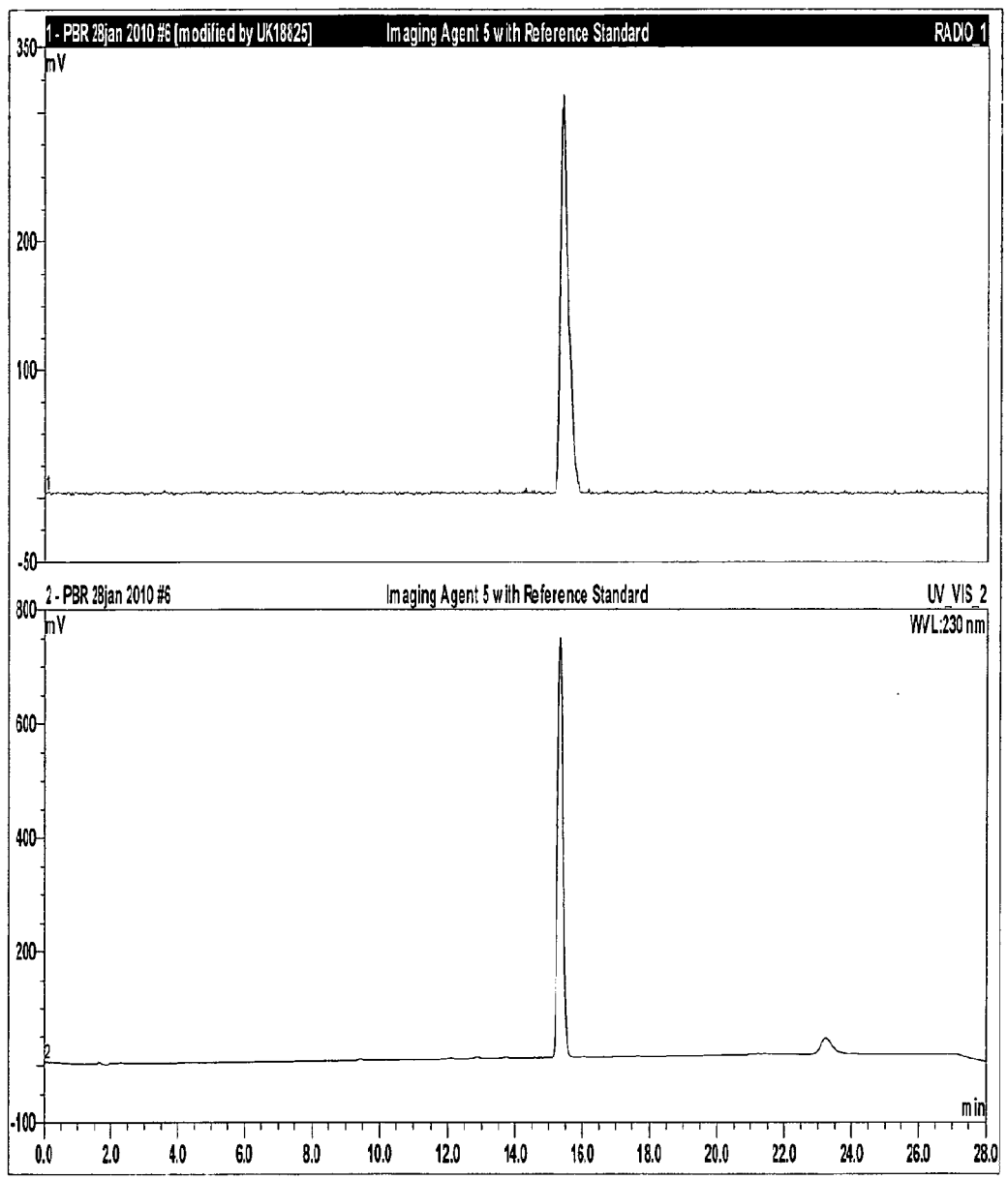

The present invention provides a novel tricyclic indole compound suitable for use as an in vivo imaging agent. The present invention also provides a precursor compound useful in the synthesis of the in vivo imaging agent of the invention, as well as a method for synthesis of said precursor compound. A method for the preparation of the in vivo imaging agent is also provided comprising use of the precursor compound of the invention. A pharmaceutical composition comprising the in vivo imaging agent of the invention is additionally provided, in addition to a kit suitable for the facile preparation of the pharmaceutical composition. In a farther aspect, use of the in vivo imaging agent for in vivo imaging of a condition associated with abnormal PBR expression is provided. The in vivo imaging agent of the present invention retains the advantageous properties of known tetracyclic in vivo imaging agents, in conjunction with improved brain uptake and specificity for the peripheral benzodiazepine receptor.

DETAILED DESCRIPTION OF THE INVENTION

Imaging Agent

In one aspect, the present invention provides an in vivo imaging agent of Formula I:

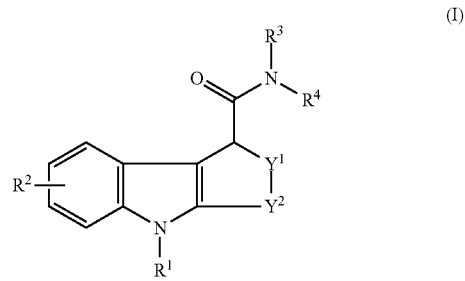

(I)

wherein:
R$^1$ is C$_{1-3}$ alkyl or C$_{1-3}$ fluoroalkyl;
R$^2$ is hydrogen, hydroxyl, halo, cyano, C$_{1-3}$ alkyl, C$_{1-3}$ alkoxy, C$_{1-3}$ fluoroalkyl, or C$_{1-3}$ fluoroalkoxy;
R$^3$ and R$^4$ are independently C$_{1-3}$ alkyl, C$_{7-10}$ aralkyl, or R$^3$ and R$^4$, together with the nitrogen to which they are attached, form a nitrogen-containing C$_{4-6}$ aliphatic ring optionally comprising 1 further heteroatom selected from nitrogen, oxygen and sulfur;
Y$^1$ is O, S, SO, SO$_2$ or CH$_2$; and,
Y$^2$ is CH$_2$, CH$_2$—CH$_2$, CH(CH$_3$)—CH$_2$ or CH$_2$—CH$_2$—CH$_2$;
and wherein Formula I as defined comprises an atom which is a radioisotope suitable for in vivo imaging.

An "in vivo imaging agent" in the context of the present invention is a radiolabelled compound suitable for in vivo imaging. The term "in vivo imaging" as used herein refers to those techniques that noninvasively produce images of all or part of the internal aspect of a subject.

Unless otherwise specified, the term "alkyl" alone or in combination, means a straight-chain or branched-chain alkyl radical containing preferably from 1 to 3 carbon atoms. Examples of such radicals include, methyl, ethyl, and propyl.

Unless otherwise specified, the term "alkoxy" means an alkyl radical as defined above comprising an ether linkage, and the term "ether linkage" refers to the group —C—O—C—. Examples of suitable alkyl ether radicals include, methoxy, ethoxy, and propoxy.

The teen "halogen" or "halo-" means a substituent selected from fluorine, chlorine, bromine or iodine. "Haloalkyl" and "haloalkoxy" are alkyl and alkoxy groups, respectively, as defined above substituted with one or more halogens. Suitably in the case of haloalkyl and haloalkoxy substituents, the halogen replaces a hydrogen at the terminal end of the radical, i.e. -alkylene-halogen or -alkoxylene-halogen. The term "alkylene" refers to the bivalent group —(CH$_2$)$_n$— wherein n is 1-3, and the term "alkoxylene" refers to an alkylene group comprising an ether linkage, wherein an ether linkage is as defined above.

The term "cyano" refers to the group —CN.
The term "hydroxyl" refers to the group —OH.
The term "aralkyl" refers to the group -alkylene-phenyl wherein alkylene is as defined above.

A "nitrogen-containing C$_{4-6}$ aliphatic ring" is a saturated C$_{4-6}$ alkyl ring comprising a nitrogen heteroatom. Examples include pyrrolidinyl, piperidinyl and morpholinyl rings.

The term "comprises an atom which is a radioisotope suitable for in vivo imaging" means that in Formula I as defined above, the isotopic form of one of the atoms is a radioisotope suitable for in vivo imaging. In order to be suitable for in vivo imaging, the radioisotope is detectable externally following administration to said subject.

If a chiral centre or another form of an isomeric centre is present in an in vivo imaging agent according to the present invention, all forms of such isomer, including enantiomers and diastereoisomers, are encompassed by the present invention. In vivo imaging agents of the invention containing a chiral centre may be used as racemic mixture or as an enantiomerically-enriched mixture, or the racemic mixture may be separated using well-known techniques and an individual enantiomer may be used alone.

Preferred Imaging Agents $R^1$ is preferably methyl or $C_{2-3}$ fluoroalkyl, and most preferably -ethylene-F (i.e. —$CH_2$—$CH_2$—F).

$R^2$ is preferably hydrogen, halo, $C_{1-3}$ alkoxy or $C_{1-3}$ fluoroalkoxy. $R^2$ is most preferably hydrogen, halo or $C_{1-3}$ alkoxy, and most especially preferably hydrogen, fluoro or methoxy. Where $R^2$ is a substituent it is preferably at the 5- or 6-position, and is most preferably selected from 5-methoxy, 6-methoxy, 5-fluoro and 6-fluoro.

$R^3$ and $R^4$ are preferably independently methyl, ethyl or benzyl, and are most preferably both ethyl.

Alternatively preferably, $R^3$ and $R^4$, together with the nitrogen to which they are attached, form a nitrogen-containing $C_{5-6}$ aliphatic ring.

$Y^1$ is preferably $CH_2$.

For the most preferred in vivo imaging agents of the present invention, $Y^2$ is $CH_2$—$CH_2$.

A preferred in vivo imaging agent of the invention is suitable for imaging using single photon emission computed tomography (SPECT) or positron emission tomography (PET). For SPECT, a suitable radioisotope is a gamma-emitting radioactive halogen. Examples of gamma-emitting radioactive halogens suitable for use in the present invention are $^{123}I$, $^{131}I$ and $^{77}Br$. A preferred gamma-emitting radioactive halogen is $^{123}I$. Where the radioisotope of the in vivo imaging agent is $^{123}I$ it is preferred that $R^2$ is $^{123}I$. For PET, a suitable radioisotope is a positron-emitting radioactive non-metal. Examples of positron-emitting radioactive non-metal suitable for use in the present invention are $^{11}C$, $^{18}F$ and $^{124}I$. Preferred positron-emitting radioactive non-metals are $^{11}C$ and $^{18}F$. In the case of $^{11}C$ it is preferred that $R^1$ is $^{11}C$ methyl. Where the radioisotope is $^{18}F$, it is preferred that $R^1$ is $C_{2-3}$ [$^{18}F$]fluoroalkyl, most preferably -ethylene-$^{18}F$.

It is preferred that the in vivo imaging agent of the invention is suitable for PET imaging, and $^{18}F$ is a preferred radioisotope suitable for PET imaging. The preference for PET in the method of the invention is due to its excellent sensitivity and resolution, so that even relatively small changes in a lesion can be observed over time. PET scanners routinely measure radioactivity concentrations in the picomolar range. Micro-PET scanners now approach a spatial resolution of about 1 mm, and clinical scanners about 4-5 mm.

A preferred in vivo imaging agent of Formula I is of Formula Ia:

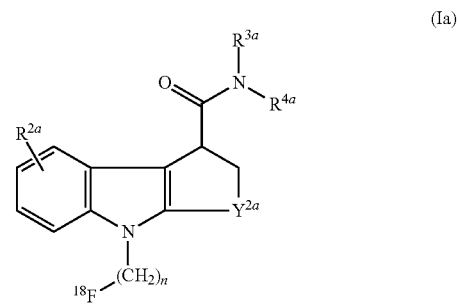

(Ia)

wherein:

$R^{2a}$ is hydrogen, halo or $C_{1-3}$ alkoxy;

$R^{3a}$ and $R^{4a}$ are independently methyl, ethyl or benzyl, or together with the nitrogen to which they are attached form a pyrrolidinyl, piperidinyl, azepanyl or morpholinyl ring;

$Y^{2a}$ is $CH_2$, $CH_2$—$CH_2$, $CH(CH_3)$—$CH_2$, or $CH_2$—$CH_2$—$CH_2$; and;

n is 1, 2 or 3.

In Formula Ia, $R^{3a}$ and $R^{4a}$ are preferably both ethyl, or $R^{3a}$ is methyl and $R^{4a}$ is benzyl, or together with the nitrogen to which they are attached form an azepanyl ring.

$R^{2a}$ is preferably hydrogen, methoxy or fluoro.

$Y^{2a}$ is preferably $CH_2$—$CH_2$ or $CH(CH_3)$—$CH_2$.

n is preferably 2.

In a preferred in vivo imaging agent of Formula Ia:

$R^{3a}$ and $R^{4a}$ are both ethyl, or $R^{3a}$ is methyl and $R^{4a}$ is benzyl, or together with the nitrogen to which they are attached form azepanyl;

$R^{2a}$ is hydrogen, methoxy or fluoro;

$Y^{2a}$ is $CH_2$—$CH_2$ or $CH(CH_3)$—$CH_2$; and, n is 2.

Non-limiting examples of in vivo imaging agents of Formula Ia are as follows:

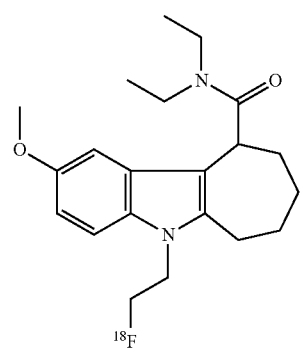

1

-continued
2
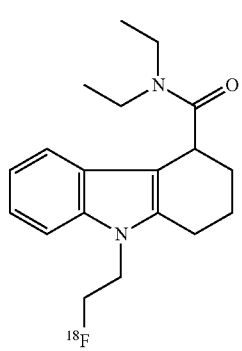
3
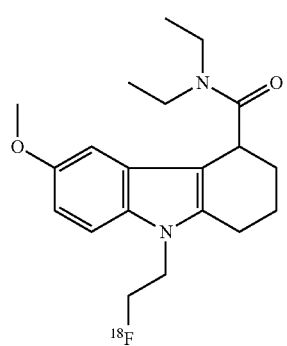
4
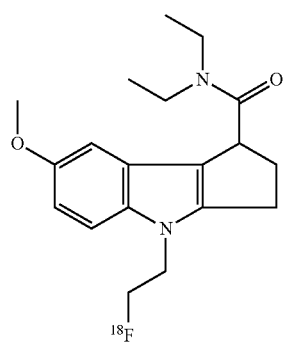
5
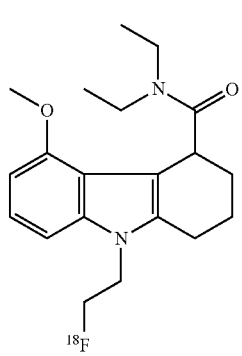
-continued
6
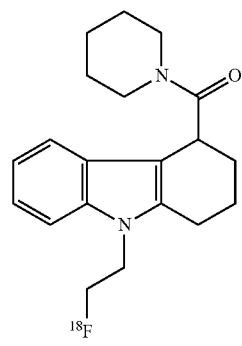
7
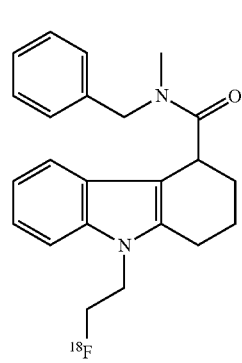
8
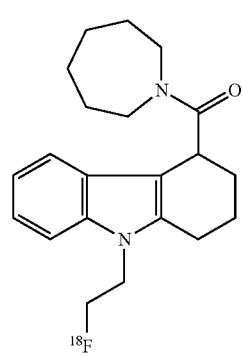
9
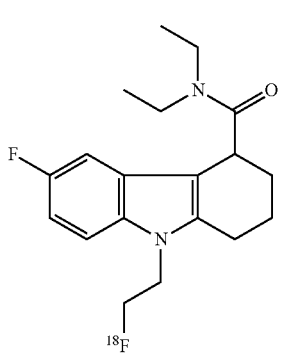

-continued

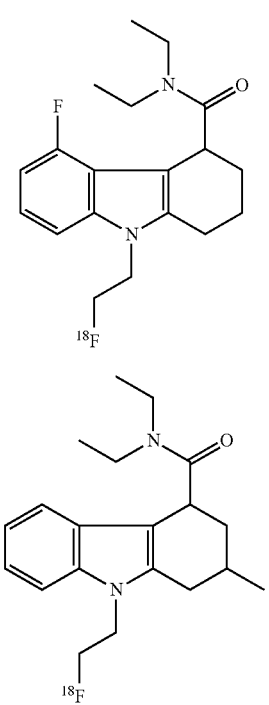

10

11

Out of in vivo imaging agents 1-11 above, in vivo imaging agents 5, 6, 7, 9, 10 and 11 are preferred, in vivo imaging agents 5 and 10 are most preferred, and in vivo imaging agent 5 is especially preferred. For any in vivo imaging agent of the present invention, the enantiomerically pure form is particularly preferred.

Precursor Compound

In another aspect, the present invention provides a precursor compound for the preparation of the in vivo imaging agent of the invention, wherein said precursor compound is of Formula II:

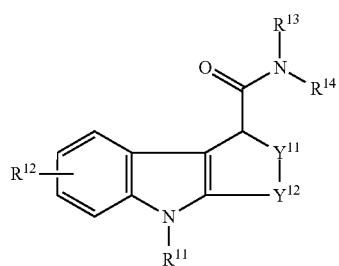

(II)

wherein one of $R^{11}$ and $R^{12}$ comprises a chemical group that reacts with a suitable source of the radioisotope as defined above for the in vivo imaging agent of the invention, such that an in vivo imaging agent of the invention is formed upon reaction of said precursor compound with said suitable source of said radioisotope, and the other of $R^{11}$ and $R^{12}$ is as defined herein for $R^1$ and $R^2$, respectively, and optionally comprises a protecting group; and, $R^{13-14}$ and $Y^{11-12}$ are as defined herein for $R^{3-4}$ and $Y^{1-2}$, respectively, and optionally each further comprise a protecting group.

A "precursor compound" comprises a non-radioactive derivative of a radiolabelled compound, designed so that chemical reaction with a convenient chemical form of the detectable label occurs site-specifically; can be conducted in the minimum number of steps (ideally a single step); and without the need for significant purification (ideally no further purification), to give the desired in vivo imaging agent. Such precursor compounds are synthetic and can conveniently be obtained in good chemical purity.

By the term "protecting group" is meant a group which inhibits or suppresses undesirable chemical reactions, but which is designed to be sufficiently reactive that it may be cleaved from the functional group in question to obtain the desired product under mild enough conditions that do not modify the rest of the molecule. Protecting groups are well known to those skilled in the art and are described in 'Protective Groups in Organic Synthesis', Theorodora W. Greene and Peter G. M. Wuts, (Third Edition, John Wiley & Sons, 1999).

The term "a suitable source of a radioisotope" means the radioisotope in a chemical form that is reactive with a substituent of the precursor compound such that the radioisotope becomes covalently attached to the precursor compound. For each particular radioisotope presented in the following section, one or more suitable sources of the radioisotope are discussed. The person skilled in the art of in vivo imaging agents will be familiar with these and other sources of radioisotopes that are suitable for application in the present invention.

Scheme 1 below is a generic reaction scheme that shows how to obtain compounds that can themselves be used as precursor compounds, or can be converted into precursor compounds with a small number of further steps. $R^{11-14}$ and $Y^{11-12}$ of Scheme 1 are as defined above for Formula II.

Scheme 1

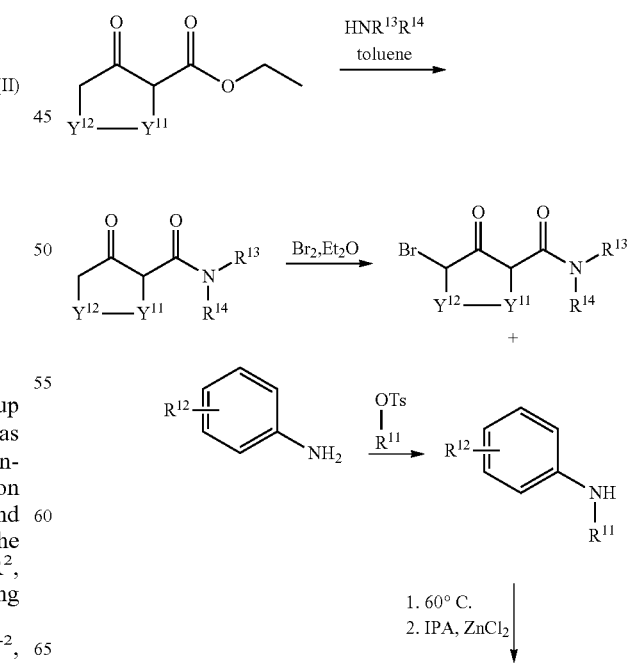

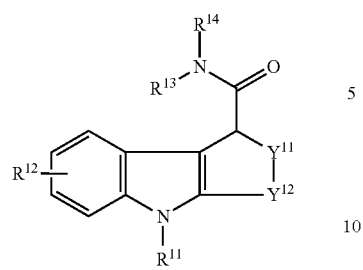
Alternatively, where $R^{12}$ of the precursor compound is at the top position on the ring, the general synthetic route illustrated in Scheme Ia below can be used:
Scheme 1a
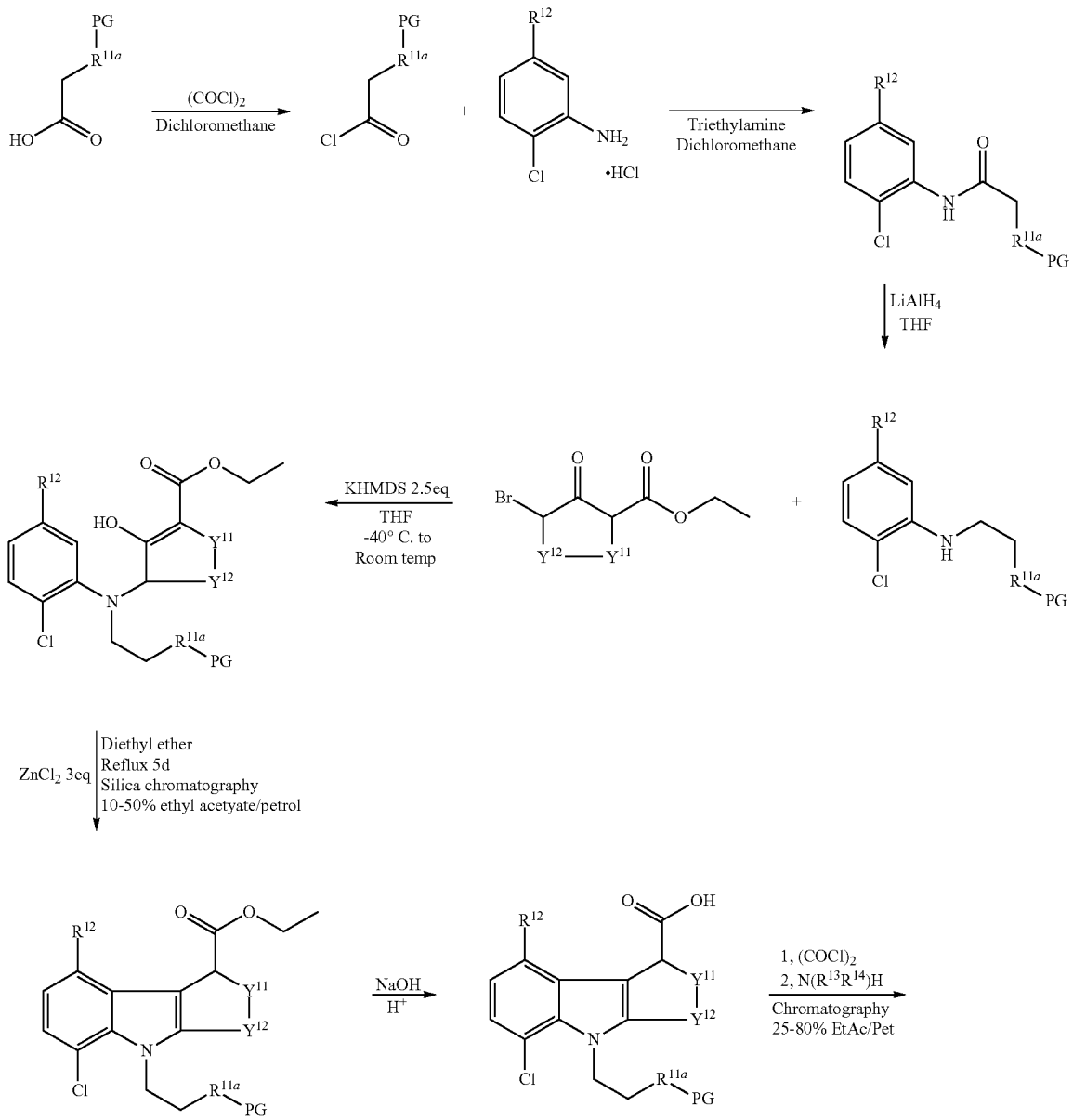

-continued

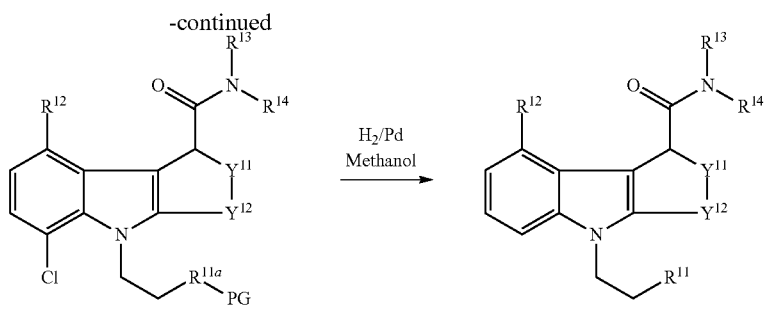

In Scheme 1a above, —$R^{11a}$—PG represents a protected $R^{11}$ group wherein $R^{11}$ is as suitably and preferably defined herein. Where $R^{11}$ is hydroxy —$R^{11a}$-PG may for example be —O-benzyl. $R^{12-14}$ and $Y^{11-12}$ are as suitably and preferably provided for Formula II above, with the proviso that $R^{12}$ is not chloro. In this synthetic route, the chlorine at the bottom position on the ring forces the cyclisation to take place in just one way such that only one isomer is produced. A similar method is disclosed in WO 2003/014082. However, when the present inventors applied the teachings of WO 2003/014082 to obtain precursor compounds of the present invention, the yield was low (see Example 2(d)). This problem was overcome by changing the solvent system used for the cyclisation step. In WO 2003/014082 the cyclisation step is carried out in toluene, whereas the present inventors found that optimum yields were obtained when diethyl ether was used in place of toluene. The product of the cyclisation step dissolves in diethyl ether whereas the uncyclised starting compound does not. The uncyclised starting compound therefore remains with the ZnCl$_2$ at the bottom of the reaction vessel, and the cyclised product moves into the diethyl ether at the top of the reaction vessel.

In a separate aspect therefore, the present invention provides a method for the preparation of a precursor compound of Formula IIb:

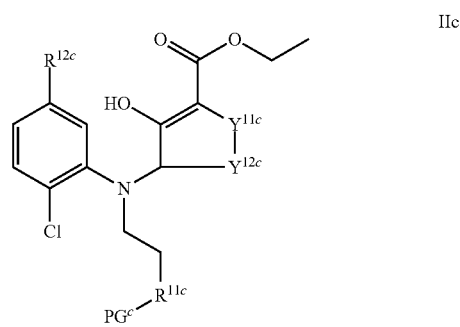

(IIb)

wherein:
$R^{11b}$ is as defined in Scheme 1a for $R^{11a}$;
$R^{12b-14b}$ are as defined for $R^{12-14}$ of Formula II, with the proviso that $R^{12b}$ is not chloro; and,
$Y^{11b-12b}$ are as defined for $Y^{11-12}$ of Formula II;

wherein said method comprises reaction with ZnCl$_2$ of a compound of Formula IIc:

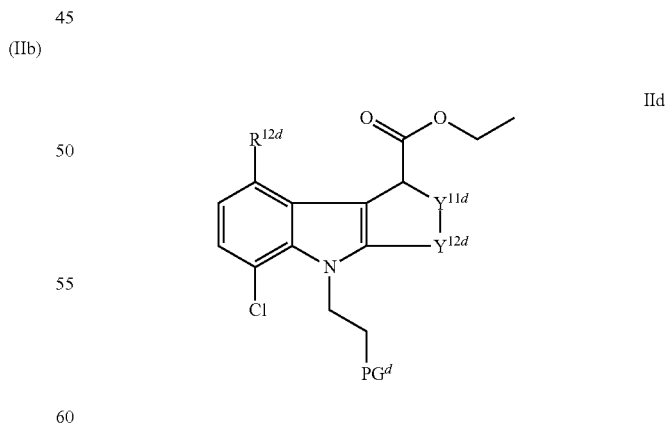

IIc wherein $R^{12c}$, $Y^{11c}$ and $Y^{12c}$ are as suitably and preferably defined herein for $R^{12}$, $Y^{11}$ and $Y^{12}$, respectively, and PG$^c$ is a protecting group;

to form a compound of Formula IId:

IId wherein $R^{12d}$, $Y^{11d}$, PG$^d$ are as defined for $R^{12c}$, $Y^{11c}$, $Y^{12c}$ and PG$^c$, respectively;

wherein said reaction is carried out in a solvent system comprising diethyl ether.

Preferably, said protecting group, $PG^c$, $PG^d$ is -benzyl. The precursor compound of Formula IIb represents a preferred precursor compound of Formula II.

When the radioisotope of the in vivo imaging agent is $^{18}F$, labelling with $^{18}F$ can be achieved by nucleophilic displacement of a leaving group from a precursor compound. Suitable leaving groups include Cl, Br, I, tosylate (OTs), mesylate (OMs) and triflate (OTf). Another strategy would be to have a suitable leaving group in place on an alkylamide group present on the precursor compound. In both cases, the precursor compound may be labeled in one step by reaction with a suitable source of $[^{18}F]$-fluoride ion ($^{18}F^-$), which is normally obtained as an aqueous solution from the nuclear reaction $^{18}O(p,n)^{18}F$ and is made reactive by the addition of a cationic counterion and the subsequent removal of water. $^{18}F$ can also be introduced by O-alkylation of hydroxyl groups in the precursor compound with $^{18}F(CH_2)_3$-LG wherein LG represents a leaving group as defined above. Alternatively, the radiofluorine atom may attach via a direct covalent bond to an aromatic ring such as a benzene ring. For aryl systems, $^{18}F$-fluoride nucleophilic displacement from an aryl diazonium salt, aryl nitro compound or an aryl quaternary ammonium salt are suitable routes to aryl-$^{18}F$ derivatives.

Either Scheme 1 or Scheme 1a above can be continued to arrive at precursor compounds suitable for obtaining $^{18}F$ in vivo imaging agents of the invention, as illustrated in Scheme 2 below:

Scheme 2

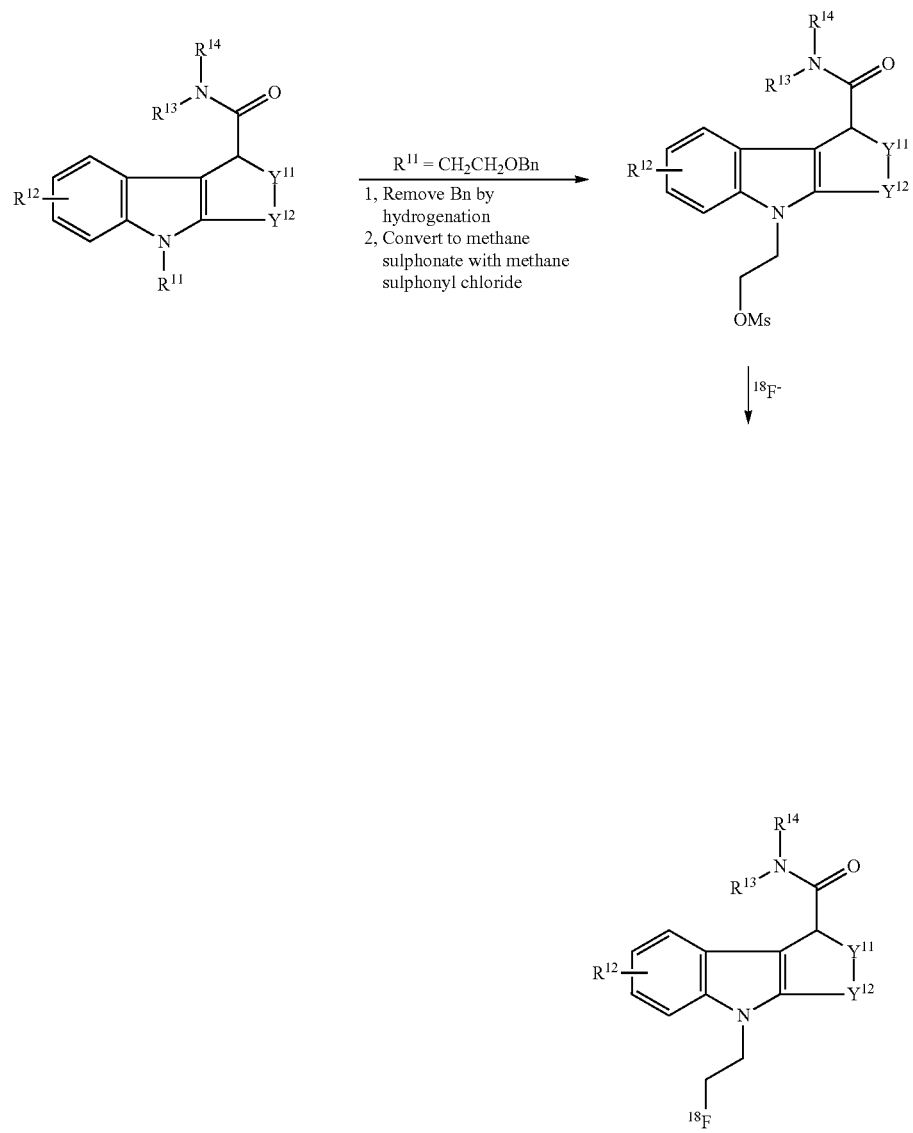

Starting compounds and intermediates are available commercially or are known from published scientific papers, e.g. Napper et al J Med Chem 2005; 48: 8045-54; Davies et al J Med Chem 1998; 41: 451-467.

In a preferred precursor compound of Formula II to obtain an in vivo imaging agent comprising $^{18}F$, $R^{11}$ is $C_{1-3}$ alkylene-LG wherein LG represents a leaving group. A most preferred such precursor compound is of Formula IIa:

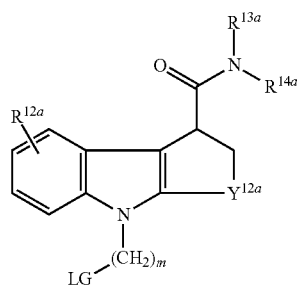
(IIa)

wherein:

LG is selected from mesylate, tosylate, and triflate; and, $R^{12a-14a}$, $Y^{12a}$ and m are as suitably and preferably defined above for $R^{2a-4a}$, $Y^{2a}$ and n, respectively of Formula Ia.

Non-limiting examples of preferred precursor compounds of Formula IIa are as follows:

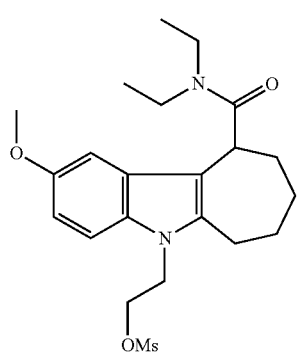
1

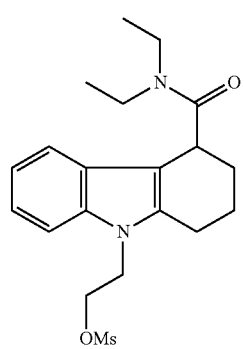
2

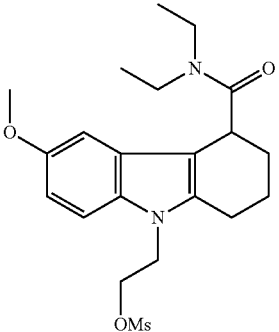
3

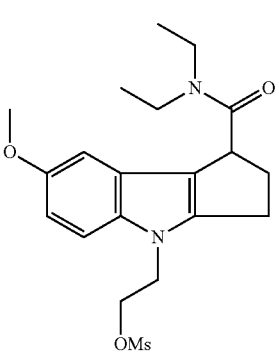
4

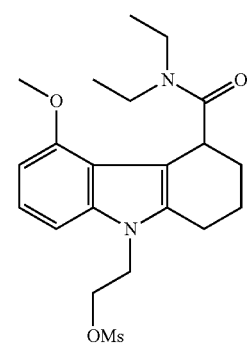
5

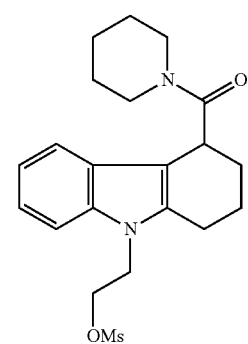
6

-continued

7 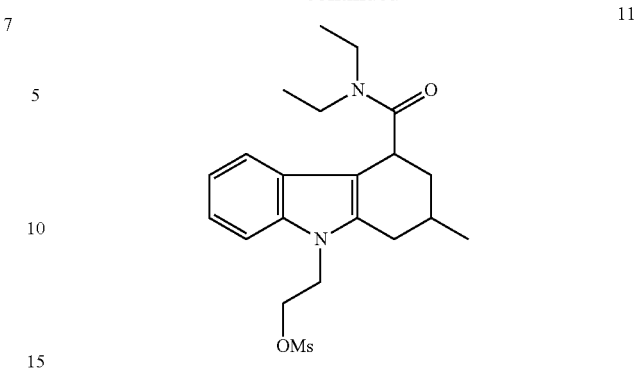

8 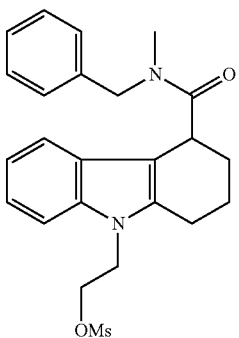

9 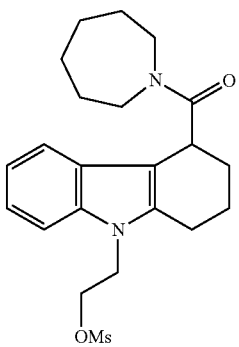

10 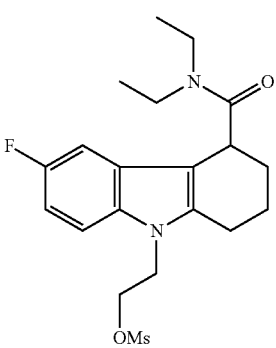

11 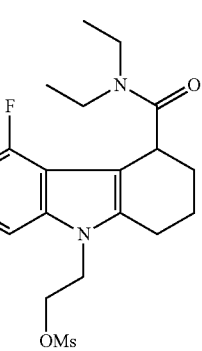

Out of precursor compounds 1-11 above, precursor compounds 5, 6, 7, 9, 10 and 11 are preferred, precursor compounds 5 and 10 are most preferred, and precursor compound 5 is especially preferred.

$^{11}$C-labelled PET tracer compounds may be synthesised by reacting a precursor compound with $^{11}$C methyl iodide. As the half-life of $^{11}$C is only 20.4 minutes, it is important that the intermediate "C methyl iodide has high specific activity and, consequently, that it is produced using a reaction process which is as rapid as possible. A thorough review of such" C-labelling techniques may be found in Antoni et al "Aspects on the Synthesis of $^{11}$C-Labelled Compounds" in Handbook of Radiopharmaceuticals, Ed. M. J. Welch and C. S. Redvanly (2003, John Wiley and Sons).

$^{11}$C-labelled in vivo imaging agents of the invention can be obtained by continuation of Scheme 1 above as illustrated in Scheme 3 below:

Scheme 3

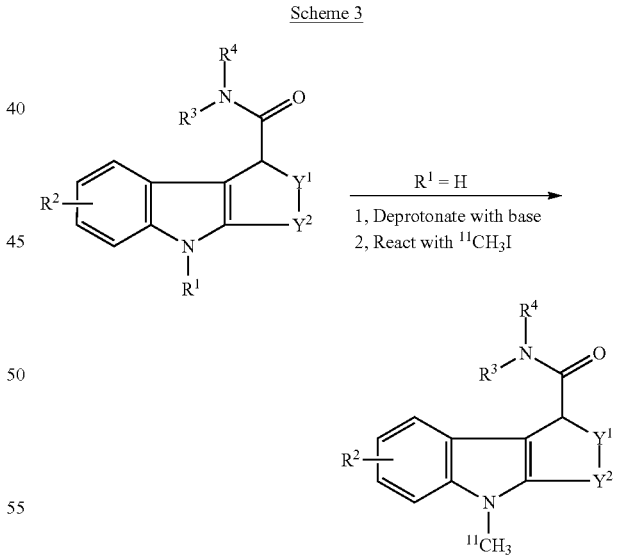

Where the imaging moiety is radioiodine, preferred precursor compounds are those which comprise a derivative which either undergoes electrophilic iodination. Examples of this are organometallic derivatives such as a trialkylstannane (e.g. trimethylstannyl or tributylstannyl), or a trialkylsilane (e.g. trimethylsilyl) or an organoboron compound (e.g. boronate esters or organotrifluoroborates).

For electrophilic radioiodination, the precursor compound preferably comprises: an activated organometallic precursor compound (e.g. trialkyltin, trialkylsilyl or organoboron compound). Precursor compounds and methods of introducing radioiodine into organic molecules are described by Bolton (J. Lab. Comp. Radiopharm. 2002; 45: 485-528). Suitable boronate ester organoboron compounds and their preparation are described by Kabalaka et al (Nucl. Med. Biol., 2002; 29: 841-843 and 2003; 30: 369-373). Suitable organotrifluoroborates and their preparation are described by Kabalaka et al (Nucl. Med. Biol., 2004; 31: 935-938). Preferred precursor compounds for radioiodination comprise an organometallic precursor compound, most preferably a trialkyltin.

Radioiodine labelled in vivo imaging agents of the invention can be obtained by continuation of Scheme 1 above as illustrated in Scheme 4 below:

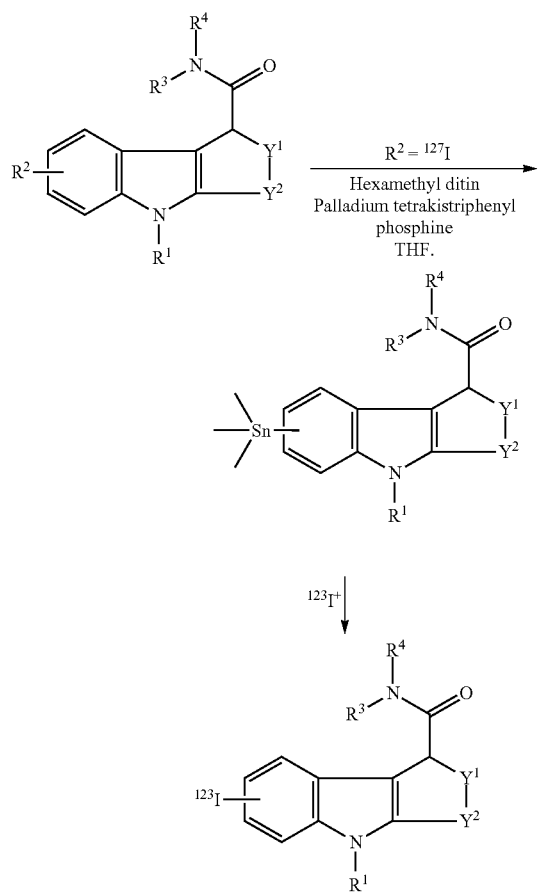

Scheme 4

Radiobromination can be achieved by methods similar to those described above for radioiodination. Kabalka and Vatma have reviewed various methods for the synthesis of radiohalogenated compounds, including radiobrominated compounds (Tetrahedron 1989; 45(21): 6601-21).

The precursor compound of the invention is ideally provided in sterile, apyrogenic form. The precursor compound can accordingly be used for the preparation of a pharmaceutical composition comprising the in vivo imaging agent together with a biocompatible carrier suitable for mammalian administration. The precursor compound is also suitable for inclusion as a component in a kit or in a cassette for the preparation of such a pharmaceutical composition. These aspects are discussed in more detail below.

In another preferred embodiment, the precursor compound is bound to a solid phase. The precursor compound is preferably supplied covalently attached to a solid support matrix. In this way, the desired product forms in solution, whereas starting materials and impurities remain bound to the solid phase. As an example of such a system, precursor compounds for solid phase electrophilic fluorination with $^{18}$F-fluoride are described in WO 03/002489, and precursor compounds for solid phase nucleophilic fluorination with $^{18}$F-fluoride are described in WO 03/002157.

Method for Preparation

In a further aspect, the present invention provides a method for the preparation of the in vivo imaging agent of the invention, said method comprising:
(i) providing a precursor compound of the invention;
(ii) providing a suitable source of said radioisotope as defined herein;
(iii) reacting the precursor compound of step (i) with the radioisotope of step (ii) to obtain the in vivo imaging agent of the invention.

In step (i), the precursor compound may be provided in solution in a kit or in a cassette suitable for use with an automated synthesis apparatus, or alternatively attached to a solid support, as described above in the description of the precursor compound. The kit and cassette form additional aspects of the invention and will be discussed in more detail below.

The step of "reacting" the precursor compound with the radioisotope involves bringing the two reactants together under reaction conditions suitable for formation of the desired in vivo imaging agent in as high a radiochemical yield (RCY) as possible. Some particular synthetic routes for obtaining in vivo imaging agents of the present invention are presented in the experimental section below.

For the method for preparation of the invention, the suitable and preferred embodiments of the in vivo imaging agent, precursor compound and radioisotope are as already provided herein.

Kit and Cassette

In a yet further aspect, the present invention provides a kit for the preparation of an in vivo imaging agent of the invention, said kit comprising a precursor compound of the invention, so that reaction with a sterile source of a radioisotope gives the desired in vivo imaging agent with the minimum number of manipulations. Such considerations are particularly important where the radioisotope has a relatively short half-life, and for ease of handling and hence reduced radiation dose for the radiopharmacist. The precursor compound is preferably present in the kit in lyophilized form, and the reaction medium for reconstitution of such kits is preferably a biocompatible carrier.

The "biocompatible carrier" is a fluid, especially a liquid, in which the in vivo imaging agent is suspended or dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The biocompatible carrier may also comprise biocompatible organic solvents such as ethanol. Such organic solvents are useful to solubilise more lipophilic compounds or formulations. Preferably the biocompatible carrier is pyrogen-free water for injection, isotonic saline or an aqueous ethanol solution. The pH of the biocompatible carrier for intravenous injection is suitably in the range 4.0 to 10.5.

In the kit of the invention, the precursor compound is preferably presented in a sealed container which permits maintenance of sterile integrity and/or radioactive safety, plus optionally an inert headspace gas (e.g. nitrogen or argon), whilst permitting addition and withdrawal of solutions by syringe. A preferred sealed container is a septum-sealed vial, wherein the gas-tight closure is crimped on with an overseal (typically of aluminium). Such sealed containers have the additional advantage that the closure can withstand vacuum if desired e.g. to change the headspace gas or degas solutions.

Preferred embodiments of the precursor compound when employed in the kit are as previously described herein.

The precursor compound for use in the kit may be employed under aseptic manufacture conditions to give the desired sterile, non-pyrogenic material. The precursor compound may alternatively be employed under non-sterile conditions, followed by terminal sterilisation using e.g. gamma-irradiation, autoclaving, dry heat or chemical treatment (e.g. with ethylene oxide). Preferably, the precursor compound is provided in sterile, non-pyrogenic form. Most preferably the sterile, non-pyrogenic precursor compound is provided in the sealed container as described above.

Preferably, all components of the kit are disposable to minimise the possibilities of contamination between runs and to ensure sterility and quality assurance.

[$^{18}$F]-radiotracers in particular are now often conveniently prepared on an automated radiosynthesis apparatus. There are several commercially-available examples of such apparatus, including Tracerlab™ and Fastlab™ (GE Healthcare Ltd). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps.

The present invention therefore provides in another aspect a cassette for the automated synthesis of an in vivo imaging agent as defined herein comprising:
(i) a vessel containing a precursor compound as defined herein; and
(ii) means for eluting the vessel with a suitable source of said radioisotope suitable for in vivo imaging as defined herein.

For the cassette of the invention, the suitable and preferred embodiments of the precursor compound and suitable source of radioisotope are as previously defined herein.

The cassette may additionally comprise:
(iii) an ion-exchange cartridge for removal of excess radioisotope; and optionally,
(iv) where the precursor compound comprises one or more protecting groups, a cartridge for deprotection of the resultant radiolabelled product to form an in vivo imaging agent as defined herein.

Radiopharmaceutical Composition

In another further aspect, the present invention provides a "radiopharmaceutical composition", which is a composition comprising the in vivo imaging agent of the invention, together with a biocompatible carrier in a form suitable for mammalian administration. The biocompatible carrier is as defined above in relation to the kit of the invention. For the radiopharmaceutical composition of the invention, the suitable and preferred embodiments of the in vivo imaging agent are as defined earlier in the specification.

The radiopharmaceutical composition may be administered parenterally, i.e. by injection, and is most preferably an aqueous solution. Such a composition may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ascorbic acid, gentisic acid or para-aminobenzoic acid). Where the in vivo imaging agent of the invention is provided as a radiopharmaceutical composition, the method for preparation of said in vivo imaging agent may further comprise the steps required to obtain a radiopharmaceutical composition, e.g. removal of organic solvent, addition of a biocompatible buffer and any optional further ingredients. For parenteral administration, steps to ensure that the radiopharmaceutical composition is sterile and apyrogenic also need to be taken.

Methods of Use

In a yet further aspect, the present invention provides an in vivo imaging method for determining the distribution and/or the extent of PBR expression in a subject comprising:
(i) administering to said subject an in vivo imaging agent of the invention;
(ii) allowing said in vivo imaging agent to bind to PBR in said subject;
(iii) detecting by an in vivo imaging procedure signals emitted by the radioisotope of said in vivo imaging agent;
(iv) generating an image representative of the location and/or amount of said signals; and,
(v) determining the distribution and extent of PBR expression in said subject wherein said expression is directly correlated with said signals emitted by said in vivo imaging agent.

For the in vivo imaging method of the invention, the suitable and preferred embodiments of the in vivo imaging agent are as defined earlier in the specification.

"Administering" the in vivo imaging agent is preferably carried out parenterally, and most preferably intravenously. The intravenous route represents the most efficient way to deliver the in vivo imaging agent throughout the body of the subject, and therefore also across the blood-brain barrier (BBB) and into contact with PBR expressed in the central nervous system (CNS) of said subject. Furthermore, intravenous administration does not represent a substantial physical intervention or a substantial health risk. The in vivo imaging agent of the invention is preferably administered as the pharmaceutical composition of the invention, as defined herein. The in vivo imaging method of the invention can also be understood as comprising the above-defined steps (ii)-(v) carried out on a subject to whom the in vivo imaging agent of the invention has been pre-administered.

Following the administering step and preceding the detecting step, the in vivo imaging agent is allowed to bind to PBR. For example, when the subject is an intact mammal, the in vivo imaging agent will dynamically move through the mammal's body, coming into contact with various tissues therein. Once the in vivo imaging agent comes into contact with PBR, a specific interaction takes place such that clearance of the in vivo imaging agent from tissue with PBR takes longer than from tissue without, or with less PBR. A certain point in time will be reached when detection of in vivo imaging agent specifically bound to PBR is enabled as a result of the ratio between in vivo imaging agent bound to tissue with PBR versus that bound in tissue without, or with less PBR. An ideal such ratio is around 2:1.

The "detecting" step of the method of the invention involves detection of signals emitted by the radioisotope by means of a detector sensitive to said signals. This detection step can also be understood as the acquisition of signal data. Single-photon emission tomography (SPECT) and positron-emission tomography (PET) are the most suitable in vivo imaging procedures for use in the method of the invention. PET is a preferred in vivo imaging procedures for use in the method of the invention.

The "generating" step of the method of the invention is carried out by a computer which applies a reconstruction algorithm to the acquired signal data to yield a dataset. This dataset is then manipulated to generate images showing the location and/or amount of signals emitted by said radioisotope. The signals emitted directly correlate with the expression of PBR such that the "determining" step can be made by evaluating the generated image.

The "subject" of the invention can be any human or animal subject. Preferably the subject of the invention is a mammal. Most preferably, said subject is an intact mammalian body in vivo. In an especially preferred embodiment, the subject of the invention is a human. The in vivo imaging method may be used to study PBR in healthy subjects, or in subjects known or suspected to have a pathological condition associated with abnormal expression of PBR (hereunder a "PBR condition"). Preferably, said method relates to the in vivo imaging of a subject known or suspected to have a PBR condition, and therefore has utility in a method for the diagnosis of said condition.

Examples of such PBR conditions where in vivo imaging would be of use include multiple sclerosis, Rasmeussen's encephalitis, cerebral vasculitis, herpes encephalitis, AIDS-associated dementia, Parkinson's disease, corticobasal degeneration, progressive supranuclear palsy, multiple system atrophy, Huntington's Disease, amyotrophic lateral sclerosis, Alzheimer's disease, ischemic stroke, peripheral nerve injury, epilepsy, traumatic brain injury, acute stress, chronic stress, neuropathic pain, lung inflammation, chronic obstructive pulmonary disease, asthma, inflammatory bowel disease, rheumatoid arthritis, primary fibromyalgia, nerve injury, atherosclerosis, kidney inflammation, ischemia-reperfusion injury, and cancer, in particular cancer of the colon, prostate or breast. The in vivo imaging agents of the invention are particularly suited to in vivo imaging of the CNS due to their good brain uptake.

In an alternative embodiment, the in vivo imaging method of the invention may be carried out repeatedly during the course of a treatment regimen for said subject, said regimen comprising administration of a drug to combat a PBR condition. For example, the in vivo imaging method of the invention can be carried out before, during and after treatment with a drug to combat a PBR condition. In this way, the effect of said treatment can be monitored over time. Preferably for this embodiment, the in vivo imaging procedure is PET. PET has excellent sensitivity and resolution, so that even relatively small changes in a lesion can be observed over time, which is particularly advantageous for treatment monitoring.

In a further aspect, the present invention provides a method for diagnosis of a PBR condition. The method of diagnosis of the invention comprises the method of in vivo imaging as defined above, together with a further step (vi) of attributing the distribution and extent of PBR expression to a particular clinical picture, i.e. the deductive medical decision phase.

In another aspect, the present invention provides the in vivo imaging agent as defined herein for use in the method of diagnosis as defined herein.

In a yet further aspect, the present invention provides the in vivo imaging agent as defined herein for use in the manufacture of a radiopharmaceutical composition as defined herein for use in the method of diagnosis as defined herein.

The invention is now illustrated by a series of non-limiting examples.

BRIEF DESCRIPTION OF THE EXAMPLES

Example 1 describes the synthesis of precursor compound 5 and imaging agent 5.

Example 2 describes the synthesis of a non-radioactive analogue of imaging agent 5.

Example 3 describes the synthesis of precursor compound 6 and imaging agent 6.

Example 4 describes the synthesis of a non-radioactive analogue of imaging agent 6.

Example 5 describes the synthesis of precursor compound 7 and imaging agent 7.

Example 6 describes the synthesis of a non-radioactive analogue of imaging agent 7.

Example 7 describes the synthesis of precursor compound 9 and imaging agent 9.

Example 8 describes the synthesis of a non-radioactive analogue of imaging agent 9.

Example 9 describes the synthesis of precursor compound 10 and imaging agent 10.

Example 10 describes the synthesis of a non-radioactive analogue of imaging agent 10.

Example 11 describes the synthesis of precursor compound 11 and imaging agent 11.

Example 12 describes the synthesis of a non-radioactive analogue of imaging agent 11.

Example 13 describes enantiomeric separation of precursor compound 5.

Example 14 describes enantiomeric separation of non-radioactive imaging agent 5.

Example 15 describes an in vitro potency assay that was used to test the affinity for PBR.

Example 16 describes a biodistribution method that was used to examine the performance of imaging agents of the invention in vivo.

Example 17 describes the synthesis of a non-radioactive analogue of a previous tetracyclic indole imaging agent.

Example 18 describes the synthesis of a previous tetracyclic indole imaging agent.

LIST OF ABBREVIATIONS USED IN THE EXAMPLES aq aqueous
DCM dichloromethane
DMAP 4-Dimethylaminopyridine
DMF dimethylformamide
EDC 1-Ethyl-3-[3-dimethylaminopropyl]carbodiimide Hydrochloride
EOS end of synthesis
EtOAc ethyl acetate
IPA isopropyl alcohol
LC-MS liquid chromatography-mass spectrometry
NMR nuclear magnetic resonance
OBn benzyloxy
OMs mesylate
OTs tosylate
RT room temperature
TLC thin layer chromatography
Tol toluene

EXAMPLES

Example 1

Synthesis of Methanesulphonic acid 2-(4-diethylcarbamyl-5-methoxy-1,2,3,4-tetrahydro-carbazol-9-yl) ethyl ester (Precursor Compound 5) and 9-(2-[$^{18}$F]Fluoro-ethyl)-5-methoxy-2,3,4,9-tetrahydro-1H-carbazole-4-carboxylic acid diethylamide (Imaging Agent 5)

Example 1(a)

Benzyloxy acetyl chloride (1)

To benzyloxyacetic acid (10.0 g, 60.0 mmol, 8.6 mL) in dichloromethane (50 mL) was added oxalyl chloride (9.1 g, 72.0 mmol, 6.0 mL) and DMF (30.0 mg, 0.4 mmol, 32.0 µL) and stirred at RT for 3 h. There was initially a rapid evolution of gas as the reaction proceeded but evolution ceased as the reaction was complete. The dichloromethane solution was concentrated in vacuo to give a gum. This gum was treated with more oxalyl chloride (4.5 g, 35.7 mmol, 3.0 mL), dichloromethane (50 mL), and one drop of DMF. There was a rapid evolution of gas and the reaction was stirred for a further 2 h. The reaction was then concentrated in vacuo to afford 11.0 g (quantitative) of Benzyloxy acetyl chloride (1) as a gum. The structure was confirmed by $^{13}$C NMR (75 MHz, CDCl$_3$) $\delta_C$ 73.6, 74.8, 128.1, 128.4, 128.6, 130.0, and 171.9.

Example 1(b)

2-Benzyloxy-N-(2-chloro-5-metnhoxy-phenyl)acetamide (2)

Benzyloxy acetyl chloride (1) (11.0 g, 60.0 mmol) and 2-chloro-5-methoxyaniline hydrochloride (11.7 g, 60.2 mmol) in dichloromethane (100 mL) at 0° C., was stirred and triethylamine (13.0 g 126.0 mmol, 18.0 mL) added slowly over 15 min. The stirred reaction was allowed to warm to RT over 18 h. There was a heavy precipitation of triethylamine hydrochloride. The dichloromethane solution was washed with 10% aqueous potassium carbonate (50 mL), dried over magnesium sulfate and concentrated in vacuo to afford 18.9 g (quantitative) of 2-Benzyloxy-N-(2-chloro-5-methoxy-phenyl)acetamide (2) as a gum. The structure was confirmed by $^{13}$C NMR (75 MHz, CDCl$_3$): $\delta_C$ 55.6, 69.6, 73.6, 106.2, 111.1, 114.1, 127.7, 128.3, 128.6, 129.2, 134.6, 136.5, 158.9, and 167.7.

Example 1(c)

(2-Benzyloxy-ethyl)-(2-chloro-5-methoxyphenyl) amine (3)

2-Benzyloxy-N-(2-chloro-5-methoxy-phenyl)acetamide (2) (18.9 g, 62.0 mmol) in THF (100 mL) was stirred and lithium aluminum hydride (4.9 g, 130.0 mmol) was added slowly over 15 min. There was a rapid evolution of hydrogen gas as the first of the lithium aluminium hydride was added. The reaction was then heated to reflux for 4 h and allowed to stand at RT over the weekend. The reaction was then quenched by the dropwise addition of water (50 mL) to the stirred solution. There was a violent evolution of hydrogen causing the reaction mixture to reflux. The reaction was then concentrated in vacuum to a slurry. Water (200 mL) and ethyl acetate (200 mL) were added and the mixture vigorously shaken. The reaction was then filtered through celite to remove the precipitated aluminium hydroxide and the ethyl acetate solution was separated, dried over magnesium sulfate and concentrated in vacuo to afford 18.4 g (quantitative) of (2-Benzyloxy-ethyl)-(2-chloro-5-methoxyphenyl) amine (3) as a gum. The structure was confirmed by $^{13}$C NMR (75 MHz, CDCl$_3$) $\delta_C$ 43.3, 55.3, 68.2, 73.0, 98.1, 1018, 111.6, 127.6, 127.7, 128.4, 129.3, 137.9, 144.8, and 159.5.

Example 1(d)

3-Bromo-2-hydroxy-cyclohex-1-enecarboxylic acid ethyl ester (4)

Ethyl 2-oxocyclohexanecarboxylate (30 g, 176 mmol, 28 mL) was dissolved in diethyl ether (30 mL) and cooled to 0° C. under nitrogen. Bromine (28 g, 176 mmol, 9.0 mL) was added dropwise over 15 min and the reaction mixture was allowed to warm to RT over 90 min. The mixture was slowly poured into ice-cold saturated aqueous potassium carbonate (250 mL) and extracted with ethyl acetate (3×200 mL). The combined organic layers were dried over magnesium sulfate, filtered, concentrated in vacuo and dried on the vacuum line for 18 h to afford 41.4 g (94%) of 3-Bromo-2-hydroxy-1-enecarboxylic acid ethyl ester (4) as a yellow oil. The structure was confirmed by $^{13}$C NMR (75 MHz, CDCl$_3$): $\delta_C$ 14.1, 17.7, 21.8, 32.0, 60.0, 60.8, 99.7, 1663, and 172.8.

Example 1(e)

3-[2-Benzyloxy-ethyl)-(2-chloro-5-methoxy-phenyl)-amino]-2-hydroxy-cyclohex-1-ene carboxylic acid ethyl ester (5)

(2-Benzyloxy-ethyl)-(2-chloro-5-methoxyphenyl) amine (3) (10.0 g, 34.2 mmol) was stirred in dry THF (100 mL) at −40° C. under nitrogen and potassium bis(trimethylsilyl) amide (143.0 mL of a 0.5 M solution in toluene, 72.0 mmol) was added over 30 min. 3-bromo-2-hydroxycyclohex-1-enecarboxylic acid ethyl ester (4) (8.5 g, 34.2 mmol) in dry THF (10 mL) was then added and allowed to warm to RT over a period of 1.5 h. Acetic acid (10.0 g, 166 mmol, 10.0 mL) was added and concentrated in vacuo to remove the THF. Ethyl acetate (200 mL) and 10% aqueous potassium carbonate (100 mL) was added and the mixture vigorously shaken. The ethyl acetate solution was separated, dried over magnesium sulfate and concentrated in vacuo to afford 16.5 g (quantitative) of 3[(2-Benzyloxy-ethyl)-(2-chloro-5-methoxy-phenyl)-amino]-2-hydroxy-cyclohex-1-ene carboxylic acid ethyl ester (5) as a gum which was used crude in the next step. HPLC (Gemini 150×4.6 mm, 50-95% methanol/water over 20 min) of crude reaction mixture, 18.9 min (38%), 19.2 min (25%), 23.1 min (28%).

One component of the reaction was isolated $^{13}$C NMR (75 MHz, CDCl$_3$) $\delta_C$ 14.3, 20.6, 21.8, 26.4, 38.6, 43.0, 55.8, 60.5, 68.7, 73.3, 93.4, 106.3, 108.2, 119.3, 121.5, 127.5, 127.6, 128.3, 135.7, 137.0, 137.9, 155.7, and 175.0.

Example 1(f)

9-(2-Benzyloxy-ethyl)-8-chloro-5-methoxy-2,3,4,9-tetrahydro-1H-carbazole-4-carboxylic acid ethyl ester (6)

Zinc chloride (7.1 g, 52.0 mmol) was added to 3[(2-Benzyloxy-ethyl)-(2-chloro-5-methoxy-phenyl)-amino]-2-hydroxy-cyclohex-1-ene carboxylic acid ethyl ester (5) (8.0 g, 17.0 mmol) in dry diethyl ether (150 mL) under nitrogen and heated at reflux for 5.5 h.

As the reaction was refluxed a thick brown dense oil formed in the reaction. The reaction was then cooled and the supernatant diethyl ether decanted off, ethyl acetate (100 mL) was added, washed with 2 N HCl (50 mL) and with 10% aqueous potassium carbonate (50 mL). The diethyl ether layer was separated, dried over magnesium sulfate and concentrated in vacuo to afford an oil (2.0 g). The crude material was purified by silica gel chromatography eluting with petrol (A): ethyl acetate (B) (10-40% (B), 340 g, 22 CV, 150 mL/min) to afford 1.8 g of 9-(2-Benzyloxy-ethyl)-8-chloro-5-methoxy-2,3,4,9-tetrahydro-1H-carbazole-4-carboxylic acid ethyl ester (6). The thick dense brown layer was treated with ethyl acetate (100 mL) and 2 N HCl (50 mL). The ethyl acetate solution was separated, washed with 10% aqueous potassium carbonate (50 mL), dried over magnesium sulfate and concentrated in vacuo to give an oil (5.2 g). Diethyl ether (100 mL) and anhydrous zinc chloride (7.0 g) were added. The mixture was heated at reflux for a further 5 days. The ether layer was decanted off from the dark gum, was washed with 2 N HCl (50 mL), dried over magnesium sulfate and concentrated in vacuo to give a gum (2.8 g). This gum was purified by silica gel chromatography eluting with petrol (A): ethyl acetate (B) (5-35% (B), 340 g, 150 mL/min) to afford 2.1 g of 9-(2-Benzyloxy-ethyl)-8-chloro-5-methoxy-2,3,4,9-tetrahydro-1H-carbazole-4-carboxylic acid ethyl ester (6). Total material obtained was 4.1 g (50%) of 9-(2-Benzyloxy-ethyl)-8-chloro-5-methoxy-2,3,4,9-tetrahydro-1H-carbazole-4-carboxylic acid ethyl ester (6). The structure was confirmed by $^{13}$C NMR (75 MHz, CDCl$_3$): $\delta_C$ 14.4, 20.5, 22.3, 27.5, 40.2, 43.9, 55.0, 60.2, 70.7, 73.3, 100.2, 107.5, 108.4, 120.1, 122.8, 127.4, 127.5, 128.2, 132.0, 137.4, 138.1, 152.6, and 175.8.

Example 1(g)

9-(2-Benzyloxy-ethyl)-8-chloro-5-methoxy-2,3,4,9-tetrahydro-1H-carbazole-4-carboxylic acid (7)

To 9-(2-Benzyloxy-ethyl)-8-chloro-5-methoxy-2,3,4,9-tetrahydro-1H-carbazole-4-carboxylic acid ethyl ester (6) (2.0 g, 4.1 mmol) in ethanol (50 mL) was added sodium hydroxide (1.1 g, 27.1 mmol) and water (5 mL) and heated at 80° C. for 18 h. The ethanol was then removed by evaporation in vacuo and the residue partitioned between diethyl ether (50 mL) and water (50 mL). The diethyl ether layer was separated, dried over magnesium sulfate and concentrated in vacuo to give a gum (71.0 mg). The aqueous layer was acidified to pH 1 with 2N HCl (20 mL) and extracted with dichloromethane (2×100 mL). The dichloromethane layer was dried over magnesium sulfate and concentrated in vacuo to afford 1.6 g (87%) of 9-(2-Benzyloxy-ethyl)-8-chloro-5-methoxy-2,3,4,9-tetrahydro-1H-carbazole-4-carboxylic acid (7) as a foam. The structure was confirmed by $^{13}$C NMR (75 MHz; CDCl$_3$): $\delta_C$ 20.2, 22.2, 27.1, 39.7, 44.0, 55.1, 70.7, 73.3, 1006, 106.3, 108.9, 123.0, 127.4, 127.5, 128.3, 132.0, 138.0, and 152.0.

Example 1(h)

9-(2-Benzyloxy-ethyl)-8-chloro-5-methoxy-2,3,4,9-tetrahydro-1H-carbazole-4-carbonyl chloride (8)

9-(2-Benzyloxy-ethyl)-8-chloro-5-methoxy-2,3,4,9-tetrahydro-1H-carbazole-4-carboxylic acid (7) (1.5 g, 3.7 mmol) was dissolved in dichloromethane (50 mL) and oxalyl chloride (700 mg, 5.5 mmol, 470 µL) and DMF (1 drop) were added and the reaction stirred at 20° C. for 2 h. There was a moderate evolution of gas for about 30 min as the reaction proceeded. The reaction was then concentrated in vacuo to give 9-(2-Benzyloxy-ethyl)-8-chloro-5-methoxy-2,3,4,9-tetrahydro-1H-carbazole-4-carbonyl chloride (8) as a gum which was used into the next step without purification. The structure was confirmed by $^{13}$C NMR (75 MHz; CDCl$_3$): $\delta_C$ 20.8, 22.1, 26.4, 44.2, 51.8, 55.1, 70.7, 73.3, 100.7, 106.0, 108.6, 119.5, 123.4, 127.3, 127.7, 128.3, 131.9, 138.0, 138.2, 152.0. and 176.3.

Example 1(i)

9-(2-Benzyloxy-ethyl)-8-chloro-5-methoxy-2,3,4,9-tetrahydro-1H-carbazole-4-carboxylic acid diethylamide (9)

9-(2-Benzyloxy-ethyl)-8-chloro-5-methoxy-2,3,4,9-tetrahydro-1H-carbazole-4-carbonyl chloride (8) (1.6 g, 3.7 mmol) was then dissolved in dichloromethane (50 mL), cooled to 0° C., stirred and diethylamine (810 mg, 11.0 mmol, 1.1 mL) was added dropwise. The reaction was allowed to warm to room temperature over a period of 18 h. The reaction mixture was then washed with 10% aqueous potassium carbonate (50 mL), separated, dried over magnesium sulfate and concentrated in vacuo to a gum. The crude material was crystallized from diethyl ether to afford 1.2 g (71%) of 9-(2-Benzyloxy-ethyl)-8-chloro-5-methoxy-2,3,4,9-tetrahydro-1H-carbazole-4-carboxylic acid diethylamide (9) as a white crystalline solid. The structure was confirmed by $^{13}$C NMR (75 MHz; CDCl$_3$): $\delta_C$ 13.0, 14.5, 19.8, 22.2, 27.9, 36.4, 40.4, 41.9, 43.8, 55.0, 70.8, 73.3, 100.2, 108.5, 108.6, 119.9, 122.5, 127.4, 127.5, 128.3, 131.5, 137.8, 138.2, 152.4, and 174.5.

Example 1(j)

9-(2-Benzyloxy-ethyl)-5-methoxy-2,3,4,9-tetrahydro-carboxylic acid diethylamine (10)

9-(2-Benzyloxy-ethyl)-8-chloro-5-methoxy-2,3,4,9-tetrahydro-1H-carbazole-4-carboxylic acid diethylamide (9) (1.0 g, 2.1 mmol) in methanol (100 ml) was shaken with 10% palladium on charcoal (1.0 g), triethylamine (2.9 mg, 2.9 mmol, 4 µL) under an atmosphere of hydrogen gas for 18 h at 55° C. The reaction was then filtered through a pad of celite and the filtrate concentrated in vacuo to give a gum (908 mg). The gum was then taken up in dichloromethane (100 ml) and washed with 5% aqueous potassium carbonate solution (50 ml). The dichloromethane solution was then separated, dried over magnesium sulfate and concentrated in vacuo to afford a gum. The gum was then crystallised from diethyl ether (50 ml) and the crystals collected by filtration to afford 523 mg (57%) of 9-(2-Benzyloxy-ethyl)-5-methoxy-2,3,4,9-tetrahydro-1H-carbazole-4-carboxylic acid diethylamine (10). The structure was confirmed by $^{13}$C NMR (75 MHz; CDCl$_3$): $\delta_C$ 13.1, 14.6, 20.1, 22.0, 28.1, 36.4, 40.5, 42.0, 43.0, 54.7, 68.8, 73.3, 99.4, 102.4, 107.8, 116.4, 121.2, 127.6, 127.6, 128.3, 135.6, 137.8, 138.0 153.6, and 175.0.

Example 1(k)

9-(2-hydroxyethyl)-5-methoxy-2,3,4,9-tetrahydro-1H-carbazole-4-carboxylic acid diethylamine (11)

9-(2-Benzyloxy-ethyl)-5-methoxy-2,3,4,9-tetrahydro-1H-carbazole-4-carboxylic acid diethylamine (10) (1.0 g, 2.1 mmol) in methanol (50 ml) was shaken with 10% palladium on charcoal (300 mg), and hydrogen gas excess for 18 h at 55° C. The reaction was then filtered through a pad of celite and the filtrate concentrated in vacuo to give 578 mg (100%) 9-(2-hydroxyethyl)-5-methoxy-2,3,4,9-tetrahydro-1H-carbazole-4-carboxylic acid diethylamine (11) as a foam. The structure was confirmed by $^{13}$C NMR (75 MHz; CDCl$_3$): $\delta_C$ 13.0, 14.4, 20.0, 22.0, 28.0, 36.4, 40.6, 42.0, 54.7, 60.6, 99.2, 1026, 107.0, 116.7, 121.1, 136.1, 137.5, 138.0 153.5, and 175.7.

Example 1(l)

Methanesulphonic acid 2-(4-diethylcarbamyl-5-methoxy-1,2,3,4-tetrahydro-carbazol-9-yl) ethyl ester (Precursor Compound 5)

9-(2-Hydroxyethyl)-5-methoxy-2,3,4,9-tetrahydro-1H-carbazole-4-carboxylic acid diethylamine (11) (478 mg, 1.4 mmol) in dichloromethane (30 ml) was cooled to 0° C. and methanesulfonyl chloride (477 mg, 4.2 mmol, 324 µL) and triethylamine (420 mg, 4.2 mmol, 578 µL) were added and allowed to warm to RT overnight. The reaction was washed with 5% aqueous potassium carbonate solution. The layers were separated. The combined organics were dried over magnesium sulfate and concentrated in vacuo to give a gum (696 mg). The crude material was purified by silica gel chromatography eluting with petrol (A): ethyl acetate (B) (75-100% B, 22 CV, 120 g, 85 mL/min) to afford Methanesulphonic acid 2-(4-diethylcarbamyl-5-methoxy-1,2,3,4-tetrahydro-carbazol-9-yl) ethyl ester (precursor compound 5) as a gum that crystallised from diethyl ether to give 346 mg (59%) of a colourless solid. The structure was confirmed by $^{13}$C NMR (75 MHz; CDCl$_3$): $\delta_C$ 13.1, 14.5, 20.0, 21.9, 28.0, 36.3, 36.7, 40.3, 41.8, 41.9, 54.7, 68.1, 100.0, 102.0, 109.0, 116.4, 122.0 135.1, 137.3, 153.8, and 174.6.

Example 1(m)

9-(2-[$^{18}$F]Fluoro-ethyl)-5-methoxy-2,3,4,9-tetrahydro-1H-carbazole-4-carboxylic acid diethylamide (Imaging Agent 5)

[$^{18}$F]Fluoride was supplied from GE Healthcare on a GE PETrace cylcotron. Kryptofix 2.2.2 (2 mg, 5 µmol), potassium bicarbonate (0.1 mol dm$^{-3}$, 0.1 ml, 5 mg, 5 µmol) and acetonitrile (0.5 ml) was added to [$^{18}$F]F$^-$/H$_2$0 (ca. 400 MBq, 0.1-0.3 ml) in a COC reaction vessel. The mixture was dried by heating at 100° C. under a stream of nitrogen for 20-25 mins. After drying and without cooling, precursor compound 5 (0.5-1 mg, 1.2-2.4 µmol) in acetonitrile (1 ml) was added to the COC reaction vessel and heated at 100° C. for 10 mins. After cooling, the reaction mixture was removed and the COC reaction vessel rinsed with water (1.5 ml) and added to the main crude reaction.

Following this, the crude product was applied to semi-preparative HPLC: HICHROM ACE 5 C18 column (100×10 mm i.d.), particle size 5 µm; mobile phase A. Water, mobile phase B: Methanol; flow gradient: 3 ml/min; 0-1 min 40% B; 1-20 mins 40-95% B; Wavelength 254 nm; $t_R$ imaging agent 5 16 mins. The imaging agent 5 HPLC purified-peak was diluted to a volume of 10 ml with water and adsorbed on a tC18 Sep-Pak (lite) caitiidge. The cartridge was washed with water (2 ml), and eluted with anhydrous ethanol (0.5 ml) followed with Dulbecco's phosphate buffered saline (4.5 ml). Radiochemical yield 30±7% (n=4) non-decay corrected, time 90-120 mins, radiochemical purity ≥99%.

Analytical-HPLC: Phenomenex Luna C18 column (150× 4.6 mm i.d.), particle size 5 µm; mobile phase A. Water, mobile phase B: Methanol; flow gradient: 1 ml/min; 0-1 min 40% B; 1-20 mins 40-95% B; Wavelength 230 nm; $t_R$ imaging agent 5 16 mins. FIG. 1 shows co-elution of imaging agent 5 and non-radioactive imaging agent 5.

Example 2

Synthesis of 9-(2-Fluoro-ethyl)-5-methoxy-2,3,4,9-tetrahydro-1H-carbazole-4-carboxylic acid diethylamide (Non-Radioactive Imaging Agent 5)

Example 2(a)

Fluoroethyl Tosylate (12)

2-Fluoroethanol (640 mg, 10 mmol, 0.6 mL) was dissolved in pyridine (10 mL) under nitrogen. The solution was stirred at 0° C. and tosyl chloride (4.2 g, 21.8 mmol) added portionwise to the solution over a period of 30 min, keeping the temperature below 5° C. The reaction was stirred at 0° C. for 3 h. Ice was slowly added followed by water (20 mL). The reaction mixture was extracted into ethyl acetate and washed with water. Excess pyridine was removed by washing with 1 N HCl solution until the aqueous layer became acidic. Excess tosyl chloride was removed by washing with 1 M aqueous sodium carbonate. The organic layer was washed with brine, dried over magnesium sulfate and concentrated in vacuo to give 2.1 g (98%) of fluoroethyl tosylate (12) as a colourless oil. The structure was confirmed by $^{13}$C NMR (75 MHz, CDCl$_3$): $\delta_C$ 21.6 (C$\underline{C}$H$_3$), 68.5 (d, J$_{CF}$=173 Hz, O$\underline{C}$H$_2$CH$_2$F), 80.6 (d, J$_{CF}$=173 Hz, OCH$_2$$\underline{C}$H$_2$F), 128.0, 129.9, 132.6, and 145.1.

Example 2(b)

2-chloro-5-methoxy phenyl)(2-fluoroethyl) amine (13)

2-Chloro-5-methoxyaniline hydrochloride (5.0 g, 26.0 mmol) was dissolved in DMF (50 mL) and sodium hydride (2.3 g, 60% in oil, 57.0 mmol) was added. The reaction was stirred for 30 minutes at RT under nitrogen. Fluoroethyl tosylate (12) (6.7 g, 31.0 mmol) in DMF (5 mL) was added dropwise and the reaction was stirred at RT for 2 h. The reaction was then heated at 100° C. for 18 h. The reaction was allowed to cool and the solvent was removed under reduced pressure. The residue was dissolved in ethyl acetate (100 mL) and washed with water (2×100 mL). The organics were collected, dried over magnesium sulfate and concentrated in vacuo to give a brown oil which was purified by silica gel chromatography eluting with petrol (A): ethyl acetate (B) (5-30% (B), 330 g, 18.1 CV, 120 mL/min) to afford 1.3 g (25%) of 2-chloro-5-methoxy-phenyl) (2-fluoroethyl) amine (13) as a yellow oil. The structure was continued by $^{13}$C NMR (75 MHz; CDCl$_3$): $\delta_C$ 43.8 (d, J$_{CF}$=23 Hz), 55.3, 82.0 (d, J$_{CF}$=165 Hz), 98.1, 102.2, 111.6, 129.5, 144.1, and 159.5.

Example 2(c)

3-[(2-Chloro-5-methoxy-phenyl)-(2-fluoroethyl) amino]-2-hydroxy-cyclohexyl-1-enecarboxylic acid ethyl ester (14)

A solution of 2-chloro-5-methoxy-phenyl) (2-fluoroethyl) amine (13) (6.1 g, 30.0 mmol) in THF (170 mL) was cooled to −40° C. Potassium bis(trimethylsilyl)amide (126.0 mL of a 0.5 M solution in toluene, 63.0 mmol) was added dropwise and the reaction stirred for 30 min at −40° C.) 3-Bromo-2-hydroxy-cyclohex-1-enecarboxylic acid ethyl ester (4; prepared according to Example 1(d)) (7.4 g, 30.0 mmol) in THF (30 mL) was added dropwise at −40° C. The cooling bath was removed and the reaction was stirred at RT for 4 h. The reaction was quenched with brine (300 mL) and extracted into ethyl acetate (2×400 mL), dried over magnesium sulfate and concentrated in vacuo to give 12.0 g (quantitative) of 3-[(2-Chloro-5-methoxy-phenyl)-(2-fluoroethyl)amino]-2-hydroxy-cyclohexyl-1-enecarboxylic acid ethyl ester (14) as a brown oil which was used crude in the next step. The structure as a mixture of isomers was confirmed by $^1$H NMR (300 MHz, CDCl$_3$): $\delta_H$ 1.08 (0.8H, t, J=9 Hz, CO$_2$CH$_2$CH$_3$), 1.22-1.33 (2.2 H, m, CO$_2$CH$_2$CH$_3$), 1.40-2.60 (7H, m, 4-, 5-, and 6-CH$_2$, CHN), 3.20-4.50 (10H, m, NCH$_2$CH$_2$F, NCH$_2$CH$_2$F, OCH$_3$, CHCO$_2$CH$_2$CH$_3$), 6.50-6.70 (1H, m, CHC(OCH$_3$)C HCH), 6.95 (0.5H, dd, J=3 and 6 Hz, CHC(OCH$_3$)CHCH), 7.08 (0.5H, d, J=3 Hz, CHC(OCH$_3$)CHCH), and 7.20-7.30 (1H, m, CHC(OCH$_3$)CHCH).

Example 2(d)

8-chloro-9-(2-Fluoroethyl)-5-methoxy-2,3,4,9-tetrahydro-1H-carbazole-4-carboxylic acid ethyl ester (15)

Synthesis of 8-Chloro-9-(2-fluoro-ethyl)-5-methoxy-2,3,4,9-tetrahydro-1H-carbazole-4-carboxylic acid ethyl ester (15) was initially attempted using the conditions described in WO 2003/014082. A solution of 2-chloro-5-methoxy-phenyl) (2-fluoroethyl) amine (13; prepared according to Example 2(b)) (600 mg, 3.8 mmol) in dry THF (20 mL) was cooled in an ice bath and treated with potassium bis(trimethyl silyl) amide (16 mL of a 0.5 M solution in toluene, 8.0 mmol). After 30 minutes 3-Bromo-2-hydroxy-cyclohex-1-enecarboxylic acid ethyl ester (4; prepared according to Example 1(d)) (1.04 g, 4.2 mmol) in THF (4 mL) was added and the reaction was allowed to warm to RT over 2 hours. The reaction was quenched with saturated ammonium chloride solution and extracted twice with ether. The extracts were washed with water, brine, dried and concentrated in vacuo. The crude material was purified by silica gel chromatography eluting with petrol (A) and ethyl acetate (B) (2.5-50% B, 50 g, 25 CV, 40 mL/min). The main spot was a mixture of three compounds. This mixture was refluxed in toluene (20 mL) with dry zinc chloride (1.7 g, 12.6 mmol) overnight. The reaction was concentrated in vacuo and the residue was partitioned between 1N HCL (25 mL) and ethyl acetate (25 mL) and then extracted once more with ethyl acetate. The organic layers were washed with water and brine, dried and concentrated in vacuo to afford a brown oil. $^1$H NMR indicated that it was a mixture of several compounds. TLC on silica in a range of solvents could not separate this mixture into separate spots. Comparison of the $^1$H NMR of the mixture with an authentic sample indicated that the mixture contained an estimated 25% of 8-Chloro-9-(2-fluoro-ethyl)-5-methoxy-2,3,4,9-tetrahydro-1H-carbazole-4-carboxylic acid ethyl ester (15).

A modified method was then carried out. 3-[(2-Chloro-5-methoxy-phenyl)-(2-fluoroethyl)amino]-2-hydroxy-cyclohexyl-1-enecarboxylic acid ethyl ester (14) (12.2 g, 30.0 mmol) was dissolved in diethyl ether (250 mL) and zinc chloride (16.4 g, 120.0 mmol) was added. The reaction was heated at reflux for 16 h. Ethyl acetate (500 mL) was added to dissolve everything and was washed with 2N HCl (200 mL), water (200 mL), 10% aqueous potassium carbonate (200 mL), dried over magnesium sulfate and concentrated in vacuo. The crude material was purified by silica gel chromatography eluting with petrol (A): ethyl acetate (B) (5-20% B, 12 CV, 10 g, 100 mL/min) to afford 5.3 g (50% over 2 steps) of 8-chloro-9-(2-Fluoroethyl)-5-methoxy-2,3,4,9-tetrahydro-1H-carbazole-4-carboxylic acid ethyl ester (15) as a yellow solid. The structure was confirmed by $^{13}$C NMR (75 MHz, CDCl$_3$): $\delta_C$ 14.4, 20.4, 22.2, 27.4, 40.1, 44.2 (d, J$_{CF}$=23 Hz), 55.1, 60.2, 83.9 (d, J$_{CF}$=173 Hz), 100.6, 107.9, 108.2, 119.8, 123.1, 131.9, 137.2, 152.7, and 175.7.

Example 2(e)

9-(2-Fluoroethyl)-5-methoxy-2,3,4,9-tetrahydro-1H-carbazole-4-carboxylic acid ethyl ester (16)

8-chloro-9-(2-Fluoroethyl)-5-methoxy-2,3,4,9-tetrahydro-1H-carbazole-4-carboxylic acid ethyl ester (15) (5.3 g, 15.0 mmol) was dissolved in methanol (180 mL) and triethylamine (1.8 g, 18.0 mmol, 2.5 mL) and 10% Pd/C (2 g in methanol (20 mL)) were added. The mixture was placed on the Parr hydrogenator and shaken for 18 h under a hydrogen atmosphere. The reaction was filtered through a pad of celite, washed with methanol and the solvent was removed in vacuo. The residue was dissolved in ethyl acetate (300 mL) and washed with 10% aqueous potassium carbonate (200 mL), dried over magnesium sulfate and concentrated in vacuo to give 4.2 g (88%) of 9-(2-Fluoroethyl)-5-methoxy-2,3,4,9-tetrahydro-1H-carbazole-4-carboxylic acid ethyl ester (16) as a light brown solid. The structure was confirmed by $^{13}$C NMR (75 MHz, CDCl$_3$): $\delta_C$ 14.3, 20.6, 21.8, 27.6, 40.3, 43.3 (d, J$_{CF}$=23 Hz), 54.9, 60.1, 82.0 (d, J$_{CF}$=165 Hz), 99.8, 102.1, 107.3, 117.2, 121.8, 134.9, 137.6, 153.8, and 176.0.

HPLC (Gemini 150×4.6 mm, 50-95% methanol/water over 20 min) 13.6 min (94%).

Example 2(f)

9-(2-Fluoroethyl)-5-methoxy-2,3,4,9-tetrahydro-1H-carbazole-4-carboxylic acid (17)

8-chloro-9-(2-Fluoroethyl)-5-methoxy-2,3,4,9-tetrahydro-1H-carbazole-4-carboxylic acid ethyl ester (16) (380 mg, 1.2 mmol) was dissolved in ethanol (4 mL). A solution of sodium hydroxide (580 mg, 14.5 mmol) dissolved in 6 mL of water, was added. The reaction mixture was heated to reflux overnight. The solvent was removed in vacuo and the crude mixture diluted with water, acidified with 2 N HCl until acidic, and washed with dichloromethane. The organics were combined and dried over magnesium sulfate and concentrated in vacuo to give 347 mg (quantitative) of 9-(2-Fluoroethyl)-5-methoxy-2,3,4,9-tetrahydro-1H-carbazole-4-carboxylic acid (17) as an off white solid which was used crude into the next step. The structure was confirmed by $^{13}$C NMR (75 MHz; CDCl$_3$): $\delta_C$ 20.4, 21.9, 27.2, 39.9, 43.3 (d, J$_{CF}$=23 Hz), 55.1, 81.9 (d, J$_{CF}$=173 Hz), 100.3, 102.8, 106.2, 117.1, 122.2, 135.6, 137.8, 153.3, and 180.8.

Example 2(g)

9-(2-Fluoroethyl)-5-methoxy-2,3,4,9-tetrahydro-1H-carbazole-4-carbonyl chloride (18)

A solution of 9-(2-Fluoroethyl)-5-methoxy-2,3,4,9-tetrahydro-1H-carbazole-4-carboxylic acid (17) (347 mg, 1.2 mmol) in dry dichloromethane (2 mL) was stirred under nitrogen. Oxalyl chloride (453 mg, 3.6 mmol, 300 μL) was added followed by a drop of DMF The reaction mixture was stirred at RT under nitrogen for 2 h then evaporated in vacuo to give 371 mg (quantitative) of 9-(2-fluoroethyl)-5-methoxy-2,3,4,9-tetrahydro-1H-carbazole-4-carbonyl chloride as a gum which was used in the next step without purification. The structure was confirmed by $^{13}$C NMR (75 MHz, CDCl$_3$): $\delta_C$ 20.2, 21.7, 26.4, 43.3 (d, $J_{CF}$=23 Hz), 54.9, 80.5, 83.1, 100.2, 102.2, 105.8, 116.7, 122.4, 135.5, 137.4, 153.5, and 176.6.

Example 2(h)

9-(2-Fluoroethyl)-5-methoxy-2,3,4,9-tetrahydro-1H-carbazole-4-carboxylic acid diethyl amide (Non-Radioactive Imaging Agent 5)

9-(2-fluoroethyl)-5-methoxy-2,3,4,9-tetrahydro-1H-carbazole-4-carbonyl chloride (18) (371 mg, 1.2 mmol) was dissolved in dichloromethane (2 mL) and cooled to 0° C. diethylamine (177 mg, 2.4 mmol, 250 µL) was then added and the reaction was stirred overnight at RT. The reaction was quenched with 10% aqueous potassium carbonate (2 mL). The dichloromethane layer was collected through a phase separator then concentrated in vacuo. The crude material was purified by silica gel chromatography eluting with petrol (A): ethyl acetate (B) (50-100% (B), 50 g, 35.2 CV, 40 mL/min) to afford a pale yellow solid. The solid was next triturated with a minimum amount of diethyl ether to afford 240 mg (58%) of 9-(2-Fluoroethyl)-5-methoxy-2,3,4,9-tetrahydro-1H-carbazole-4-carboxylic acid diethyl amide (non-radioactive imaging agent 5). The structure was confirmed by $^{13}$C NMR (75 MHz, CDCl$_3$): $\delta_C$ 13.0, 14.6, 19.9, 21.9, 28.0, 36.3, 40.5, 41.9, 43.1 (d, $J_{cp}$=23 Hz), 54.7, 82.0 (d, $J_{CF}$=173 Hz), 99.7, 102.1, 108.3, 117.0, 121.5, 135.3, 137.4, 153.3, and 174.8.

Example 3

Synthesis of Methanesulfonic acid 2-[4-(piperidine-1-carbonyl)-1,2,3,4-tetrahydro-carbazol-9-yl]-ethyl ester (Precursor Compound 6) and [9-(2-[$^{18}$F]-Fluoro-ethyl)-2,3,4,9-tetrahydro-1H-carbazol-4-yl]-piperidin-1-yl-methanone (Imaging Agent 6)

Example 3(a)

2-(Piperidine-1-carbonyl)-cyclohexanone (19)

Ethyl 2-oxocyclohexane-carboxylate (5.3 g, 31 mmol, 5.0 mL) DMAP (1.05 g, 9.4 mmol) and piperidine (5.3 g, 63 mmol, 6.2 mL) in toluene (100 mL) were heated at reflux for 4 days. The reaction was allowed to cool and the reaction was concentrated in vacuo. The crude material was purified by silica gel chromatography eluting with petrol (A) and ethyl acetate (B) (20-80% (B), 100 g, 8 CV, 85 mL/min) to afford 6.26 g (96%) of 2-(piperidine-1-carbonyl)-cyclohexanone (19) as a white solid. The structure was confirmed by $^{13}$C NMR (75 MHz, CDCl$_3$) $\delta_C$ 23.5, 24.5, 25.5, 26.2, 27.1, 30.4, 41.9, 42.9, 46.8, 54.2, 167.6, 207.6.

Example 3(b)

2-Bromo-6-(piperidine-1-carbonyl)-cyclohexanone (20)

2-(piperidine-1-carbonyl)-cyclohexanone (19) (4.0 g, 19 mmol) was dissolved in diethyl ether (5 mL) and cooled to 0° C. under N$_2$. Bromine (5.9 g, 19 mmol, 1.0 mL) was added dropwise over 15 min and the reaction mixture was allowed to warm to room temperature over 90 min. The solid was collected by filtration to give 5.86 g (quantitative) of 2-bromo-6-(piperidine-1-carbonyl)-cyclohexanone (20) as a white solid which was used in the next step without purification. The structure was confirmed by $^{13}$C NMR (75 MHz, DMSO-d$_6$) $\delta_C$ 17.3, 24.2, 25.3, 25.8, 32.5, 44.0, 51.6, 1083, 145.5, 167.8.

Example 3(c)

(2-Benzyloxy-ethyl)-phenyl-amine (21)

In a round bottom flask aniline (2.0 g, 21.5 mmol, 2.0 mL), 2,6-lutidine (2.30 g, 21.5 mmol) and benzyl 2-bromoethyl ether (4.6 g, 21.5 mmol, 3.4 mL) were combined in DMF (10 mL) and stirred at 100° C. overnight. The reaction was allowed to cool and then diluted with ethyl acetate (50 mL). This was washed with water (3×20 nit) and the organics were dried and concentrated in vacuo. The crude material was purified by silica gel chromatography eluting with petrol (A) and ethyl acetate (B) (0-50% B, 100 g, 19.5 CV, 85 mL/min) to afford 2.22 g (37%) of (2-benzyloxy-ethyl)-phenyl-amine (21) as a yellow oil. The structure was confirmed by $^{13}$C NMR (75 MHz, CDCl$_3$) $\delta_C$ 43.6, 68.6, 73.2, 113.1, 117.5, 127.5, 127.7, 128.4, 129.1, 138.2, 148.1

Example 3(d)

[9-(2-Benzyloxy-ethyl)-2,3,4,9-tetrahydro-1H-carbazol-4-yl]-piperidin-1-yl-methanone (22)

A mixture of 2-bromo-6-(piperidine-1-carbonyl)-cyclohexanone (20) (1.5 g, 5.2 mmol) and (2-benzyloxy-ethyl)-phenyl-amine (21) (3.2 g, 10.4 mmol) was stirred under N$_2$ at 50° C. for 3 h and the reaction turned brown. The resulting mixture was dissolved in propan-2-ol (5 mL) and dry zinc chloride (2.13 g, 15.6 mmol) was added. The mixture was heated to reflux under N$_2$ for 16 h and then concentrated in vacuo. The residue was dissolved in ethyl acetate (100 mL) and washed with 2 N HCl (30 mL), water (2×30 mL) and aqueous potassium carbonate solution (2×30 mL) then dried and concentrated in vacuo. The crude material was purified by SCX cartridge and then silica gel chromatography eluting with petrol (A) and ethyl acetate (B) (30-100% B, 12 g, 41 CV, 30 mL/min) to afford 600 mg (27%) of [9-(2-benzyloxy-ethyl)-2,3,4,9-tetrahydro-1H-carbazol-4-yl]-piperidin-1-yl-methanone (22) as an oil. The structure was confirmed by $^{13}$C NMR (75 MHz, CDCl$_3$) $\delta_C$ 21.5, 21.7, 24.5, 25.7, 26.3, 273, 37.7, 42.8, 43.1, 46.7, 60.2, 68.7, 73.1, 108.2, 108.7, 117.8, 118.9, 120.5, 126.4, 127.3, 127.4, 128.1, 136.2, 137.8, 172.9.

Example 3(e)

[9-(2-Hydroxy-ethyl)-2,3,4,9-tetrahydro-1H-carbazol-4-yl]-piperidin-1-yl-methanone (23)

To a solution of [9-(2-benzyloxy-ethyl)-2,3,4,9-tetrahydro-1H-carbazol-4-yl]-piperidin-1-yl-methanone (22) (600 mg, 1.4 mmol) in methanol (15 mL) was added a slurry of Pd/C (200 mg) in methanol (10 mL). The mixture was placed on the Parr hydrogenator and shaken for 24 h under a hydrogen atmosphere. The reaction was filtered through a pad of celite, washed with methanol and concentrated in vacuo. The crude material was triturated to afford 332 mg (71%) of [9-(2-hydroxy-ethyl)-2,3,4,9-tetrahydro-1H-carbazol-4-yl]-piperidin-1-yl-methanone (23) as a white solid. The structure was confirmed by $^{13}$C NMR (75 MHz, CDCl$_3$): $\delta_C$ 21.2, 21.9, 24.7, 27.4, 36.4, 43.4, 45.0, 47.0, 60.9, 107.8, 109.0, 117.7, 119.0, 120.7, 126.6, 136.2, 137.2, 173.5

Example 3(f)

Methanesulfonic acid 2-[4-(piperidine-1-carbonyl)-1,2,3,4-tetrahydro-carbazol-9-yl]-ethyl ester (Precursor Compound 6)

To a solution of [9-(2-hydroxy-ethyl)-2,3,4,9-tetrahydro-1H-carbazol-4-yl]-piperidin-1-yl-methanone (23) (260 mg, 0.8 mmol) in dichloromethane (15 mL) was added pyridine (633 mg, 8.0 mmol, 0.65 mL) The reaction was cooled to 0° C. and methanesulfonyl chloride (458 mg, 4.0 mmol, 0.31 mL) was added. The reaction was allowed to warm to room temperature overnight. The mixture was washed with 2 N HCl (2×50 mL) and water (2×50 mL), dried and concentrated in vacuo. The crude material was triturated with diethyl ether to afford 263 mg (82%) of methanesulfonic acid 2-[4-(piperidine-1-carbonyl)-1,2,3,4-tetrahydro-carbazol-9-yl]-ethyl ester (precursor compound 6) as a white solid. The structure was confirmed by $^{13}$C NMR (75 MHz, CDCl$_3$) $\delta_C$ 21.4, 21.8, 24.7, 25.9, 26.9, 27.4, 36.6, 36.8, 41.7, 43.3, 47.0, 67.9, 108.5, 109.5, 118.4, 119.7, 121.3, 126.9, 136.2, 172.7.

Example 3(g)

[9-(2-[$^{18}$F]Fluoro-ethyl)-2,3,4,9-tetrahydro-1H-carbazol-4-yl]-piperidin-1-yl-methanone (Imaging Agent 6)

Labelling of precursor compound 6 with $^{18}$F was carried out as described in Example 1(f).

Semi-preparative HPLC: HICHROM ACE 5 C18 column (100×10 mm i.d.), particle size 5 μm; mobile phase A. Water, mobile phase B: Methanol; flow gradient: 3 ml/min; 0-1 min 50% B; 1-20 mins 50-95% B; Wavelength 254 nm; $t_R$ imaging agent 6, 17 mins.

Figure 2:
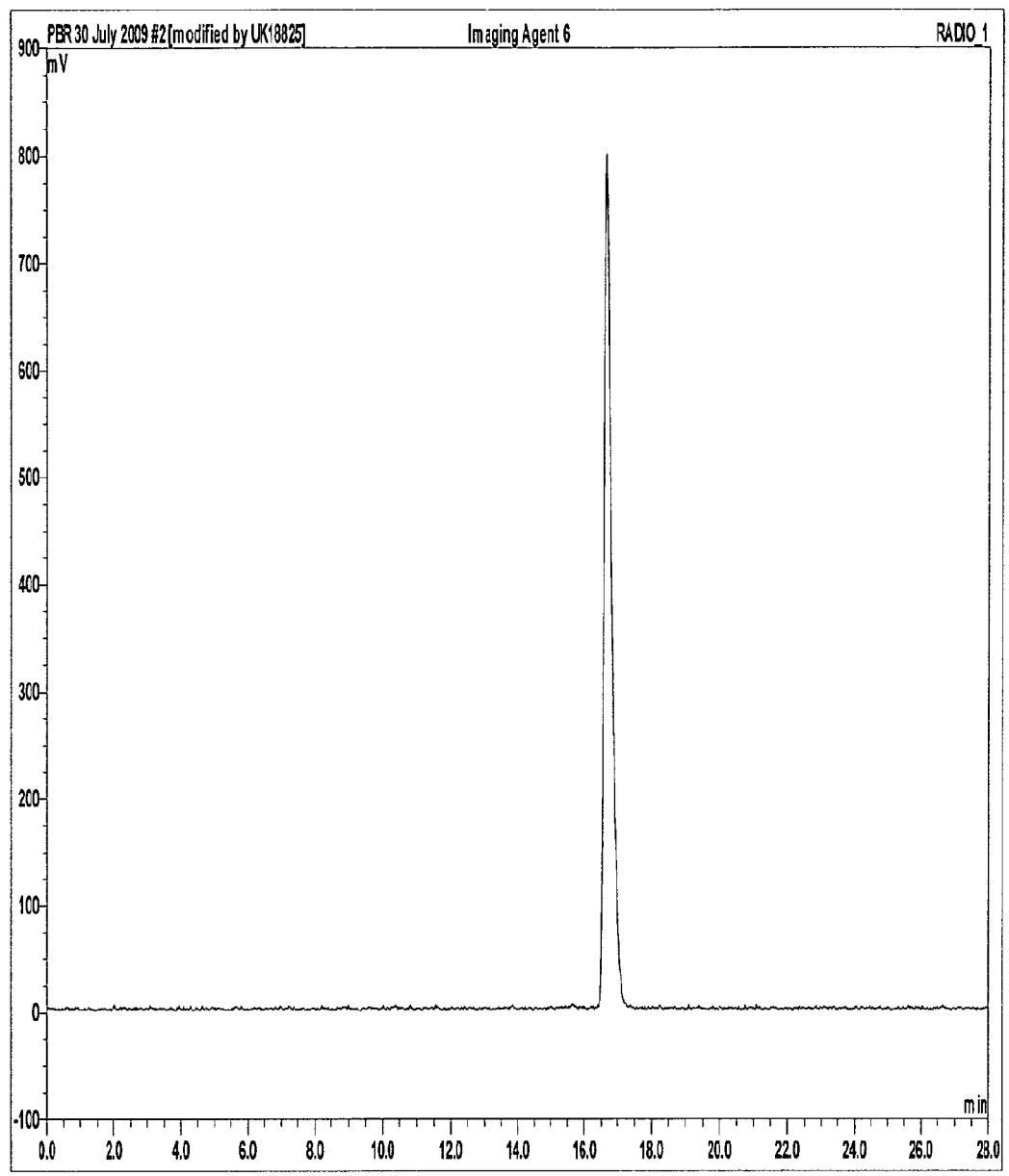
FIG. 2 shows co-elution of imaging agent 6 and non-radioactive imaging agent 6.
Figure 2:
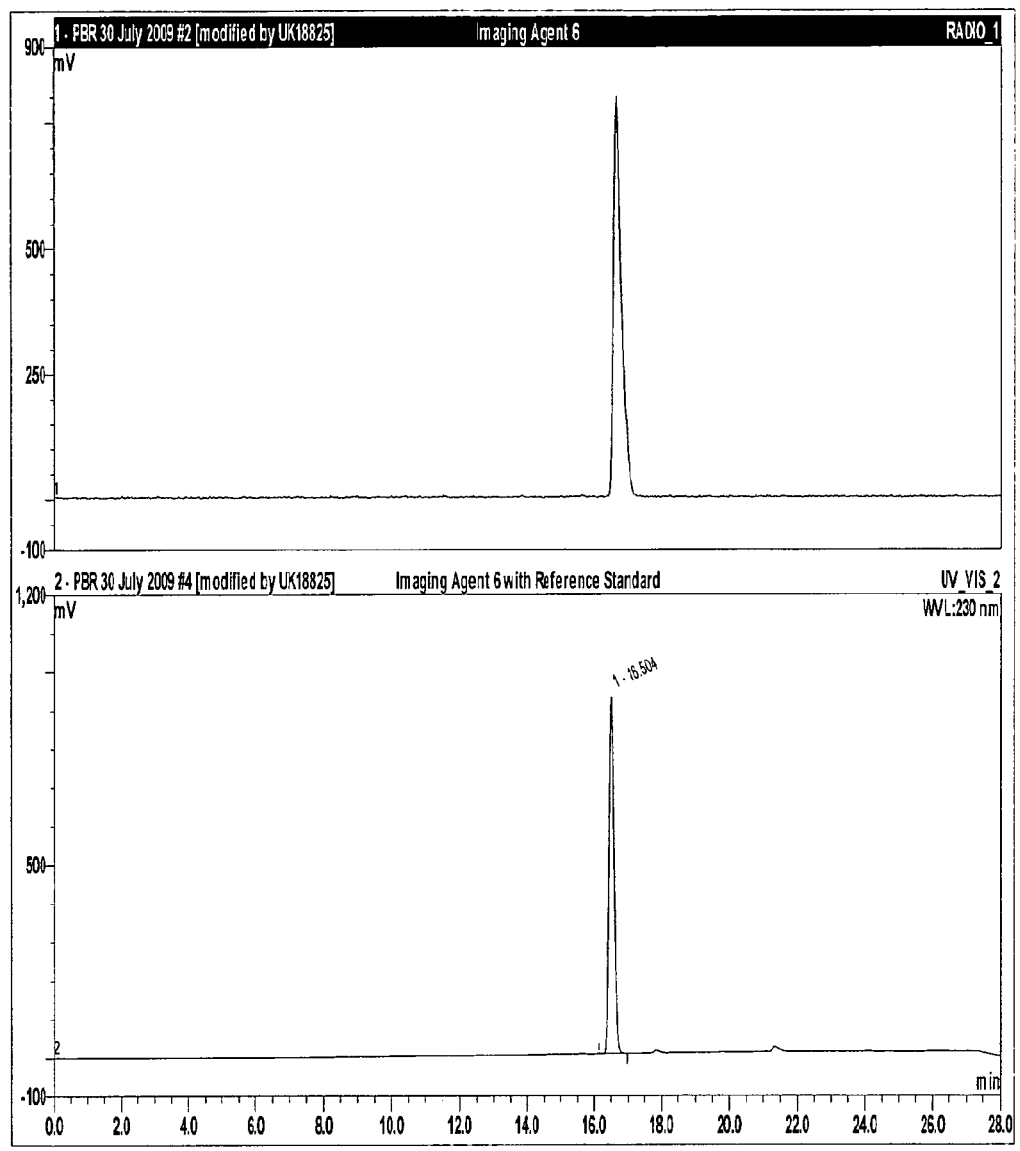

Analytical-HPLC: Phenomenex Luna C18 column (150× 4.6 mm i.d.), particle size 5 μm; mobile phase A. Water, mobile phase B: Methanol; flow gradient: 1 ml/min; 0-1 min 50% B; 1-20 mins 50-95% B; Wavelength 230 nm; $t_R$ imaging agent 6 16 mins Radiochemical yield 23±2% (n=3) non-decay corrected, time 90-120 mins, radiochemical purity ≥99%. FIG. 2 shows co-elution of imaging agent 6 and non-radioactive imaging agent 6.

Example 4

Synthesis of [9-(2-Fluoro-ethyl)-2,3,4,9-tetrahydro-1H-carbazol-4-yl]-piperidin-1-yl-methanone (non-radioactive analogue of imaging agent 6)

Example 4(a)

(2-Fluoro-ethyl)-phenyl-amine (24)

In a round bottom flask aniline (0.5 g, 5.4 mmol), 2,6-lutidine (0.58 g, 5.4 mmol) and 2-fluoroethyl tosylate (12; prepared according to Example 2(a)) (1.17 g, 5.4 mmol) were combined in DMF (2.5 mL) and stirred at 100° C. overnight. The reaction was allowed to cool and then diluted with ethyl acetate (50 mL) This was washed with water (3×20 mL) and the organics were dried and concentrated in vacuo. The crude material was purified by silica gel chromatography eluting with petrol (A) and ethyl acetate (B) (100 g, 0-100% B, 18 CV, 85 mL/min) to give 435 mg (60%) of (2-fluoro-ethyl)-phenyl-amine (24) as a yellow oil. The structure was confirmed by $^1$H NMR (300 MHz, CDCl$_3$) $\delta_H$ 3.41 (1H, t, J=3 Hz, NCH$_2$CH$_2$F), 3.50 (1H, t, J=3 Hz, NCH$_2$CH$_2$F), 3.93 (1H, s, br), 4.54 (1H, t, J=3 Hz, NCH$_2$CH$_2$F), 4.71 (1H, t, J=3 Hz, NCH$_2$CH$_2$F), 6.65-6.82 (3H, m, 2×NCCH, NCCHCHCH), 7.14-7.28 (2H, m, 2×NCCHCHCH).

Example 4(b)

[9-(2-Fluoro-ethyl)-2,3,4,9-tetrahydro-1H-carbazol-4-yl]-piperidin-1-yl-methanone (Non-Radioactive Imaging Agent 6)

A mixture of 2-bromo-6-(piperidine-1-carbonyl)-cyclohexanone (20; prepared according to example 3(b)) (500 mg, 1.7 mmol) and (2-fluoro-ethyl)-phenyl-amine (24) (890 mg, 3.5 mmol) was stirred under N$_2$ at 50° C. for 3 h and the reaction turned brown. The resulting mixture was dissolved in propan-2-ol (2 mL) and dry zinc chloride (682 mg, 5 mmol) was added. The mixture was heated to reflux under N$_2$ for 16 h and then concentrated in vacuo. The residue was dissolved in ethyl acetate (50 mL) and washed with 2 N HCl (20 mL), water (2×20 mL) and aqueous potassium carbonate solution (2×20 mL) then dried and concentrated in vacuo. The crude material was triturated with diethyl ether to afford 151 mg (27%) of [9-(2-fluoro-ethyl)-2,3,4,9-tetrahydro-1H-carbazol-4-yl]-piperidin-1-yl-methanone (non-radioactive imaging agent 6) as a white solid. The structure was confirmed by $^{13}$C NMR (75 MHz, CDCl$_3$) $\delta_C$ 21.6, 21.8, 24.7, 26.5, 26.9, 27.4, 37.3, 43.1 (d, J$_{CF}$=45 Hz), 47.0, 82.1 (d, J$_{CF}$=173 Hz), 108.5, 108.9, 118.6, 119.4, 121.0, 126.8, 136.2, 172.7.

Example 5

Synthesis of Methanesulfonic acid 2-[4-(benzyl-methyl-carbamoyl)-1,2,3,4-tetrahydro-carbazol-9-yl]-ethyl ester (Precursor Compound 7) and 9-[$^{18}$F]fluoro-ethyl)-2,3,4,9-tetrahydro-1H-carbazole-4-carboxylic acid benzyl-methyl-amide (Imaging Agent 7)

Example 5(a)

9-(2-Benzyloxy-ethyl)-2,3,4,9-tetrahydro-1H-carbazole-4-carboxylic acid ethyl ester (25)

A mixture of (2-benzyloxy-ethyl)-phenyl-amine (21, prepared according to Example 3(c)) (8.0 g, 26 mmol) and 3-bromo-2-hydroxy-cyclohex-1-enecarboxylic acid ethyl ester (4; prepared according to Example 1(d)) (3.2 g, 13 mmol) was stirred under N$_2$ at 50° C. for 3 h and the reaction turned brown. The resulting mixture was dissolved in propan-2-ol (30 mL) and dry zinc chloride (10.6 g, 78 mmol) was added. The mixture was heated to reflux under N$_2$ for 16 h and then concentrated in vacuo. The residue was dissolved in ethyl acetate (300 mL) and washed with 2 N HCl (100 mL), water (2×100 mL) and aqueous potassium carbonate solution (2×100 mL) then dried and concentrated in vacuo. The crude material was purified by silica gel chromatography eluting with petrol (A) and ethyl acetate (B) (2.5-40% B, 17 CV, 330 g, 100 mL/min) to give 3.49 g (72%) of 9-(2-benzyloxy-ethyl)-2,3,4,9-tetrahydro-1H-carbazole-4-carboxylic acid ethyl ester (25) as an oil. The structure was confirmed by $^{13}$C NMR (75 MHz, CDCl$_3$) $\delta_C$ 14.2, 20.5, 21.8, 26.5, 38.6, 42.9, 60.4, 68.7, 73.2, 106.4, 108.8, 118.7, 120.7, 127.4, 127.5, 128.3, 136.2, 136.9, 137.8, 175.0.

Example 5(b)

9-(2-Benzyloxy-ethyl)-2,3,4,9-tetrahydro-1H-carbazole-4-carboxylic acid (26)

9-(2-Benzyloxy-ethyl)-2,3,4,9-tetrahydro-1H-carbazole-4-carboxylic acid ethyl ester (25) (35 g, 9.3 mmol) was dissolved in ethanol (9 mL) and then NaOH (1.56 g) in water (15 mL) was added. The reaction was heated at reflux for 2 h. The reaction was concentrated in vacuo and the residue diluted with water and washed with dichloromethane (2×150 mL). The aqueous layer was added drop wise to 2 N HCl (150 mL) and then extracted into dichloromethane (3×150 mL). The organics were dried and concentrated in vacuo to afford 2.48 g (92%) of 9-(2-benzyloxy-ethyl)-2,3,4,9-tetrahydro-1H-carbazole-4-carboxylic acid (26) as a yellow solid which was used in the next step without purification. The structure was confirmed by $^{13}$C NMR (75 MHz, CDCl$_3$) $\delta_C$ 20.4, 21.8, 26.4, 38.3, 42.9, 68.7, 73.3, 105.7, 108.8, 118.7, 119.3, 102.9, 127.4, 127.6, 128.3, 136.2, 137.1, 137.8, 108.9.

Example 5(c)

9-(2-Benzyloxy-ethyl)-2,3,4,9-tetrahydro-1H-carbazole-4-carboxylic acid benzyl-methyl-amide (27)

9-(2-Benzyloxy-ethyl)-2,3,4,9-tetrahydro-1H-carbazole-4-carboxylic acid (26) (600 mg, 1.7 mmol) was dissolved in dry DCM (8 mL) under nitrogen and oxalyl chloride (393 mg, 3.1 mmol, 0.26 mL) was added. The reaction was stirred at room temperature for 3 h and there was vigorous evolution of gas. The reaction was concentrated in vacuo and then redissolved in dichloromethane (8 mL) and cooled to 0° C. and N-benzylmethylamine (412 mg, 3.4 mmol, 0.44 mL) was added. The reaction was warmed to room temperature overnight. The reaction was washed with 5% aqueous potassium carbonate solution, dried and concentrated in vacuo to afford a brown oil. The crude material was purified by silica gel chromatography eluting with petrol (A) and ethyl acetate (B) (30% B, 10 g) to afford 246 mg (64%) of 9-(2-benzyloxy-ethyl)-2,3,4,9-tetrahydro-1H-carbazole-4-carboxylic acid benzyl-methyl-amide (27) as a yellow oil. The structure was confirmed by $^1$H NMR (CDCl$_3$) $\delta_H$ 1.60-2.30 (4H, m, CHCH$_2$CH$_2$CH$_2$), 2.70-2.90 (2H, m, CHCH$_2$CH$_2$CH$_2$), 3.10 (1.5H, s, N(CH$_3$)CH$_2$Ph), 3.13 (1.5H, s, N(CH$_3$)CH$_2$Ph), 3.73 (2H, t, J=6 Hz, NCH$_2$CH$_2$O), 4.10-4.30 (3H, m, NCH$_2$CH$_2$O, CHCH$_2$CH$_2$CH$_2$), 4.42 (1H, s, OCH$_2$Ph), 4.44 (1H, s, OCH$_2$Ph), 4.80 (1H, s, N(CH$_3$)CH$_2$Ph), 4.81 (1H, s, N(CH$_3$)CH$_2$Ph), 6.90-7.50 (14H, m).

Example 5(d)

9-(2-Hydroxy-ethyl)-2,3,4,9-tetrahydro-1H-carbazole-4-carboxylic acid benzyl-methyl-amide (28)

To a solution of 9-(2-benzyloxy-ethyl)-2,3,4,9-tetrahydro-1H-carbazole-4-carboxylic acid benzyl-methyl-amide (27) (246 mg, 0.5 mmol) in methanol (15 mL) was added a slurry of Pd/C (200 mg) in methanol (10 mL). The mixture was placed on the Parr hydrogenator and shaken for 24 h under a hydrogen atmosphere. The reaction was filtered through a pad of celite, washed with methanol and concentrated in vacuo to afford 36 mg (20%) of 9-(2-hydroxy-ethyl)-2,3,4,9-tetrahydro-1H-carbazole-4-carboxylic acid benzyl-methyl-amide (28) as a green oil which was used in the next step without purification. The structure was confirmed by $^1$H NMR (CDCl$_3$) $\delta_H$ 1.80-2.20 (4H, m), 2.70-3.00 (2H, m), 3.20-4.30 (10H, m), 6.90-7.50 (9H, m).

Example 5(e)

Methanesulfonic acid 2-[4-(benzyl-methyl-carbamoyl)-1,2,3,4-tetrahydro-carbazol-9-yl]-ethyl ester (Precursor Compound 7)

To a solution of 9-(2-hydroxy-ethyl)-2,3,4,9-tetrahydro-1H-carbazole-4-carboxylic acid benzyl-methyl-amide (28) (36 mg, 0.1 mmol) in dichloromethane (2 mL) was added pyridine (7.91 g, 1.0 mmol, 8.1 mL). The reaction was cooled to 0° C. and methanesulfonyl chloride (57 mg, 0.5 mmol, 0.04 mL) was added. The reaction was allowed to warm to room temperature overnight. The mixture was washed with 2 N HCl (2×10 mL) and water (2×10 mL), dried and concentrated in vacuo. The crude material was purified by silica gel chromatography eluting with petrol (A) and ethyl acetate (B) (20-80% B, 4 g, 45 CV, 18 mL/min) to afford 14 mg (32%) of methanesulfonic acid 2-[4-(benzyl-methyl-carbamoyl)-1,2,3,4-tetrahydro-carbazol-9-yl]-ethyl ester (precursor compound 7) as a yellow oil. The structure was confirmed by $^1$H NMR (CDCl$_3$) $\delta_H$ 1.10-2.40 (5H, m), 2.51 (1.5H, s, OSO$_2$CH$_3$), 2.54 (1.5H, s, OSO$_2$CH$_3$), 2.70-2.90 (2H, m), 3.08 (1.5H, s, NCH$_3$), 3.15 (1.5H, s, NCH$_3$), 3.40-3.70 (1H, m), 4.10-4.80 (4H, m), 7.00-7.50 (9H, m).

Example 5(f)

9-(2-[$^{18}$F]fluoro-ethyl)-2,3,4,9-tetrahydro-1H-carbazole-4-carboxylic acid benzyl-methyl-amide (Imaging Agent 7)

Labelling of precursor compound 7 with $^{18}$F was carried out as described in Example 1(f). Semi-preparative HPLC: HICHROM ACE 5 C18 column (100×10 mm i.d.), particle size 5 µm; mobile phase A: Water, mobile phase B: Methanol; flow gradient: 3 ml/min; 0-1 min 50% B; 1-20 mins 50-95% B; Wavelength 254 nm; t$_R$ imaging agent 7, 17 mins.

Figure 3:
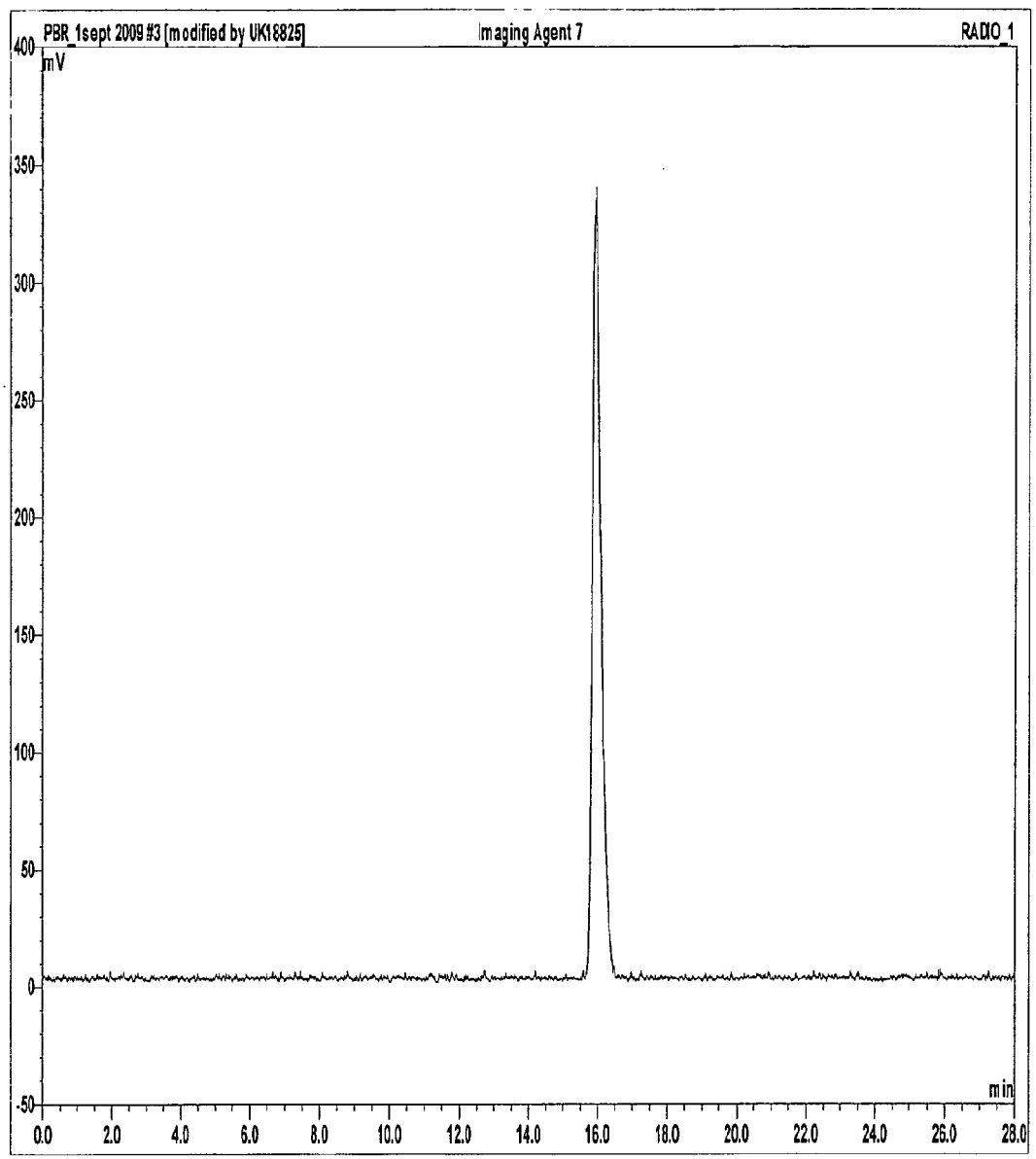
FIG. 3 shows co-elution of imaging agent 7 and non-radioactive imaging agent 7.
Figure 3:
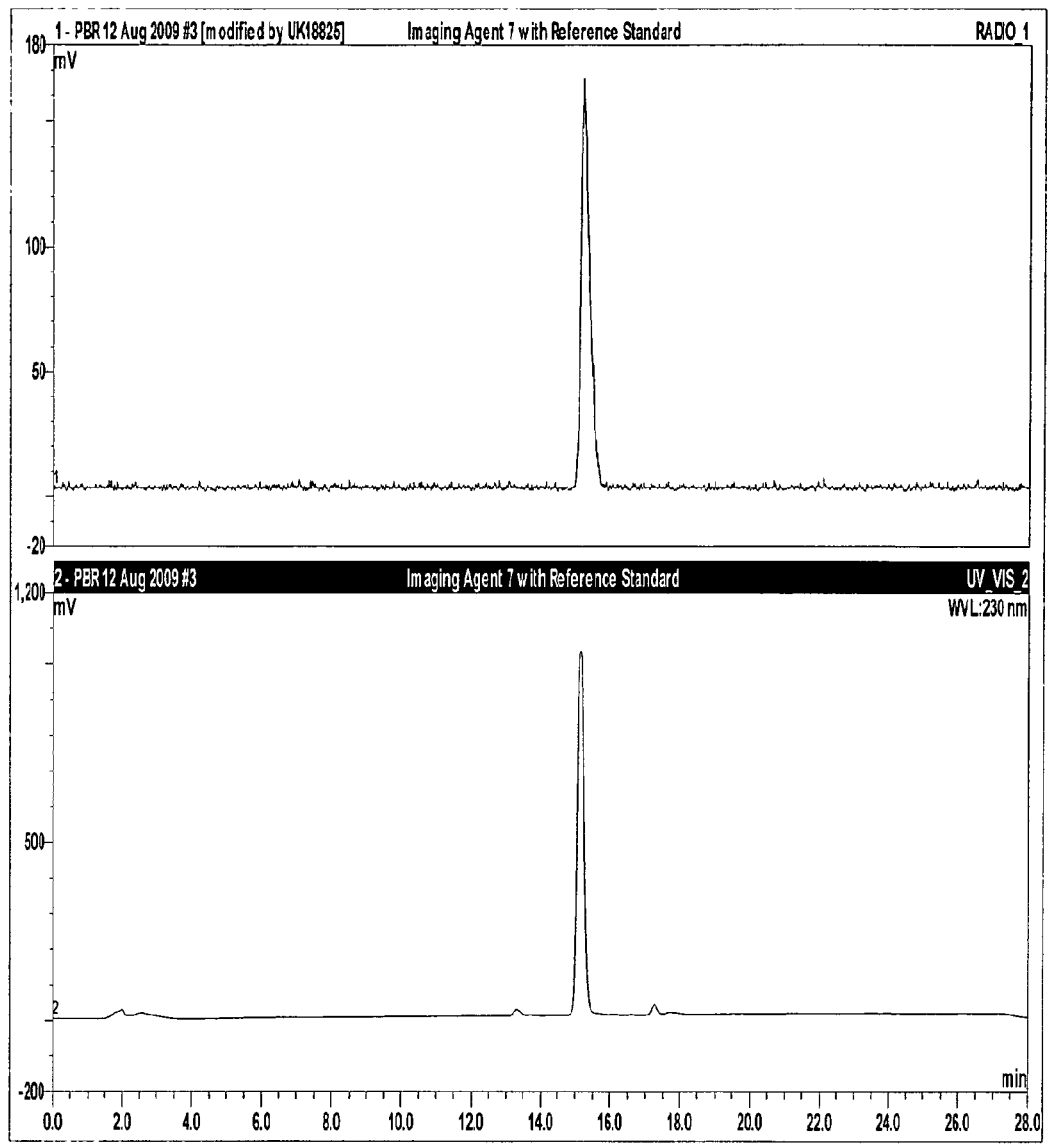

Analytical-HPLC. Phenomenex Luna C18 column (150× 4.6 mm i.d.), particle size 5 µm; mobile phase A: Water, mobile phase B: Methanol; flow gradient: 1 ml/min; 0-1 min 50% B; 1-20 mins 50-95% B; Wavelength 230 nm; t$_R$ imaging agent 7 16 mins. Radiochemical yield 23±2% (n=3) non-decay corrected, time 90-120 mins, radiochemical purity ≥99%. FIG. 3 shows co-elution of imaging agent 7 and non-radioactive imaging agent 7.

Example 6

9-(2-fluoro-ethyl)-2,3,4,9-tetrahydro-1H-carbazole-4-carboxylic acid benzyl-methyl-amide (Non-Radioactive Imaging Agent 7)

Example 6(a)

3-Bromo-2-hydroxy-cyclohex-1-enecarboxylic acid ethyl ester (29)

Ethyl 2-oxocyclohexanecarboxylate (5.0 g, 29 mmol, 4.7 mL) was dissolved in diethyl ether (5 mL) and cooled to 0° C. under N$_2$. Bromine (4.6 g, 29 mmol, 4.2 mL) was added dropwise over 15 min and the reaction mixture was allowed to warm to room temperature over 90 min. The mixture was slowly poured into ice-cold saturated aqueous sodium carbonate solution (40 mL) and extracted with ethyl acetate (3×40 mL). The combined organic layers were dried and concentrated in vacuo to afford 5.96 g (81%) of 3-bromo-2-hydroxy-cyclohex-1-enecarboxylic acid ethyl ester (29) as a pale yellow oil which was used in the next step without purification. The structure was confirmed by $^{13}$C NMR (75 MHz, DMSO-d$_6$) $\delta_C$ 14.14, 17.65, 21.77, 32.02, 59.95, 60.83, 99.70, 166.33, 172.81.

Example 6(b)

9-(2-Fluoro-ethyl)-2,3,4,9-tetrahydro-1H-carbazole-4-carboxylic acid ethyl ester (30)

A mixture of (2-fluoro-ethyl)-phenyl-amine (24; prepared according to Example 4(a)) (560 mg, 4.0 mmol) and 3-bromo-2-hydroxy-cyclohex-1-enecarboxylic acid ethyl ester (29) (500 mg, 2.0 mmol) was stirred under N$_2$ at 50° C. for 3 h and the reaction turned brown. The resulting mixture was dissolved in propan-2-ol (4 mL) and dry zinc chloride (820 mg, 6 mmol) was added. The mixture was heated to reflux under N$_2$ for 16 h and then concentrated in vacuo. The product was dissolved in ethyl acetate/ether (30 mL/150 mL) and washed with 2 N HCl (40 mL), water (2×100 mL) and aqueous potassium carbonate solution (2×100 mL) then dried and concentrated to afford 447 mg (91%) of 9-(2-fluoro-ethyl)-2,3,4,9-tetrahydro-1H-carbazole-4-carboxylic acid ethyl ester (30) as a yellow oil which was used in the next step without purification. The structure was confirmed by $^{13}$C NMR (75 MHz, CDCl$_3$) $\delta_C$ 14.3, 20.4, 21.7, 26.4, 38.5, 43.1 (d, J$_{CF}$=15 Hz), 60.6, 76.6, 77.0, 77.4, 82.1 (d, J$_{CF}$=173 Hz), 106.9, 108.5, 118.9, 119.4, 1211, 127.1, 136.2, 136.7, 174.9.

Example 6(c)

9-(2-Fluoro-ethyl)-1H-carbazole-4-carboxylic acid (31)

9-(2-Fluoro-ethyl)-2,3,4,9-tetrahydro-1H-carbazole-4-carboxylic acid ethyl ester (30) (380 mg, 1.3 mmol) was dissolved in ethanol (3 mL) and then NaOH (520 mg) in water (5 mL) was added. The reaction was heated at reflux for 2 h. The reaction was concentrated in vacuo and the residue diluted with water and washed with dichloromethane (2×50 mL). The aqueous layer was added drop wise to 2 N HCl (50 mL) and then extracted into dichloromethane (3×50 mL). The organics were dried and concentrated in vacuo to afford 130 mg (37%) of 9-(2-fluoro-ethyl)-2,3,4,9-tetrahydro-1H-carbazole-4-carboxylic acid (31) as a yellow solid which was used in the next step without purification. The structure was confirmed by $^1$H NMR (300 MHz, CDCl$_3$) $\delta$ 1.90-2.42 (4H, m, 2- and 3-C$\underline{H}_2$), 2.60-2.91 (2H, m, 1-C$\underline{H}_2$), 3.94 (1H, t, J=6 Hz, 4-C$\underline{H}$), 4.30 (1H, t, J=6 Hz, NCH$_2$C$\underline{H}_2$F), 4.37 (1H, t, J=6 Hz, NC$\underline{H}_2$CH$_2$F), 4.59 (1H, t, J=6 Hz, NCH$_2$C$\underline{H}_2$F), 4.74 (1H, t, J=6 Hz, NC$\underline{H}_2$CH$_2$F), 7.05-7.26 (3H, m, Ar$\underline{H}$), 7.59 (1H, d, J=9 Hz, Ar$\underline{H}$).

Example 6(d)

9-(2-Fluoro-ethyl)-2,3,4,9-tetrahydro-1H-carbazole-4-carbonyl chloride (32)

9-(2-Fluoro-ethyl)-2,3,4,9-tetrahydro-1H-carbazole-4-carboxylic acid (31) (0.5 g, 1.91 mmol) in dry dichloromethane (6 mL) was stirred under an atmosphere of nitrogen at room temperature with oxalyl chloride (490 mg, 3.8 mmol, 0.34 mL) and a drop of DMF. The reaction was concentrated in vacuo to afford 545 mg (quantitative) of 9-(2-fluoro-ethyl)-2,3,4,9-tetrahydro-1H-carbazole-4-carbonyl chloride (32) which was used in the next step without purification. The structure was confirmed by $^{13}$C NMR (75 MHz, CDCl$_3$) $\delta_C$ 20.2, 21.6, 26.7, 43.1, 43.4, 50.6, 80.9, 83.1, 105.3, 108.8, 118.3, 120.0, 121.6, 126.5, 136.2, 137.5, 176.1.

Example 6(e)

9-(2-Fluoro-ethyl)-2,3,4,9-tetrahydro-1H-carbazole-4-carboxylic acid benzyl-methyl-amide (Non-Radioactive Imaging Agent 7)

9-(2-Fluoro-ethyl)-2,3,4,9-tetrahydro-1H-carbazole-4-carbonyl chloride (32) (110 mg, 0.4 mmol) was dissolved in dichloromethane (1 mL) and cooled to 0° C. N-Benzylmethylamine (92 mg, 0.8 mmol, 98 µL) was then added and the reaction was stirred overnight at RT. The reaction was quenched with 10% aqueous potassium carbonate solution (2 mL). The dichloromethane layer was collected through a phase separator then concentrated in vacuo. The crude material was purified by silica gel chromatography eluting with petrol (A) and ethyl acetate (B) (20-100% B, 12 g, 30 CV, 30 mL/min) to afford 39 mg (28%) of 9-(2-fluoro-ethyl)-2,3,4,9-tetrahydro-1H-carbazole-4-carboxylic acid benzyl-methyl-amide (non-radioactive imaging agent 7). The structure was confirmed by $^1$H NMR (300 MHz, CDCl$_3$) $\delta_H$ 75-2.32, (4H, m, 2- and 3-C$\underline{H}_2$), 2.68-2.86 (2H, m, 1-C$\underline{H}_2$), 3.10 (1H, s, NC$\underline{H}_3$), 3.14 (2H, s, NC$\underline{H}_3$), 4.17-4.39 (3H, m, NC$\underline{H}_2$CH$_2$F and 4-C$\underline{H}_2$), 4.52-4.87 (4H, m, NC$\underline{H}_2$Ph and NCH$_2$C$\underline{H}_2$F), 6.96-7.42 (9H, m, Ar$\underline{H}$).

Example 7

Synthesis of Methanesulfonic acid 2-(4-diethylcarbamoyl-6-fluoro-1,2,3,4-tetrahydro-carbazol-9-yl)-ethyl ester (Precursor Compound 9) and 6-Fluoro-9-(2-[$^{18}$F]fluoro-ethyl)-2,3,4,9-tetrahydro-1H-carbazole-4-carboxylic acid diethylamide (Imaging Agent 9)

Example 7(a)

2-benzyloxy-N-(4-fluoro-phenyl)-acetamide (33)

To a solution of benzyloxyacetic acid (4.6 g, 28.0 mmol, 4.0 mL) in DCM (52 mL) was added oxalyl chloride (7.7 g, 61 mmol, 5.3 mL) and a drop of DMF. The reaction mixture was stirred at room temperature for 4 h. Excess of oxalyl chloride was removed in vacuo to give benzyloxy-acetyl chloride. The crude acyl chloride was diluted into DCM (100 mL) and triethylamine (5.3 mL, 41.6 mmol, 4.2 g) was added followed by 4-fluoroaniline (3.5 g, 32 mmol, 3.0 mL). The reaction mixture was stirred at RT overnight. The reaction was then quenched with 1 M aqueous HCl (100 mL), dried and concentrated in vacuo to give 7.1 g (95%) of 2-benzyloxy-N-(4-fluoro-phenyl)-acetamide (33) as a yellow oil which was used in the next step without purification. The structure was confirmed by $^{13}$C NMR (75 MHz, CDCl$_3$) $\delta_C$ 69.2, 73.5, 115.4 (d, J$_{CF}$=22 Hz), 121.4 (d, J$_{CF}$=7 Hz), 127.9, 128.2, 128.5, 132.5 (d, J$_{CF}$=3 Hz), 136.3, 157.6, 160.8, and 167.5.

Example 7(b)

(2-Benzyloxy-ethyl)-(4-fluoro-phenyl)-amine (34)

To a suspension of LAH (1.25 g, 27 mmol) in dry diethyl ether (100 mL) was added dropwise a solution of 2-benzyloxy-N-(4-fluoro-phenyl)-acetamide (33) (6.9 g, 27 mmol) in dry diethyl ether (100 mL). The addition was such as a reflux was maintained. Once the addition was completed, the reaction mixture was heated to reflux for 4 h, then poured into ice-water and DCM was added. In order to break down the aluminium salt, 2M aqueous sodium hydroxide solution was added until strong basic pH was obtained. The layers were separated and the aqueous layer was washed with DCM, dried and concentrated in vacuo. The crude material was purified by silica gel chromatography eluting with petrol (A) and ethyl acetate (B) (5-50% B, 100 g, 12 CV, 60 mL/min) to afford 5.5 g (84%) of (2-benzyloxy-ethyl)-(4-fluoro-phenyl)-amine (34) as a yellow oil. The structure was confirmed by $^{13}$C NMR (75 MHz, CDCl$_3$) $\delta_C$ 44.0, 68.3, 72.8, 113.7 (d, $J_{CF}$=7 Hz), 115.3 (d, $J_{CF}$=22 Hz), 127.5, 127.6 (d, $J_{CF}$=3 Hz), 128.3, 137.8, 144.5, 154.1, and 157.2.

Example 7(c)

3-Bromo-2-oxo-cyclohexanecarboxylic acid diethylamide (35)

Ethyl 2-cyclohexone-carboxylate (7.50 mL, 47.0 mmol), DMAP (1.72 g, 14.1 mmol) and diethylamine (9.77 mL, 94.0 mmol) were heated at reflux for 72 hours in toluene (100 mL). The reaction was allowed to cool and the toluene was removed under reduced pressure. The crude oil was purified by silica gel chromatography eluting with petrol (A) and ethyl acetate (B) (1:1, 100 g, SiO$_2$) to afford 6.8 g (73%) of 2-oxo-cyclohexanecarboxylic acid diethylamine as an orange oil. The structure was confirmed by $^{13}$C NMR (CDCl$_3$) $\delta$ 11.1, 12.7, 21.3, 24.9, 28.5, 39.4, 39.6, 51.7, 166.5, 205.9.

2-oxo-cyclohexanecarboxylic acid diethylamine (3.56 mL, 19.3 mmol) was dissolved in diethyl ether (5 mL) and cooled with stirred to 0° C. under N$_2$. Bromine (0.99 mL, 19.3 mmol) was added drop wise over 15 minutes and the reaction mixture was allowed to warm to room temperature over 3 hours. A solid had precipitated out of the reaction. It was collected by filtration and washed with ether to give 5.85 g (109%) of 3-Bromo-2-oxo-cyclohexanecarboxylic acid diethylamide (35) as a pale yellow solid. The structure was confirmed by $^{13}$C NMR (CDCl$_3$) $\delta$11.2, 12.8, 22.7, 28.8, 37.6, 37.9, 39.4, 51.0, 55.7, 165.5, 197.2

Example 7(d)

9-(2-Benzyloxy-ethyl)-6-fluoro-2,3,4,9-tetrahydro-1H-carbazole-4-carboxylic acid diethylamide (36)

A mixture of 2-benzyloxy-N-(4-fluoro-phenyl)-acetamide (33) (5.3 g, 22 mmol) and 3-bromo-2-oxo-cyclohexanecarboxylic acid diethylamide (35) (3.0 g, 13 mmol)) was stirred under N$_2$ at 50° C. for 3 h and the reaction turned brown. The resulting mixture was dissolved in propan-2-ol (30 mL) and dry zinc chloride (9.0 g, 66 mmol) was added. The mixture was heated to reflux under N$_2$ for 16 h and then concentrated in vacuo. The residue was dissolved in ethyl acetate (300 mL) and washed with 2 N HCl (100 mL), water (2×100 mL) and aqueous potassium carbonate solution (2×100 mL) then dried and concentrated in vacuo. The crude material was purified by silica gel chromatography eluting with petrol (A) and ethyl acetate (B) (10-50% B, 100 g) to afford 196 mg (11%) of 9-(2-benzyloxy-ethyl)-6-fluoro-2,3,4,9-tetrahydro-1H-carbazole-4-carboxylic acid diethylamide (36) as a white solid. The structure was confirmed by $^1$H NMR (300 MHz, CDCl$_3$) $\delta_H$ 1.14 (3H, t, J=7 Hz, N(CH$_2$CH$_3$)$_2$), 1.30 (3H, t, J=7 Hz, N(CH$_2$CH$_3$)$_2$), 1.60-2.60 (4H, m, 2- and 3-CH$_2$), 2.70-2.85 (2H, m, 1-CH$_2$), 3.10-3.65 (4H, m, N(CH$_2$CH$_3$)$_2$ and NCH$_2$CH$_2$OBn), 3.66-3.75 (1H, m, 4-CH), 4.00-4.25 (2H, m, NCH$_2$CH$_2$OBn), 4.41 (2H, s, OCH$_2$Ph), 6.75-6.95 (2H, m, NCCHCHCFCH), 7.05-7.15 (1H, m, NCCHCHCFCH), and 7.16-7.25 (5H, m, Ph).

Example 7(d)

6-Fluoro-9-(2-hydroxy-ethyl)-2,3,4,9-tetrahydro-1H-carbazole-4-carboxylic acid diethylamide (37)

To a solution of 9-(2-benzyloxy-ethyl)-6-fluoro-2,3,4,9-tetrahydro-1H-carbazole-4-carboxylic acid diethylamide (36) (600 mg, 1.4 mmol) in methanol (40 mL) was added a slurry of Pd/C (100 mg) in methanol (5 mL). The mixture was placed on the Parr hydrogenator and shaken for 24 h under a hydrogen atmosphere. The reaction was filtered through a pad of celite, washed with methanol and concentrated in vacuo to afford 460 mg (80%) of 6-fluoro-9-(2-hydroxy-ethyl)-2,3,4, 9-tetrahydro-1H-carbazole-4-carboxylic acid diethylamide (37) as a yellow oil which was used in the next step without purification. The structure was confirmed by $^1$H NMR (300 MHz, MeOD-d$_3$) $\delta_H$ 1.18 (3H, t, J=9 Hz, N(CH$_2$CH$_3$)$_2$), 1.35 (3H, t, J=9 Hz, N(CH$_2$CH$_3$)$_2$), 1.80-2.20 (4H, m, 2- and 3-CH$_2$), 2.69-3.88 (2H, m, 1-CH$_2$), 3.40-3.86 (6H, m, N(CH$_2$CH$_3$)$_2$ and NCH$_2$CH$_2$OH), 4.03-4.22 (3H, m, NCH$_2$CH$_2$OH and 4-CH), 6.75-6.95 (2H, m, NCCHCHCFCH), and 7.05-7.15 (1H, m, NCCHCHCFCH.

Example 7(e)

Methanesulfonic acid 2-(4-diethylcarbamoyl-6-fluoro-1,2,3,4-tetrahydro-carbazol-9-O-ethyl ester (Precursor Compound 9)

To a solution of 6-fluoro-9-(2-hydroxy-ethyl)-2,3,4,9-tetrahydro-1H-carbazole-4-carboxylic acid diethylamide (37) (460 mg, 1.4 mmol) in dichloromethane (20 mL) was added pyridine (1.11 g, 14.0 mmol, 1.1 mL). The reaction was cooled to 0° C. and methanesulfonyl chloride (722 mg, 6.3 mmol, 0.5 mL) was added. The reaction was allowed to warm to room temperature overnight. The mixture was washed with 2 N HCl (2×30 mL) and water (2×30 mL), dried and concentrated in vacuo. The crude material was purified by silica gel chromatography eluting with petrol (A) and ethyl acetate (B) (0-100% (B), 10 g, 45 CV, 30 mL/min) then triturated with diethyl ether to afford 166 mg (30%) of methanesulfonic acid 2-(4-diethylcarbamoyl-6-fluoro-1,2,3,4-tetrahydro-carbazol-9-yl)-ethyl ester (precursor compound 9) as a white solid. The structure was confirmed by $^{13}$C NMR (75 MHz, CDCl$_3$) $\delta_C$ 12.9, 15.0, 21.1, 27.7, 36.1, 36.7, 40.6, 41.7, 67.8, 103.3 (d, $J_{CF}$=23 Hz), 108.7, 109.0, 109.1, 109.4 (d, $J_{CF}$=5 Hz), 126.9 (d, $J_{CF}$=10 Hz), 132.4, 138.4, 156.1, 159.2, and 173.3.

Example 7(f)

6-Fluoro-9-(2-[$^{18}$F]fluoro-ethyl)-2,3,4,9-tetrahydro-1H-carbazole-4-carboxylic acid diethylamide (Imaging Agent 9)

Labelling of precursor compound 9 with $^{18}$F was carried out as described in Example 1(f).

Semi-preparative HPLC: HICHROM ACE 5 C18 column (100×10 mm i.d.), particle size 5 μm; mobile phase A: Water, mobile phase B: Methanol; flow gradient: 3 ml/min; 0-1 min 40% B; 1-20 mins 40-95% B; Wavelength 254 nm; $t_R$ imaging agent 9 15 mins.

Figure 4:
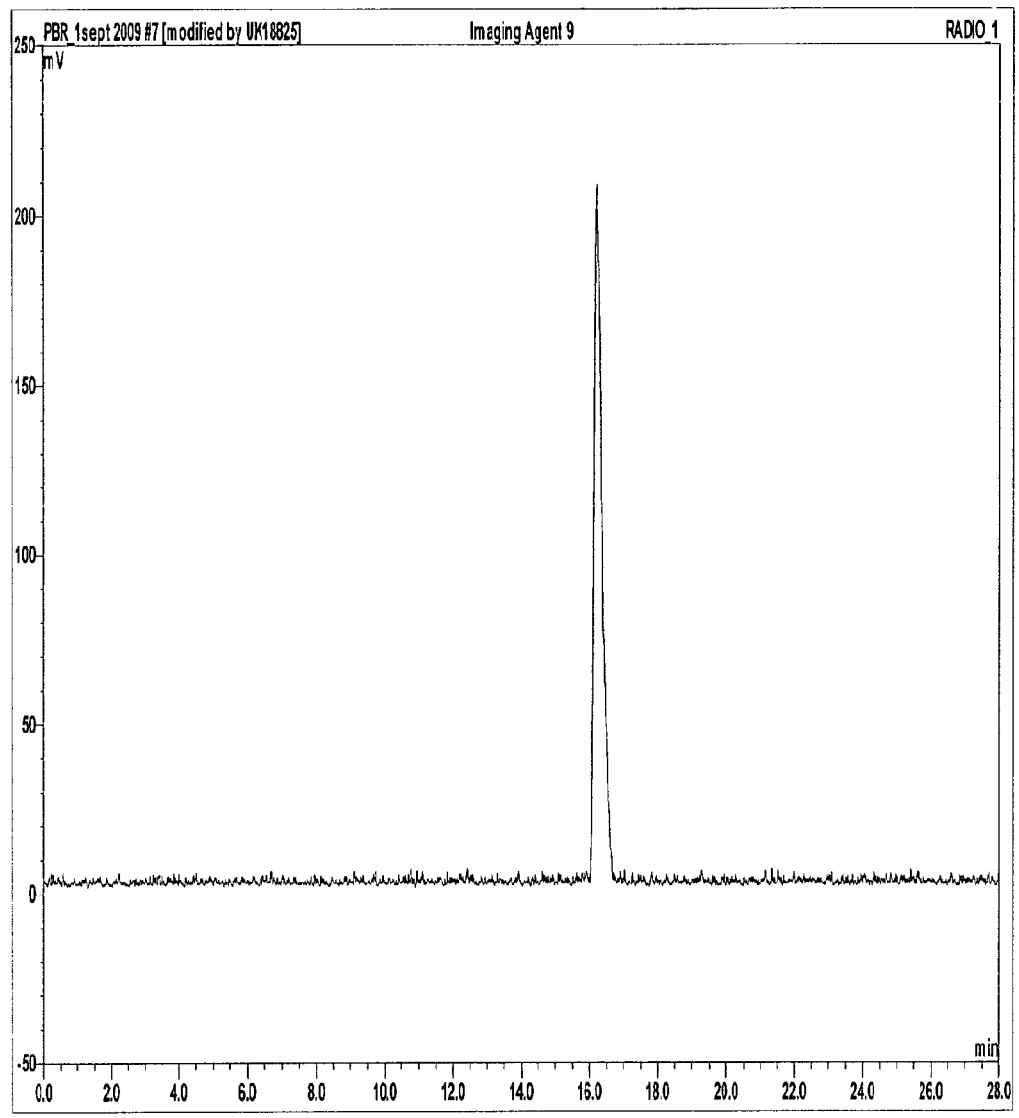
FIG. 4 shows co-elution of imaging agent Sand non-radioactive imaging agent 9.
Figure 4:
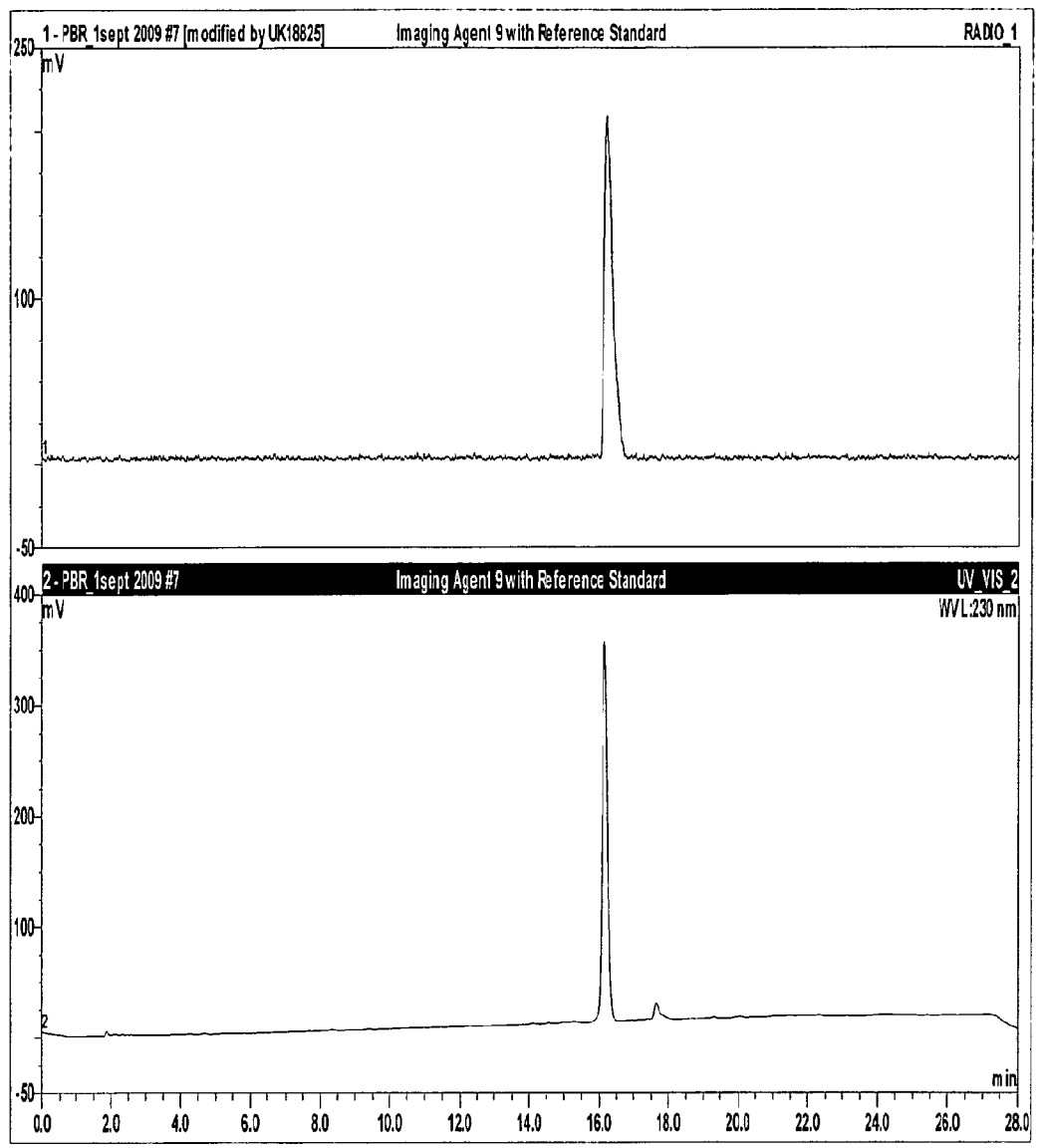

Analytical-HPLC: Phenomenex Luna C18 column (150× 4.6 mm i.d.), particle size 5 μm; mobile phase A: Water, mobile phase B: Methanol; flow gradient: 1 ml/min; 0-1 min 50% B; 1-20 mins 50-95% B; Wavelength 230 nm; $t_R$ imaging agent 9 14 mins. Radiochemical yield 26±8% (n=4) non-decay corrected, time 90-120 mins, radiochemical purity ≥99%. FIG. 4 shows co-elution of imaging agent 9 and non-radioactive imaging agent 9.

Example 8

Synthesis of 6-Fluoro-9-(2-fluoro-ethyl)-2,3,4,9-tetrahydro-1H-carbazole-4-carboxylic acid diethylamide (Non-Radioactive Imaging Agent 9)

Example 8(a)

(2-Fluoro-ethyl)-(4-fluoro-phenyl)-amine (38)

In a round bottom flask 4-fluoroaniline (1.3 g, 11.6 mmol, 1.6 mL) 2,6-lutidine (1.24 g, 11.6 mmol) and 2-fluoroethyl tosylate (12; prepared according to Example 2(a)) (2.5 g, 11.6 mmol) were combined in DMF (5 mL) and stirred at 100° C. overnight. The reaction was allowed to cool and then diluted with ethyl acetate (100 mL). This was washed with water (3×40 mL) and the organics were dried and concentrated in vacuo. The crude material was purified by silica gel chromatography eluting with petrol (A) and ethyl acetate (B) (10% B, 100 g, 12 CV, 60 mL/min) to afford 383 mg (20%) of (2-fluoro-ethyl)-(4-fluoro-phenyl)-amine (38) as a yellow oil. The structure was confirmed by $^1$H NMR (300 MHz, CDCl$_3$) $\delta_H$ 3.30-3.35 (1H, m, NC$\underline{H}_2$CH$_2$F), 3.40-3.45 (1H, m, NCH$_2$CH$_2$F), 3.90 (1H, s, br, N$\underline{H}$), 4.53 (1H, t, J=3 Hz, NCH$_2$C$\underline{H}_2$F), 4.69 (1H, t, J=3 Hz, NCH$_2$C$\underline{H}_2$F), 6.51-6.72 (2H, m, 2×NCC$\underline{H}$), 6.85-7.05 (2H, m, 2×NCCHC$\underline{H}$).

Example 8(b)

6-Fluoro-9-(2-fluoro-ethyl)-2,3,4,9-tetrahydro-1H-carbazole-4-carboxylic acid diethylamide (Non-Radioactive Imaging Agent 9)

A mixture of 3-bromo-2-oxo-cyclohexanecarboxylic acid diethylamide (35; prepared according to Example 7(c)) (336 mg, 1.2 mmol) and (2-fluoro-ethyl)-(4-fluoro-phenyl)-amine (38) (383 mg, 2.4 mmol) was stirred under N$_2$ at 50° C. for 3 h and the reaction turned brown. The resulting mixture was dissolved in propan-2-ol (2 mL) and dry zinc chloride (491 mg, 3.6 mmol) was added. The mixture was heated to reflux under N$_2$ for 16 h and then concentrated in vacuo. The residue was dissolved in ethyl acetate (20 mL) and washed with 2 N HCl (10 mL), water (2×10 mL) and aqueous potassium carbonate solution (2×5 mL) then dried and concentrated in vacuo. The crude material was triturated with diethyl ether to afford 40 mg (10%) of 6-fluoro-9-(2-fluoro-ethyl)-2,3,4,9-tetrahydro-1H-carbazole-4-carboxylic acid diethylamide (non-radioactive imaging agent 9) as white solid. The structure was confirmed by $^1$H NMR (300 MHz, CDCl$_3$) $\delta_H$ 1.13 (3H, t, J=9 Hz, N(CH$_2$C$\underline{H}_3$)$_2$), 1.30 (3H, t, J=9 Hz, N(C$\underline{H}_2$CH$_3$)$_2$), 1.55-2.14 (4H, m, 2- and 3-C$\underline{H}_2$), 2.78-2.86 (2H, m, 1-C$\underline{H}_2$), 3.36-3.67 (4H, m, N(C$\underline{H}_2$CH$_3$)$_2$), 4.00-4.10 (1H, m, 4-C$\underline{H}$), 4.30 (2H, dm, J=21 Hz, NC$\underline{H}_2$CH$_2$F), 4.60 (2H, dm, J=41 Hz, NCH$_2$C$\underline{H}_2$F), 6.75-6.95 (2H, m, NCC$\underline{H}$C$\underline{H}$FCH), and 7.05-7.15 (1H, m, NCCHCHCFC$\underline{H}$).

Example 9

Synthesis of Methanesulfonic acid 2-(4-diethylcarbamoyl-5-fluoro-1,2,3,4-tetrahydro-carbazol-9-yl)-ethyl ester (Precursor Compound 10) and 5-Fluoro-9-(2-[$^{18}$F]fluoro-ethyl)-2,3,4,9-tetrahydro-1H-carbazole-4-carboxylic acid diethylamide (Imaging Agent 10)

Example 9(a)

2-benzyloxy-N-(3-fluoro-phenyl)-acetamide (39)

To a solution of benzyloxyacetic acid (4.65 g, 28 mmol, 4.0 mL) in DCM (52 mL) was added oxalyl chloride (7.7 g, 61 mmol, 5.3 mL) and a drop of DMF. The reaction mixture was stirred at room temperature for 4 h. Excess of oxalyl chloride was removed in vacuo and the crude acyl chloride was diluted into DCM (100 mL) and triethylamine (5.3 mL, 41.6 mmol, 4.2 g) was added followed by 3-fluoroaniline (3.5 g, 32 mmol, 3.0 mL). The reaction mixture was stirred at RT overnight. The reaction was then quenched with 1 M aqueous HCl (100 mL), dried and concentrated in vacuo to afford 7.10 g (95%) of 2-benzyloxy-N-(3-fluoro-phenyl)-acetamide (39) as a yellow oil which was used in the next step without purification. The structure was confirmed by $^{13}$C NMR (75 MHz, CDCl$_3$) be 69.2, 73.5, 106.9, 107.2, 111.0 (d, J$_{CF}$=24 Hz), 114.9 (d, J$_{CF}$=3 Hz), 127.8, 128.2, 128.5, 129.7 (d, J$_{CF}$=9 Hz), 136.2, and 167.6.

Example 9(b)

(2-Benzyloxy-ethyl)-(3-fluoro-phenyl)-amine (40)

To a suspension of LAH (1.25 g, 27 mmol) in dry diethyl ether (100 mL) was added dropwise a solution of 2-benzyloxy-N-(3-fluoro-phenyl)-acetamide (39) (7.0 g, 27 mmol) in dry diethyl ether (100 mL). The addition was such as a reflux was maintained. Once the addition was completed, the reaction mixture was heated to reflux for 4 h, then poured into ice-water and DCM was added. In order to break down the aluminium salt, 2M aqueous sodium hydroxide solution was added until strong basic pH was obtained. The layers were separated and the aqueous layer was washed with DCM, dried and concentrated in vacuo. The crude material was purified by silica gel chromatography eluting with petrol (A) and ethyl acetate (B) (5-50% B, 100 g, 12 CV, 60 mL/min) to afford 4.1 g (84%) of (2-benzyloxy-ethyl)-(3-fluoro-phenyl)-amine (40) as a yellow oil. The structure was confirmed by $^{13}$C NMR (75 MHz, CDCl$_3$): $\delta_C$ 43.3, 68.2, 73.0, 99.4 (d, J$_{CF}$=24 Hz), 103.5, 103.8, 108.8, 127.4 (d, J$_{CF}$=3 Hz), 127.6, 128.4, 130.0 (d, J$_{CF}$=9 Hz), and 138.8.

Example 9(c)

9-(2-Benzyloxy-ethyl)-5-fluoro-2,3,4,9-tetrahydro-1H-carbazole-4-carboxylic acid diethylamide (41)

A mixture of 3-bromo-2-oxo-cyclohexanecarboxylic acid diethylamide (35; prepared according to Example 7(c)) (2.3 g, 10 mmol) and (2-benzyloxy-ethyl)-(3-fluoro-phenyl)-amine (40) (4.1 g, 17 mmol) was stirred under N$_2$ at 50° C. for 3 h and the reaction turned brown. The resulting mixture was dissolved in propan-2-ol (10 mL) and dry zinc chloride (4.09 g, 30 mmol) was added. The mixture was heated to reflux under N$_2$ for 16 h and then concentrated in vacuo. The residue was dissolved in ethyl acetate (200 mL) and washed with 2 N HCl (50 mL), water (2×50 mL) and aqueous potassium carbonate solution (2×50 mL) then dried and concentrated in vacuo. The crude material was purified by silica gel chromatography eluting with petrol (A) and ethyl acetate (B) (5-100% B, 100 g, 28 CV, 60 mL/min) to afford 1.3 g (30%) of 9-(2-benzyloxy-ethyl)-5-fluoro-2,3,4,9-tetrahydro-1H-carbazole-4-carboxylic acid diethylamide (41) along with the isomer 9-(2-benzyloxy-ethyl)-7-fluoro-2,3,4,9-tetrahydro-1H-carbazole-4-carboxylic acid diethylamide as a mixture which was used in the next step without purification. The structure of 9-(2-benzyloxy-ethyl)-5-fluoro-2,3,4,9-tetrahydro-1H-carbazole-4-carboxylic acid diethylamide (41) was confirmed by $^1$H NMR (300 MHz, CDCl$_3$) $\delta_H$ 1.10-1.40 (6H, m, N(CH$_2$CH$_3$)$_2$), 1.60-2.60 (4H, m, 2- and 3-CH$_2$), 2.70-2.85 (2H, m, 1-CH$_2$), 3.10-3.65 (4H, m, N(CH$_2$CH$_3$)$_2$ and CH$_2$CH$_2$OBn), 4.00-4.30 (3H, m, CH$_2$CH$_2$OBn and 4-CH), 4.43 (2H, s, OCH$_2$Ph), 6.55-6.65 (1H, m, NCCHCHCHCF), 6.90-7.05 (1H, m, NCCHCHCHCF), 7.05-7.15 (1H, m, NCCHCHCHCF), and 7.16-7.25 (5H, m, Ph). The structure of 9-(2-benzyloxy-ethyl)-7-fluoro-2,3,4,9-tetrahydro-1H-carbazole-4-carboxylic acid diethylamide was confirmed by $^1$H NMR (300 MHz, CDCl$_3$) $\delta_H$ 1.10-1.40 (6H, m, N(CH$_2$CH$_3$)$_2$), 1.60-2.60 (4H, m, 2- and 3-CH$_2$), 2.70-2.85 (2H, m, 1-CH$_2$), 3.10-3.65 (4H, m, N(CH$_2$CH$_3$)$_2$ and NCH$_2$CH$_2$OBn), 4.00-4.30 (3H, m, NCH$_2$CH$_2$Obn and 4-CH), 4.55 (2H, s, OCH$_2$Ph), 6.70-6.80 (1H, m, NCCHCFCHCH), and 7.00-7.40 (7H, m, NCCHCFCHCH and Ph).

Example 9(d)

5-Fluoro-9-(2-hydroxy-ethyl)-2,3,4,9-tetrahydro-1H-carbazole-4-carboxylic acid diethylamide (42)

To a solution of a mixture of 9-(2-benzyloxy-ethyl)-5-fluoro-2,3,4,9-tetrahydro-1H-carbazole-4-carboxylic acid diethylamide (41) and 9-(2-benzyloxy-ethyl)-7-fluoro-2,3,4,9-tetrahydro-1H-carbazole-4-carboxylic acid diethylamide (1.3 g, 3.0 mmol) in methanol (75 mL) was added a slurry of Pd/C (200 mg) in methanol (10 mL). The mixture was placed on the Parr hydrogenator and shaken for 24 h under a hydrogen atmosphere. The reaction was filtered through a pad of celite, washed with methanol and concentrated in vacuo to afford 743 mg (80%) of a mixture of 5-fluoro-9-(2-hydroxy-ethyl)-2,3,4,9-tetrahydro-1H-carbazole-4-carboxylic acid diethylamide (42) and 7-fluoro-9-(2-hydroxy-ethyl)-2,3,4,9-tetrahydro-1H-carbazole-4-carboxylic acid diethylamide as a yellow oil which was used in the next step without purification. The structure of 5-fluoro-9-(2-hydroxy-ethyl)-2,3,4,9-tetrahydro-1H-carbazole-4-carboxylic acid diethylamide (55) was confirmed by $^1$H NMR (300 MHz, CDCl$_3$) $\delta_H$ 1.10-1.40 (6H, m, N(CH$_2$CH$_3$)$_2$), 1.60-2.60 (4H, m, 2- and 3-CH$_2$), 2.70-2.85 (2H, m, 1-CH$_2$), 3.10-3.65 (4H, m, N(CH$_2$CH$_3$)$_2$ and CH$_2$CH$_2$OH), 4.00-4.30 (3H, m, CH$_2$CH$_2$OH, 4-CH), 6.55-6.65 (1H, m, NCCHCHCHCF), 6.90-7.05 (1H, m, NCCHCHCHCF), and 7.05-7.15 (1H, m, NCCHCHCHCF).

The structure of 7-fluoro-9-(2-hydroxy-ethyl)-2,3,4,9-tetrahydro-1H-carbazole-4-carboxylic acid diethylamide was confirmed by $^1$H NMR (300 MHz, CDCl$_3$) $\delta_H$ 1.10-1.40 (6H, m, N(CH$_2$CH$_3$)$_2$), 1.60-2.60 (4H, m, 2- and 3-CH$_2$), 2.70-2.85 (2H, m, 1-CH$_2$), 3.10-3.65 (4H, m, N(CH$_2$CH$_3$)$_2$ and CH$_2$CH$_2$OH), 4.00-4.30 (3H, m, NCH$_2$CH$_2$OH, 4-CH), 6.70-6.80 (1H, m, NCCHCFCHCH), and 7.00-7.40 (2H, m, NCCHCFCHCH).

Example 9(e)

Methanesulfonic acid 2-(4-diethylcarbamoyl-5-fluoro-1,2,3,4-tetrahydro-carbazol-9-yl)-ethyl ester (Precursor Compound 10)

To a solution of a mixture of 5-fluoro-9-(2-hydroxy-ethyl)-2,3,4,9-tetrahydro-1H-carbazole-4-carboxylic acid diethylamide (42) and 7-fluoro-9-(2-hydroxy-ethyl)-2,3,4,9-tetrahydro-1H-carbazole-4-carboxylic acid diethylamide (743 mg, 2.2 mmol) in dichloromethane (30 mL) was added pyridine (1.74 g, 22.0 mmol, 1.8 mL). The reaction was cooled to 0° C. and methanesulfonyl chloride (1.01 g, 8.8 mmol, 0.7 mL) was added. The reaction was allowed to warm to room temperature overnight. The mixture was washed with 2 N HCl (2×50 mL) and water (2×50 mL), dried and concentrated in vacuo. The crude material was purified by semi preparative HPLC eluting with water (A) and methanol (B) (Gemini 5 u, C18, 110A, 150×21 mm, 50-95% B over 20 min, 21 mL/min) to afford 10 mg (1%) of methanesulfonic acid 2-(4-diethylcarbamoyl-7-fluoro-1,2,3,4-tetrahydro-carbazol-9-yl)-ethyl ester as a white solid and 30 mg (9%) of a mixture of methanesulfonic acid 2-(4-diethylcarbamoyl-7-fluoro-1,2,3,4-tetrahydro-carbazol-9-yl)-ethyl ester and methanesulfonic acid 2-(4-diethylcarbamoyl-5-fluoro-1,2,3,4-tetrahydro-carbazol-9-yl)-ethyl ester (precursor compound 10) as a white solid. Using these purification conditions, methanesulfonic acid 2-(4-diethylcarbamoyl-5-fluoro-1,2,3,4-tetrahydro-carbazol-9-yl)-ethyl ester (precursor compound 10) could not be isolated as a single component. The structure of methanesulfonic acid 2-(4-diethylcarbamoyl-7-fluoro-1,2,3,4-tetrahydro-carbazol-9-yl)-ethyl ester was confirmed by $^1$H NMR (300 MHz, CDCl$_3$) $\delta_H$ 1.18 (3H, t, J=7 Hz, N(CH$_2$CH$_3$)$_2$), 1.39 (3H, t, J=7 Hz, N(CH$_2$CH$_3$)$_2$) 1.70-2.30 (4H, m, 2- and 3-CH$_2$), 2.58 (3H, s, OSO$_2$CH$_3$), 2.60-2.80 (2H, m, 1-CH$_2$), 3.40-3.65 (4H, m, N(CH$_2$CH$_3$)$_2$), 4.02 (1H, t, J=6 Hz, 4-CH), 4.20 (2H, t, J=7 Hz, NCH$_2$CH$_2$O Ms), 4.35 (2H, t, J=7 Hz, NCH$_2$CH$_2$O Ms), 6.70-6.85 (1H, m, NCCHCFCHCH), 6.90-7.00 (1H, m, NCCHCFCHCH), and 7.05-7.15 (2H, m, NCCHCFCHCH).

The structure of methanesulfonic acid 2-(4-diethylcarbamoyl-5-fluoro-1,2,3,4-tetrahydro-carbazol-9-yl)-ethyl ester (precursor compound 10) was confirmed by $^1$H NMR (300 MHz, CDCl$_3$) $\delta_H$ 1.18 (3H, t, J=7 Hz, N(CH$_2$CH$_3$)$_2$), 1.39 (3H, t, J=7 Hz, N(CH$_2$CH$_3$)$_2$) 1.70-2.30 (4H, m, 2- and 3-CH$_2$), 2.58 (3H, s, OSO$_2$CH$_3$), 2.60-2.80 (2H, m, 1-CH$_2$), 3.40-3.65 (4H, m, N(CH$_2$CH$_3$)$_2$), 4.15 (1H, m, 4-CH), 4.20 (2H, t, J=7 Hz, NCH$_2$CH$_2$OMs), 4.35 (2H, t, J=7 Hz, NCH$_2$CH$_2$OMs), 6.55-6.65 (1H, m, NCCHCHCHCF), 6.90-7.05 (1H, m, NCCHCHCHCF), and 7.05-7.15 (1H, m, NCCHCHCHCF).

Example 9(f)

5-Fluoro-9-(2-[$^{18}$F]fluoro-ethyl)-2,3,4,9-tetrahydro-1H-carbazole-4-carboxylic acid diethylamide (Imaging Agent 10)

The mixture of precursor compound 10 and methanesulfonic acid 2-(4-diethylcarbamoyl-7-fluoro-1,2,3,4-tetrahydro-carbazol-9-yl)-ethyl ester was used in the radiolabelling reaction. Labelling with $^{18}$F was carried out as described in Example 1(f). 7-Fluoro-9-(2-[$^{18}$F]fluoro-ethyl)-2,3,4,9-tetrahydro-1H-carbazole-4-carboxylic acid diethylamide imaging agent 10 were obtained.

Semi-preparative HPLC: HICHROM ACE 5 C18 column (100×10 mm i.d.), particle size 5 µm; mobile phase A. Water, mobile phase B: Methanol; flow gradient: 3 ml/min; 0-1 min 50% B; 1-20 mins 50-95% B; Wavelength 254 nm; $t_R$ imaging agent 10 15 mins; $t_R$ 7-Fluoro-9-(2-[$^{18}$F]fluoro-ethyl)-2,3,4,9-tetrahydro-1H-carbazole-4-carboxylic acid diethylamide 14 mins.

Figure 5:
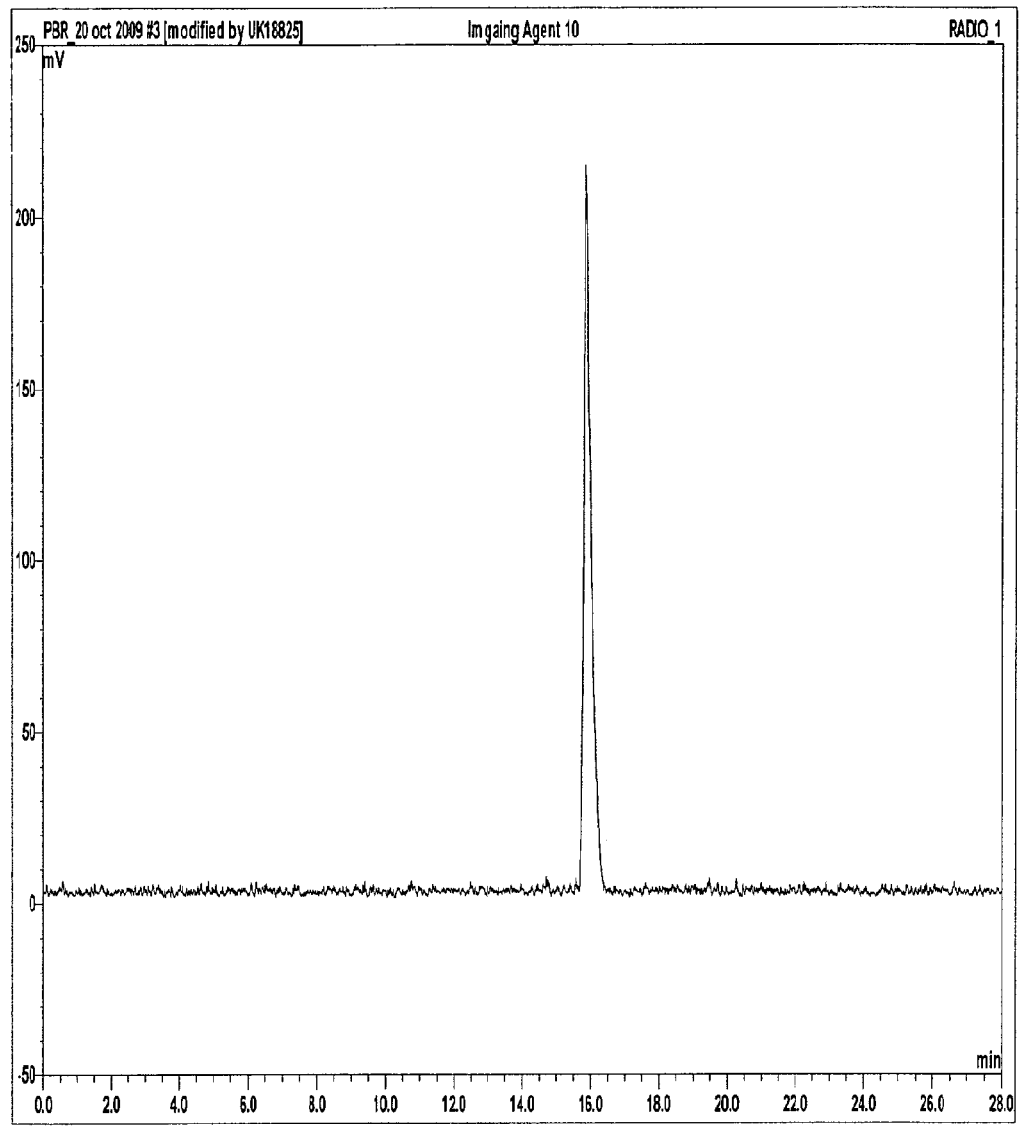
FIG. 5 shows imaging agent 10 (top) and 7-Fluoro-9-(2 [18F]fluoro-ethyl) -2,3,4,9-tetrahydro-1H-carbazole-4-carboxylic acid diethylamide (middle) and 7-Fluoro-9-(2-[19F]fluoro-ethyl)-2,3,4,9-tetrahydro-1H-carbazole-4-carboxylic acid diethylamide (bottom).
Figure 5:
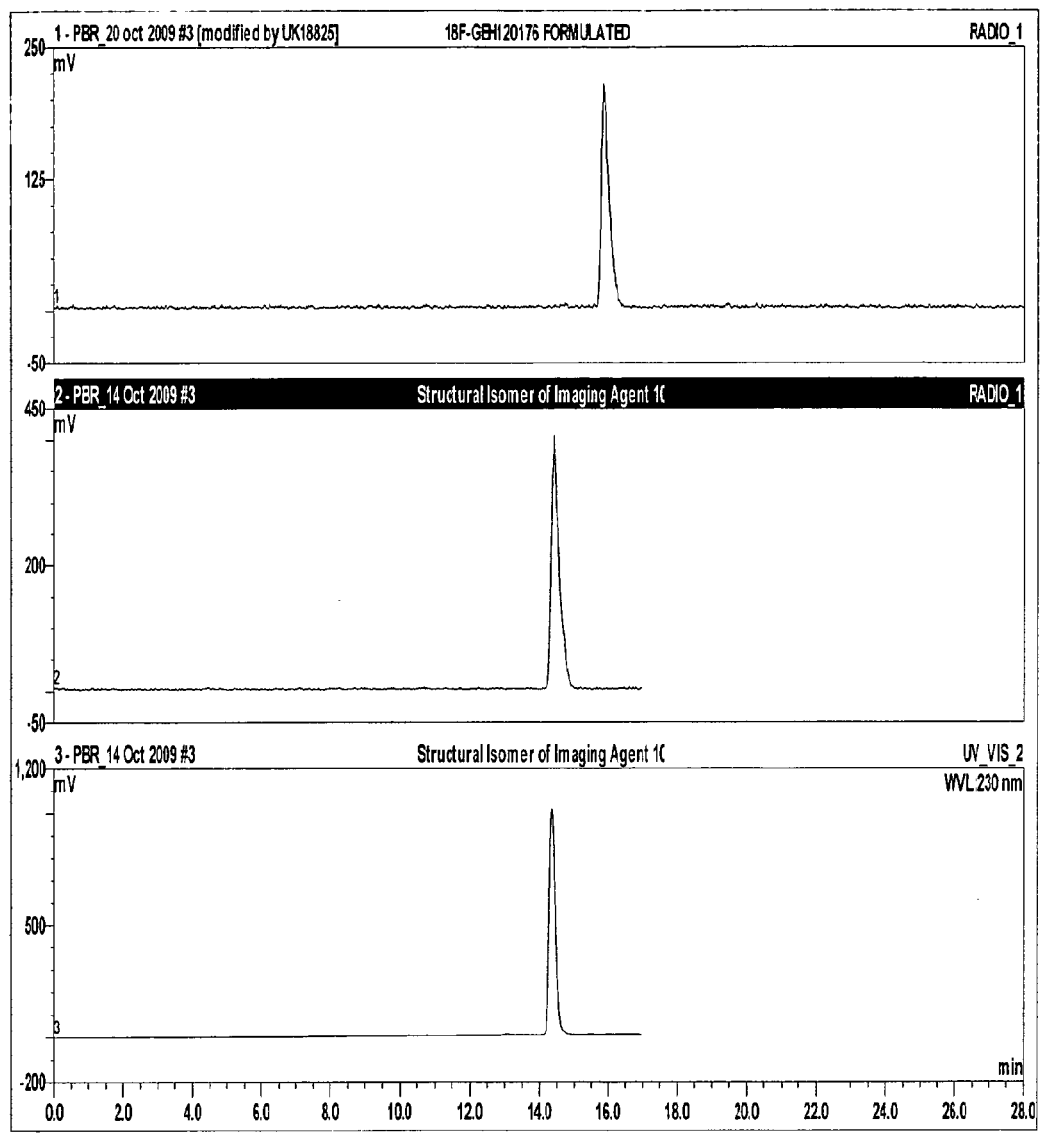

Analytical-HPLC: Phenomenex Luna C18 column (150× 4.6 mm i.d.), particle size 5 µm; mobile phase A: Water, mobile phase B: Methanol; flow gradient: 1 ml/min; 0-1 min 50% B; 1-20 mins 50-95% B; Wavelength 230 nm; $t_R$ imaging agent 10 16 mins; $t_R$ 7-Fluoro-9-(2-[$^{18}$F]fluoro-ethyl)-2,3,4,9-tetrahydro-1H-carbazole-4-carboxylic acid diethylamide 14 mins. Radiochemical yield of imaging agent 10 8.7±1% (n=3) non-decay corrected, time 90-120 mins, radiochemical purity ≥99%. FIG. 5 shows imaging agent 10 (top) and 7-Fluoro-9-(2-[$^{18}$F]fluoro-ethyl)-2,3,4,9-tetrahydro-1H-carbazole-4-carboxylic acid diethylamide (middle) and 7-Fluoro-9-(2-[$^{19}$F]fluoro-ethyl)-2,3,4,9-tetrahydro-1H-carbazole-4-carboxylic acid diethylamide (bottom).

Example 10

Synthesis of 5-Fluoro-9-(2-fluoro-ethyl)-2,3,4,9-tetrahydro-1H-carbazole-4-carboxylic acid diethylamide (Non-Radioactive Imaging Agent 10)

Example 10(a)

(2-fluoro-ethyl)-(3-fluoro-phenyl)-amine (43)

3-Fluoroaniline (1.4 g, 11.6 mmol, 1.2 mL) and 2-fluoro-ethyl tosylate (12; prepared according to Example 2(a)) (2.5 g, 11.6 mmol) and lutidine (1.24 g, 11.6 mmol) were stirred and heated in DMF (5 mL) at 100° C. overnight. The reaction was allowed to cool and then diluted with ethyl acetate (100 mL). This was washed with water (3×40 mL) and the organics were dried and concentrated in vacuo. The crude material was purified by silica gel chromatography eluting with petrol (A) and ethyl acetate (B) (10% B, 100 g, 12 CV, 60 mL/min) to afford 184 mg (10%) of (2-fluoro-ethyl)-(3-fluoro-phenyl)-amine (43) as a yellow oil. The structure was confirmed by $^1$H NMR (300 MHz, CDCl$_3$) $\delta_H$ 3.37 (1H, q, J=6 Hz, NCH$_2$CH$_2$F), 3.46 (1H, q, J=6 Hz, NCH$_2$CH$_2$F), 4.12 (1H, s, br, NH), 4.54 (1H, t, J=3 Hz, NCH$_2$CH$_2$F), 4.69 (1H, t, J=3 Hz, NCH$_2$CH$_2$F), 6.31-6.50 (3H, m, NCCHCHCH), 7.10-7.25 (1H, m, NCCHCF).

Example 10(b)

5-Fluoro-9-(2-fluoro-ethyl)-2,3,4,9-tetrahydro-1H-carbazole-4-carboxylic acid diethylamide (Non-Radioactive Imaging Agent 10)

A mixture of 3-bromo-2-oxo-cyclohexanecarboxylic acid diethylamide (35; prepared according to Example 7(c)) (161 mg, 0.6 mmol) and (2-fluoro-ethyl)-(3-fluoro-phenyl)-amine (43) (184 mg, 1.2 mmol) was stirred under N$_2$ at 50° C. for 3 h and the reaction turned brown. The resulting mixture was dissolved in propan-2-ol (1 mL) and dry zinc chloride (245 mg, 1.8 mmol) was added. The mixture was heated to reflux under N$_2$ for 16 h and then concentrated in vacuo. The residue was dissolved in ethyl acetate (10 mL) and washed with 2 N HCl (5 mL), water (2×5 mL) and aqueous potassium carbonate solution (2×5 mL) then dried and concentrated in vacuo. The crude material was purified by semi preparative HPLC eluting with water (A) and methanol (B) (Gemini 5 u, C18, 110A, 150×21 mm, 50-95% B over 20 min, 21 mL/min) to afford 20 mg (6%) of 7-fluoro-9-(2-fluoro-ethyl)-2,3,4,9-tetrahydro-1H-carbazole-4-carboxylic acid diethylamide as a white solid and 10 mg (3%) of 5-fluoro-9-(2-fluoro-ethyl)-2,3,4,9-tetrahydro-1H-carbazole-4-carboxylic acid diethylamide (non-radioactive imaging agent 10) as a white solid. The structure of 7-fluoro-9-(2-fluoro-ethyl)-2,3,4,9-tetrahydro-1H-carbazole-4-carboxylic acid diethylamide was confirmed by $^1$H NMR (300 MHz, CDCl$_3$) $\delta_H$ 1.14 (3H, t, J=7 Hz, N(CH$_2$CH$_3$)$_2$), 1.33 (3H, t, J=7 Hz, N(CH$_2$CH$_3$)$_2$), 1.80-2.15 (4H, m, 2- and 3-CH$_2$), 2.70-2.80 (2H, m, 1-CH$_2$), 3.50-3.80 (4H, m, N(CH$_2$CH$_3$)$_2$), 4.20-4.35 (1H, m, 4-CH), 4.40 (2H, dm, J=21 Hz, NCH$_2$CH$_2$F), 4.60 (2H, dm, J=41 Hz, NCH$_2$CH$_2$F), 6.70-6.80 (1H, m, NCCHCFCHCH), and 7.00-7.10 (2H, m, NCCHCFCHCH).

The structure of 5-fluoro-9-(2-fluoro-ethyl)-2,3,4,9-tetrahydro-1H-carbazole-4-carboxylic acid diethylamide (non-radioactive imaging agent 10) was confirmed by $^1$H NMR (300 MHz, CDCl$_3$) $\delta_H$ 1.14 (3H, t, J=7 Hz, N(CH$_2$CH$_3$)$_2$), 1.33 (3H, 4 J=7 Hz, N(CH$_2$CH$_3$)$_2$), 1.80-2.15 (4H, m, 2- and 3-CH$_2$), 2.70-2.80 (2H, m, 1-CH$_2$), 3.50-3.80 (4H, m, N(CH$_2$CH$_3$)$_2$), 4.20-4.35 (1H, m, 4-CH), 4.40 (2H, dm, J=21 Hz, NCH$_2$CH$_2$F), 4.60 (2H, dm, J=41 Hz, NCH$_2$CH$_2$F), 6.55-6.65 (1H, m, NCCHCHCHCF), 6.90-7.05 (1H, m, NCCHCHCHCF), and 7.05-7.15 (1H, m, NCCHCHCHCF).

Example 11

Methanesulfonic acid 2-(4-diethylcarbamoyl-2-methyl-1,2,3,4-tetrahydro-carbazol-9-yl)-ethyl ester (Precursor Compound 11) and 9-(2-[$^{18}$F]Fluoro-ethyl)-2-methyl-2,3,4,9-tetrahydro-1H-carbazole-4-carboxylic acid diethylamide (Imaging Agent 11)

Example 11(a)

4-(4-Methyl-cyclohex-1-enyl)-morpholine (44)

In a flask equipped with a dean stark, a solution of 4-methylcyclohexanone (20.1 g, 179.3 mmol, 22 mL) and morpholine (31.3 g, 359.0 mmol, 31.4 mL) were refluxed in benzene (55 mL) for 26 hours. The benzene was removed under vacuum and the crude product was purified by distillation under reduced pressure to afford 23 g (70%) of 4-(4-methyl-cyclohex-1-enyl)-morpholine (44) as an oil (b.p. 120° C. at 10 mmHg). The structure was confirmed by $^1$H NMR (300 MHz, CDCl$_3$): $\delta_H$ 0.94 (3H, d, J=6.0 Hz, CH$_3$), 1.15-1.35 (1H, m, CH$_2$CH=CN), 1.50-1.80 (3H, m, CH$_2$CH$_2$CHCH$_3$), 2.00-2.25 (4H, m, CH$_2$CH=CN and CH$_2$CH$_2$CHCH$_3$), 2.65-2.95 (4H, m, OCH$_2$NCH$_2$), 3.73 (4H, t, J=6.0 Hz, OCH$_2$NCH$_2$), and 4.60-4.65 (1H, m, CH$_2$CH=CN).

Example 11(b)

5-Methyl-2-oxo-cyclohexanecarboxylic acid ethyl ester (45)

To a solution of 4-(4-methyl-cyclohex-1-enyl)-morpholine (44) (23 g, 127.0 mmol) in benzene (55 mL), ethyl chloroformate (7.5 g, 69.0 mmol, 6.6 mL) was added under nitrogen while the enamine solution was being stirred rapidly. After refluxing for 18 h, the solution was cooled and filtered. The precipitate of enamine hydrochloride was washed with dry ether. The filtrate and washings were returned to the reaction flask and 10% aqueous HCl (40 mL) was added. The mixture was stirred vigorously for 15-30 min. The layers were separated, the aqueous layer was extracted with ethyl acetate (2×100 mL) and the combined organic layers were concen-

Example 11(c)

5-Methyl-2-oxo-cyclohexanecarboxylic acid diethylamide (46)

5-Methyl-2-oxo-cyclohexanecarboxylic acid ethyl ester (45) (5.9 g, 32 mmol), DMAP (1.12 g, 10 mmol) and diethylamine (4.7 g, 65 mmol, 6.7 mL) in toluene (90 mL) were heated at reflux for 4 days. The reaction was allowed to cool and the toluene was removed under reduced pressure to give a yellow oil. The crude material was purified by silica gel chromatography eluting with petrol (A) and ethyl acetate (B) (20-50% B, 80 g) to afford 4.4 g (65%) of 5-methyl-2-oxo-cyclohexanecarboxylic acid diethylamide (46) as a yellow oil. The structure was confirmed $^1$H NMR (300 MHz, CDCl$_3$) $\delta_H$ 0.8-1.05 (9H, m, C$\underline{H}_3$ and N(CH$_2$C$\underline{H}_3$)$_2$), 1.05-2.10 (5H, m, 5-C$\underline{H}$ and 4- and 6-C$\underline{H}_2$), 2.15-2.80 (2H, m, 3-C$\underline{H}_2$), 2.95-3.55 (5H, m, 1-C$\underline{H}$ and N(C$\underline{H}_2$CH$_3$)$_2$).

Example 11(d)

3-Bromo-2-hydroxy-5-methyl-cyclohex-1-enecarboxylic acid diethylamide (47)

5-methyl-2-oxo-cyclohexanecarboxylic acid diethylamide (46) (4.4 g, 21 mmol) was dissolved in diethyl ether (5 mL) and cooled to 0° C. under N$_2$. Bromine (3.32 g, 21 mmol, 1.1 mL) was added dropwise over 15 min and the reaction mixture was allowed to warm to room temperature over 90 min. The mixture was slowly poured into ice-cold saturated aqueous sodium carbonate solution (40 mL) and extracted with ethyl acetate (3×40 mL). The combined organic layers were dried and concentrated in vacuo to afford 6.1 g (quantitative) of 3-bromo-2-hydroxy-5-methyl-cyclohex-1-enecarboxylic acid diethylamide (47) as an off-white solid. The structure was confirmed by $^1$H NMR (300 MHz, CDCl$_3$) $\delta_H$ 0.8-1.20 (9H, m, C$\underline{H}_3$ and N(CH$_2$C$\underline{H}_3$)$_2$), 1.80-2.40 (5H, m, C$\underline{H}_2$C$\underline{H}$(CH$_3$)C$\underline{H}_2$), 3.15-3.55 (4H, m, N(C$\underline{H}_2$CH$_3$)$_2$), 4.65-4.74 (1H, m, C$\underline{H}$Br), and 12.04 (1H, s, O$\underline{H}$).

Example 11(e)

9-(2-Benzyloxy-ethyl)-2-methyl-2,3,4,9-tetrahydro-1H-carbazole-4-carboxylic acid diethylamide (48)

A mixture of 3-bromo-2-hydroxy-5-methyl-cyclohex-1-enecarboxylic acid diethylamide (47) (4.0 g, 14 mmol) and (2-benzyloxy-ethyl)-phenyl-amine (21; prepared according to Example 3(c)) (6.3 g, 28 mmol) was stirred under N$_2$ at 50° C. for 3 h and the reaction turned brown. The resulting mixture was dissolved in propan-2-ol (14 mL) and dry zinc chloride (5.72 g, 42 mmol) was added. The mixture was heated to reflux under N$_2$ for 16 h and then concentrated in vacuo. The residue was dissolved in ethyl acetate (200 mL) and washed with 2 N HCl (50 mL), water (2×50 mL) and aqueous potassium carbonate solution (2×50 mL) then dried and concentrated in vacuo. The crude mixture was purified by SCX cartridge (40 mL) and then silica gel chromatography eluting with petrol (A) and ethyl acetate (B) (10-50% B, 100 g, 12 CV, 85 mL/min) to afford 467 mg (8%) of 9-(2-Benzyloxy-ethyl)-2-methyl-2,3,4,9-tetrahydro-1H-carbazole-4-carboxylic acid diethylamide (48) as a white solid. The structure was confirmed by $^1$H NMR (300 MHz, CDCl$_3$) $\delta_H$ 1.20-1.40 (9H, m, CH$_3$ and N(CH$_2$CH$_3$)$_2$), 1.90-2.20 (3H, m, 2-CH and 3-CH$_2$), 2.35-2.45 (1H, m, 1-CH$_2$), 2.85-2.95 (1H, m, 1-CH$_2$), 3.40-3.70 (4H, m, N(CH$_2$CH$_3$)$_2$), 3.70-3.80 (1H, m, 4-CH), 4.10-4.30 (4H, m, NCH$_2$CH$_2$OBn), 4.43 (2H, s, OCH$_2$Ph), and 7.00-7.30 (9H, m, CHCHCHCH and Ph).

Example 11(f)

9-(2-Hydroxy-ethyl)-2-methyl-2,3,4,9-tetrahydro-1H-carbazole-4-carboxylic acid diethylamide (49)

To a solution of 9-(2-benzyloxy-ethyl)-2-methyl-2,3,4,9-tetrahydro-1H-carbazole-4-carboxylic acid diethylamide (48) (460 mg, 1.1 mmol) in methanol (25 mL) was added a slurry of Pd/C (100 mg) in methanol (5 mL). The mixture was placed on the Parr hydrogenator and shaken for 24 h under a hydrogen atmosphere. The reaction was filtered through a pad of celite, washed with methanol and concentrated in vacuo to afford 250 mg (79%) of 9-(2-hydroxy-ethyl)-2-methyl-2,3,4,9-tetrahydro-1H-carbazole-4-carboxylic acid diethylamide (49) as a yellow oil which was used in the next step without purification. The structure was confirmed by $^1$H NMR (300 MHz, CDCl$_3$) $\delta_H$ 1.20-1.40 (9H, m, C$\underline{H}_3$ and N(CH$_2$C$\underline{H}_3$)$_2$), 1.90-2.20 (3H, m, 2-C$\underline{H}$ and 3-C$\underline{H}_2$), 2.35-2.45 (1H, m, 1-C$\underline{H}_2$), 2.85-2.95 (1H, m, 1-C$\underline{H}_2$), 3.40-3.70 (4H, m, N(C$\underline{H}_2$CH$_3$)$_2$), 3.70-3.80 (1H, m, 4-C$\underline{H}$), 4.10-4.30 (4H, m, NC$\underline{H}_2$C$\underline{H}_2$OH), 6.91 (1H, t, J=7 Hz, NCCHCHC$\underline{H}$CH), 7.00 (1H, t, J=7 Hz, NCC$\underline{H}$CHCHCH), 7.12 (1H, d, J=7 Hz, NCCHCHCHC$\underline{H}$), and 7.15 (1H, d, J=7 Hz, NCC$\underline{H}$CHCHCH).

Example 11(g)

Methanesulfonic acid 2-(4-diethylcarbamoyl-2-methyl-1,2,3,4-tetrahydro-carbazol-9-yl)-ethyl ester (Precursor Compound II)

To a solution of 9-(2-hydroxy-ethyl)-2-methyl-2,3,4,9-tetrahydro-1H-carbazole-4-carboxylic acid diethylamide (49) (250 mg, 0.8 mmol) in dichloromethane (10 mL) was added pyridine (633 mg, 8.0 mmol, 0.6 mL). The reaction was cooled to 0° C. and methanesulfonyl chloride (367 mg, 3.2 mmol, 0.2 mL) was added. The reaction was allowed to warm to room temperature overnight. The mixture was washed with 2 N HCl (2×20 mL) and water (2×20 mL), dried and concentrated in vacuo. The crude material was purified by silica gel chromatography eluting with petrol (A) and ethyl acetate (B) (0-100% B, 10 g, 34 CV, 30 mL/min) then triturated with diethyl ether to afford 250 mg (80%) of methanesulfonic acid 2-(4-diethylcarbamoyl-2-methyl-1,2,3,4-tetrahydro-carbazol-9-yl)-ethyl ester (precursor compound II) as a white solid. The structure was confirmed by $^{13}$C NMR (75 MHz, CDCl$_3$) $\delta_C$ 12.9, 13.0, 15.2, 22.0, 29.7, 30.2, 36.7, 36.8, 40.8, 41.6, 42.0, 67.8, 108.6, 109.5, 118.6, 119.6, 121.2, 126.4, 136.2, 136.4, 173.7.

Example 11(h)

9-(2-[$^{18}$F]-Fluoro-ethyl)-2-methyl-2,3,4,9-tetrahydro-1H-carbazole-4-carboxylic acid diethylamide (Imaging Agent 11)

Labelling of precursor compound 11 with $^{18}$F was carried out as described in Example 1(f).

Semi-preparative HPLC: HICHROM ACE 5 C18 column (100×10 mm i.d.), particle size 5 μm; mobile phase A: Water, mobile phase B: Methanol; flow gradient: 3 ml/min; 0-26 min 50% B; Wavelength 254 nm; $t_R$ imaging agent 11 15 mins.

Figure 6:
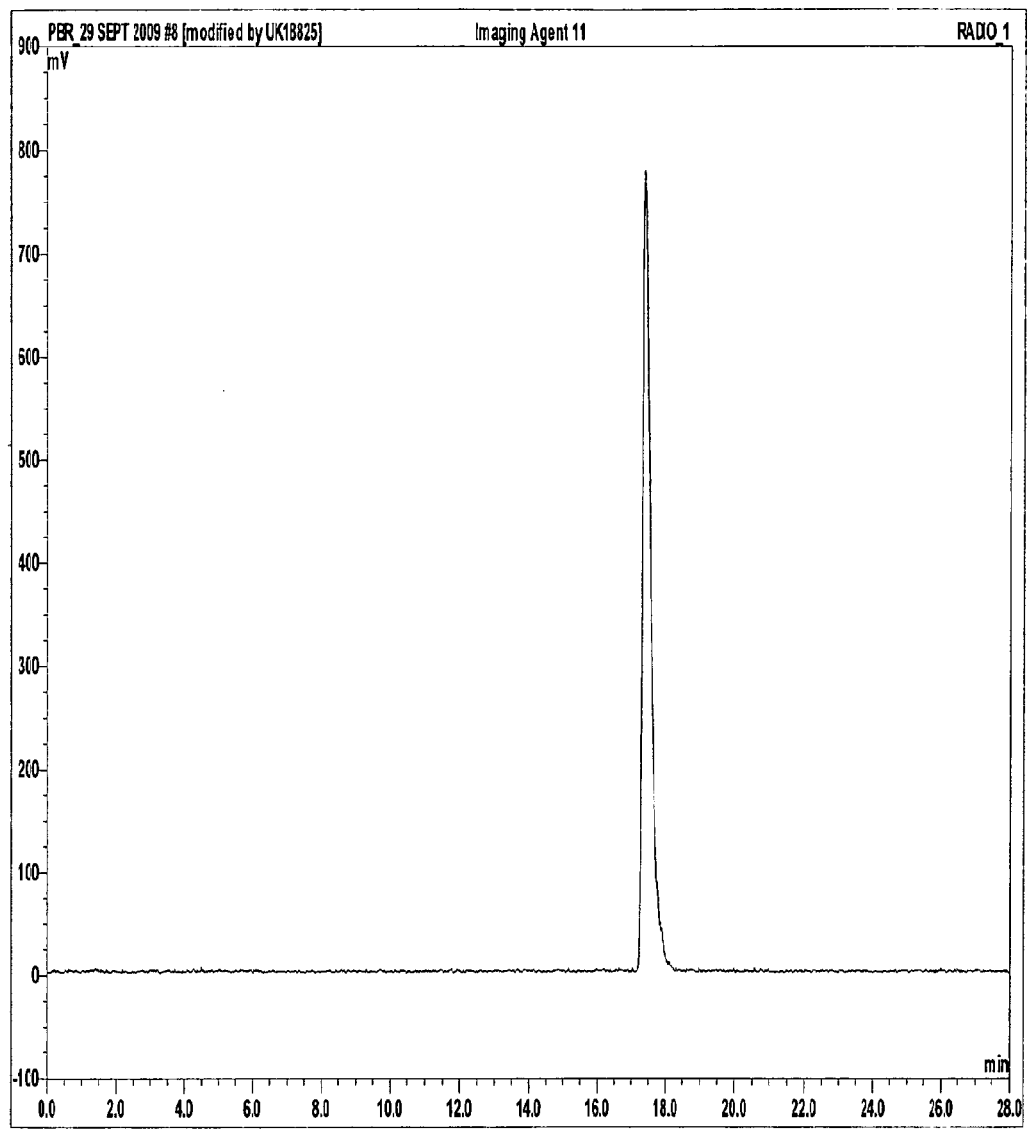
FIG. 6 shows co-elution of imaging agent lland non-radioactive imaging agent 11.
Figure 6:
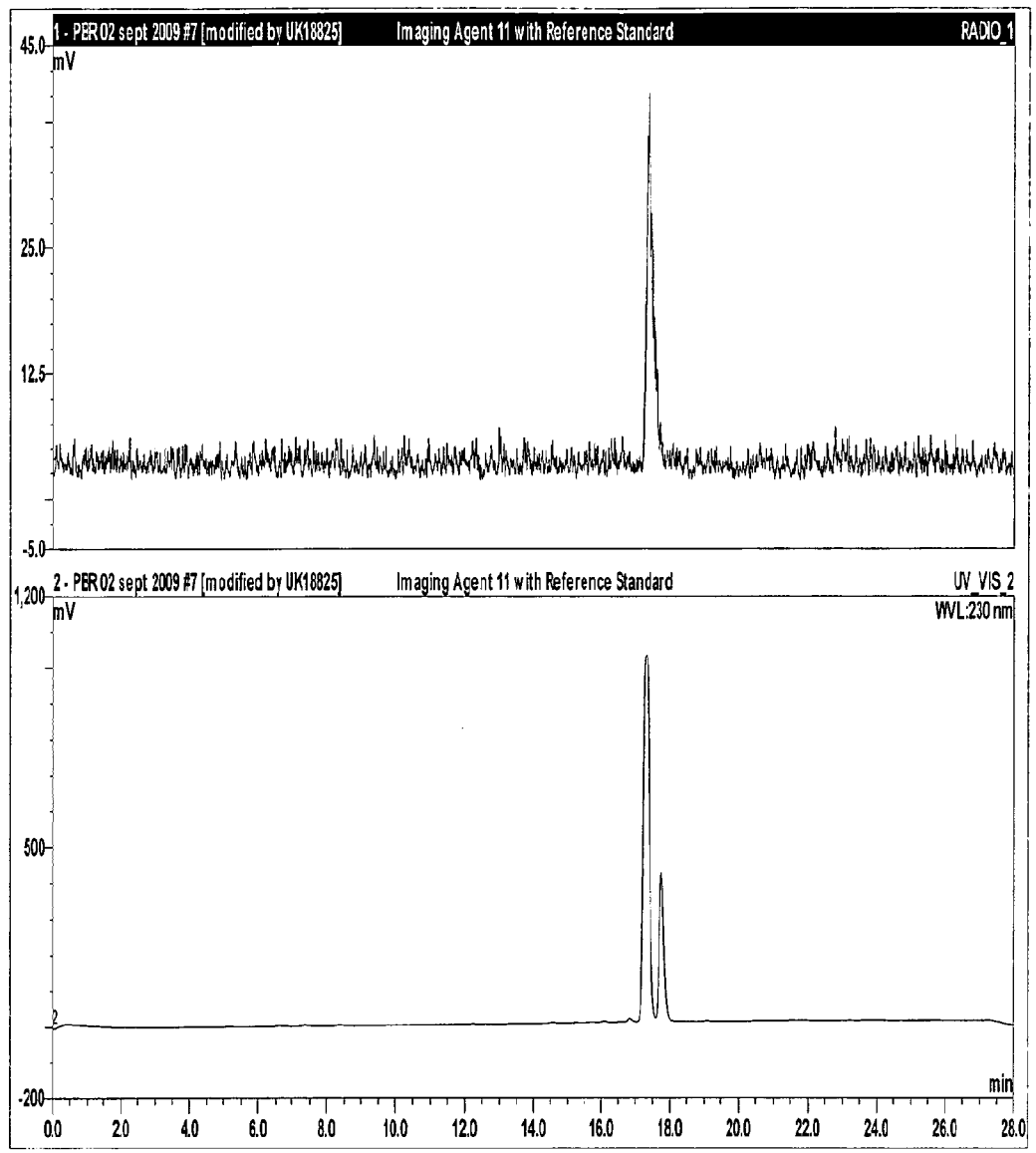

Analytical-HPLC: Phenomenex Luna C18 column (150× 4.6 mm i.d.), particle size 5 μm; mobile phase A: Water, mobile phase B: Methanol, flow gradient: 1 ml/min; 0-1 min 40% B; 1-20 mins 40-95% B; Wavelength 230 nm; $t_R$ imaging agent 11 17 mins. Radiochemical yield 14±13% (n=3) non-decay corrected, time 90-120 mins, radiochemical purity ≥99%. FIG. 6 shows co-elution of imaging agent 11and non-radioactive imaging agent 11.

Example 12

Synthesis of 9-(2-Fluoro-ethyl)-2-methyl-2,3,4,9-tetrahydro-1H-carbazole-4-carboxylic acid diethylamide (Non Radioactive Imaging Agent 11)

A mixture of 3-bromo-2-hydroxy-5-methyl-cyclohex-1-enecarboxylic acid diethylamide (47; prepared according to Example 11(d)) (2.0 g, 7 mmol) and (2-fluoro-ethyl)-phenylamine (24; prepared according to Example 4(a)) (1.9 g, 14 mmol) was stirred under $N_2$ at 50° C. for 3 h and the reaction turned brown. The resulting mixture was dissolved in propan-2-ol (7 mL) and dry zinc chloride (2.86 g, 21 mmol) was added. The mixture was heated to reflux under $N_2$ for 16 h and then concentrated in vacuo. The residue was dissolved in ethyl acetate (100 mL) and washed with 2 N HCl (30 mL), water (2×30 mL) and aqueous potassium carbonate solution (2×30 mL) then dried and concentrated in vacuo. The crude mixture was purified by SCX cartridge (40 mL) and then silica gel chromatography eluting with petrol (A) and ethyl acetate (B) (0-100% B, 100 g, 12 CV, 85 mL/min) to afford 400 mg (17%) of 9-(2-fluoro-ethyl)-2-methyl-2,3,4,9-tetrahydro-1H-carbazole-4-carboxylic acid diethylamide (non-radioactive imaging agent 11) as a white solid. The structure was confirmed by $^1$H NMR (300 MHz, CDCl$_3$) $\delta_H$ 1.10-1.35 (9H, m, C$\underline{H}_3$ and N(CH$_2$C$\underline{H}_3$)$_2$), 1.95-2.10 (2H, m, 3-C$\underline{H}_2$), 2.30-2.50 (1H, m, 2-C$\underline{H}$), 2.70-2.80 (2H, m, 1-C$\underline{H}_2$), 3.40-3.70 (4H, m, N(C$\underline{H}_2$CH$_3$)$_2$), 4.05-4.15 (1H, m, 4-C$\underline{H}$), 4.30 (2H, dm, J=21 Hz, NC$\underline{H}_2$CH$_2$F), 4.65 (2H, dm, J=41 Hz, NCH$_2$C$\underline{H}_2$F), and 7.00-7.30 (4H, m, NCC$\underline{H}$C$\underline{H}$C$\underline{H}$C$\underline{H}$.

Example 13

Enantiomeric Separation of Precursor Compound 5

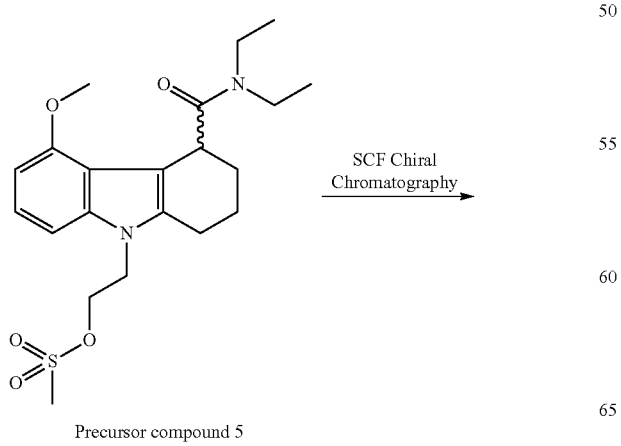

Precursor compound 5

SCF Chiral Chromatography →

-continued

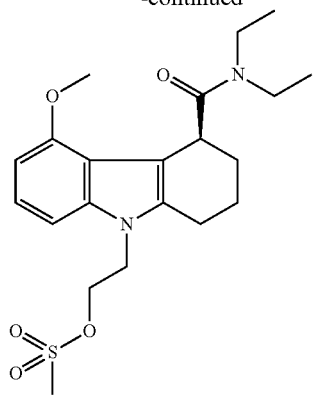

Enantiomer 1

+

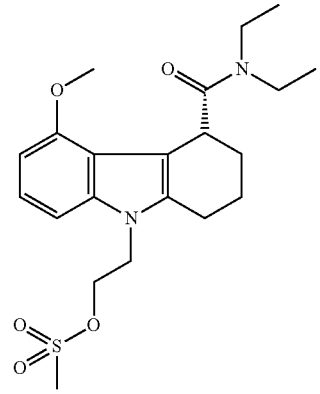

Enantiomer 2

Precursor compound 5 (obtained as described in Example 1) was separated into its enantiomers using chiral supercritical fluid (CO$_2$) chromatography on a Kromasil Amycoat, 250×10 mm, 5 μm, 100 Å column using 30% IPA at 40° C. at 13 ml a min with a run time of 6 min. Precursor compound 5 (60 mg) was dissolved in 1.4-Dioxane (2 ml) and up to 200 μl at a time was as injected for each run. Baseline separation between the two enantiomers was achieved. Analytical HPLC determination of the enantiomeric purity of the two separated enantiomers on an IC from Chiral Technologies, 250×4.6 mm, 5 μm, run isocratic, 80:20-MeOH: IPA at 0.5 ml/min and room temperature indicated an enantiomeric purity of 99.5% of each of the enantiomers.

Example 14

Enantiomeric Separation of Non-Radioactive Imaging Agent 5

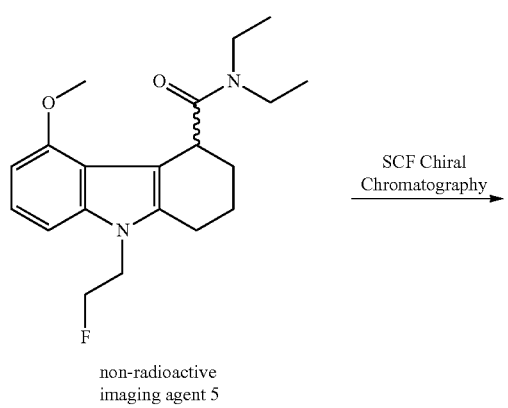

non-radioactive imaging agent 5

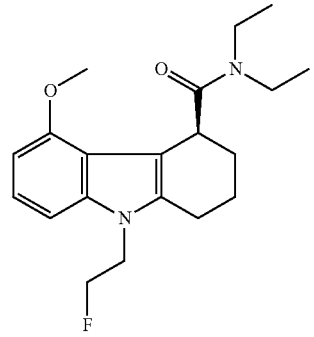

Enantiomer 1

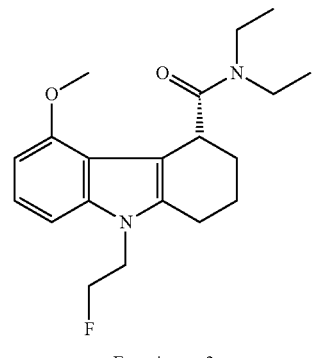

Enantiomer 2

Non-radioactive imaging agent 5 (obtained as described in Example 2) was separated into its enantiomers using chiral supercritical fluid ($CO_2$) chromatography on a Kromasil Amycoat, 250×10 mm, 5 μm, 100 Å column using 20% IPA at 40° C. at 14 ml a min with a run time of 6 min. Compound 5 (100 mg) was dissolved in 1.4-Dioxane (2.5 ml) and up to 200 μl at a time was as injected for each run. The fractions were cut by time to ensure that no mixed fractions were collected. Analytical HPLC determination of the enantiomeric purity of the two separated enantiomers on an IC from Chiral Technologies, 250×4.6 mm, 5 μm, run isocratic, 80:20-MeOH: IPA at 0.5 ml/min and room temperature indicated an enantiomeric purity of 99.5% of each of the enantiomers.

Example 15

In Vitro Potency Assay

Affinity for PBR was screened using a method adapted from Le Fur et al (Life Sci. 1983; USA 33: 449-57). Non-radioactive analogues of in vivo imaging agents of the invention were tested along with a non-radioactive analogue of a previous tetracyclic indole imaging agent (from co-pending patent application PCT/EP2009/062827; synthesis described in Example 17 below):

Each test compound (dissolved in 50 mM Tris-HCl, pH 7.4, 10 mM $MgCl_2$ containing 1% DMSO) competed for binding to Wistar rat heart PBR against 0.3 nM [$^3$H] PK-11195. The reaction was carried out in 50 mM Tris-HCl, pH 7.4 10 mM $MgCl_2$ for 15 minutes at 25° C. Each test compound was screened at 6 different concentrations over a 300-fold range of concentrations around the estimated $K_i$. The following data were observed:

| Imaging Agent | Ki (nM) |
|---|---|
| tetracyclic indole | 0.369 |
| Imaging agent 5 | 2.35 |
| Imaging agent 6 | 18.30 |
| Imaging agent 7 | 1.25 |
| Imaging agent 9 | 3.79 |
| Imaging agent 10 | 7.62 |
| Imaging agent 11 | 2.12 |

Example 16

In Vivo Biodistribution Method

Imaging agents of the invention were tested in an in vivo biodistribution model along with a previous tetracyclic imaging agent (from co-pending patent application PCT/EP2009/062827; synthesis described in Example 18 below).

Adult male Wistar rats (200-300 g) were injected with 1-3 MBq of test compound via the lateral tail vein. At 2, 10, 30 or 60 min (n=3) after injection, rats were euthanised and tissues or fluids were sampled for radioactive measurement on a gamma counter.

The following data of note were observed:

| Imaging Agent | Brain 2 min (% ID/g) | OB 30 min (% ID/g) | OB: Str 30 min | Str 2: 30 min | % Activity in Brain = Parent @ 60 min |
|---|---|---|---|---|---|
| tetracyclic indole | 0.32 | 0.31 | 2.07 | 1.73 | 96.00 |
| 5 | 0.52 | 0.36 | 3.00 | 3.67 | 90.18 |
| 6 | 0.51 | 0.25 | 2.50 | 4.70 | 83.08 |
| 7 | 0.55 | 0.34 | 3.40 | 4.70 | 81.28 |
| 9 | 0.56 | 0.41 | 3.72 | 4.27 | 84.30 |
| 10 | 0.50 | 0.51 | 3.19 | 2.56 | 92.70 |
| 11 | 0.51 | 0.42 | 3.50 | 3.33 | 90.37 |

% ID/g: percentage of injected dose per gram;
OB: olfactory bulb;
Str: striatum

FIGS. 7-13 illustrate the biodistribution profile in the brain of the tetracyclic imaging agent and imaging agents 5-7 and 9-11, respectively. It can be seen that the in vivo imaging agents of the present invention have good brain uptake and improved specific uptake in PBR-expressing tissues in comparison to the tetracyclic imaging agent.

Example 17

Preparation of (+−)-11-(2-fluoroethyl)-8-methoxy-6,11-dihydro-5-thia-11-aza-benzo[a]fluorene-6-carboxylic acid diethyl amide (Non-Radioactive Tetracyclic Indole Imaging Agent)

17(a)

(+−)-4-Oxo-thiochroman-2-carboxylic acid diethyl amide (50)

(+−)-4-Oxo-thiochroman-2-carboxylic acid (10.4 g, 50 mmol), prepared as described in T. Okubo et at (Bioorg. Med. Chem. 2004; 12: 3569-3580), in dry DCM (100 ml) was stirred under an atmosphere of nitrogen at room temperature with oxalyl chloride (12.6 g, 100 mmole) and one drop of DMF for 18 h. The reaction was then evaporated in vacuo to a gum and then redissolved in DCM (100 ml), cooled to 0° C. on an ice bath, stirred and treated dropwise with diethylamine (8.03 g, 110 mmol) in DCM (20 ml) over a period of 1 h. The reaction was allowed to warm to room temperature over 1 h and 10% aqueous potassium carbonate solution (100 ml) was added and the reaction mixture vigorously stirred. The DCM solution was separated. The aqueous solution was extracted with two further batches of DCM (100 ml) and the combined extracts were dried over magnesium sulphate. The DCM solution was concentrated in vacuo to give a dark green oil that crystallized on standing. The crystalline solid was triturated with diethyl ether (50 ml) and filtered to give the title compound (50) (8.57 g, 65%) as a pale green solid. The structure was confirmed by $^1$H NMR (300 MHz, CDCl$_3$) δ 1.06 (t, J=7.1 Hz, 3H), 1.23 (t, J=7.1 Hz, 3H), 3.0-3.5 (m, 6H), 4.25 (m, 1H), 7.15-7.21 (m, 2H), 7.32-7.39 (m, 1H), 8.10-8.14 (m, 1H).

17(b)

(+−)-8-methoxy-6,11-dihydro-5-thia-11-aza-benzo[a]fluorene-6-carboxylic acid diethyl amide (51)

To a solution of (+−)-4-Oxo-thiochroman-2-carboxylic acid diethyl amide (50) (1.32 g, 5.0 mmol) and 4-methoxyphenyl hydrazine hydrochloride (0.87 g, 5.0 mmol) in ethanol (10 ml) was added concentrated sulphuric acid (0.73 ml, 1.35 g, 13.8 mmol) under nitrogen. The reaction mixture was heated under reflux for 24 h. After cooling, the reaction mixture was filtered, the solid washed with ethanol, dried in vacuo (45° C.) to give the title compound (51) (1.05 g, 57%) as a pale yellow solid. The structure was confirmed by $^{13}$C NMR (75 MHz, DMSO-d$_6$) δ 10.5, 12.7, 32.7, 37.9, 39.5, 53.0, 97.6, 103.3, 109.87, 109.92, 120.3, 123.5, 123.8, 124.3, 124.7, 124.9, 127.8, 129.4, 131.8, 151.3, 166.2.

17(c)

(+−)-11-(2-fluoroethyl)-8-methoxy-6,11-dihydro-5-thia-11-aza-benzo[a]fluorene-6-carboxylic acid diethyl amide (Non-Radioactive Analogue of Previous Tetracyclic Indole Imaging Agent)

To a solution of (+−)-8-methoxy-6,11-dihydro-5-thia-11-aza-benzo[a]fluorene-6-carboxylic acid diethyl amide (51) (150 mg, 0.41 mmol; prepared according to Example 17(b)) in anhydrous DMF (4 ml) was added 2-fluoroethyl tosylate (166 mg, 0.82 mmol), prepared as described in L. Cronin et al (J. Org. Chem. 2004; 69: 5934-5946) followed by sodium hydride 60% dispersion in mineral oil (34 mg, 0.82 mmol) under nitrogen. The reaction mixture was heated at 80° C. for 1 h. After cooling, the solvents were removed in vacuo, the residue quenched with water (30 ml), extracted with DCM (2×30 ml), dried (MgSO$_4$) and solvents removed in vacuo. The residue was purified by column chromatography on silica, eluting with 5-10% EtOAc/CH$_2$Cl$_2$. The crude solid was quenched with ether/pet.spirit, filtered, dried in vacuo (45° C.) to give the title compound (non-radioactive tetracyclic indole imaging agent) (77 mg, 46%) as a pale brown solid. The structure was confirmed by $^1$H NMR (300 MHz, CDCl$_3$) δ 1.12 (t, J=7.0 Hz, 3H), 1.36 (t, J=7.0 Hz, 3H), 3.25-3.70 (m, 4H), 3.83 (s, 3H), 4.45-4.70 (m, 2H), 4.80 (t, J=5.2 Hz, 1H), 4.96 (t, J=5.2 Hz, 1H), 5.09 (s, 1H), 6.84-6.93 (m, 2H), 7.13-7.32 (m, 3H), 7.46 (m, 1H), 7.58 (d, J=8.0 Hz, 1H).

Example 18

Synthesis of (+−)-11-(2-[18F]fluoroethyl)-8-methoxy-6,11-dihydro-5-thia-11-aza-benzo[a]fluorene-6-carboxylic acid diethyl amide (Tetracyclic Indole Imaging Agent)

$^{18}$F$^-$/water was added to K222 (4 mg), aqueous K$_2$CO$_3$ (50 μl of a 0.1 molar solution) and acetonitrile (50 μl) in a reaction vessel and dried for 20-30 mins at 100° C. under a stream of nitrogen. Ethyl-1,2-ditosylate (4 mg) in acetonitrile (1000 ul) was added and heated at 100° C. for 10 mins. The reaction mixture was cooled and purified by semi preperative HPLC and the fraction containing $^{18}$F-fluoroethyl tosylate was collected. This fraction was diluted to a volume of ca. 20 ml with H$_2$O, loaded onto a conditioned light t-C18 sep pak, and flushed with H$_2$O (1×2 ml). The sep pak was dried on the N$_2$ line with high flow, for 20 mins. The $^{18}$F fluoroethyl tosylate was then eluted with DMF (500 μl).

Precursor compound (+−)-8-methoxy-6,11-dihydro-5-thia-11-aza-benzo[a]fluorene-6-carboxylic acid diethyl amide (51; prepared according to Example 17(b)) (13 mg) in DMF (250 ul) was added to a second reaction vessel, and purged with N$_2$, for 5 mins. NaH (1.3 mg) in DMF (2×250 ul) was then added under nitrogen and the reaction vessel was heated at 45° C. for 0.5-1 h. To this was then added the $^{18}$F fluoroethyl tosylate in DMF prepared above and heated at 100° C. for 10 mins in the N$_2$ purged reaction vessel. The reaction was cooled and washed from the reaction vessel with water (1 ml). The solution was filtered through a syringe filter and purified on a preparative HPLC. The fraction containing the main radioactive peak was collected. This was diluted to a volume of ca. 10 ml with H$_2$O, and loaded onto a conditioned light C18 sep pak, flushed with H$_2$O (1×2 ml), and eluted with EtOH (0.5 ml) into a P6 vial and Phosphate Buffered Saline (5 ml) added.

What is claimed is:

1. An in vivo imaging agent of Formula I:

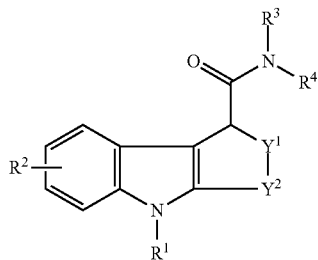

wherein:
- $R^1$ is $C_{1-3}$ alkyl or $C_{1-3}$ fluoroalkyl;
- $R^2$ is hydrogen, hydroxyl, halo, cyano, $C_{1-3}$ alkyl, $C_{1-3}$ alkoxy, $C_{1-3}$ fluoroalkyl, or $C_{1-3}$ fluoroalkoxy;
- $R^3$ and $R^4$ are independently $C_{1-3}$ alkyl, $C_{7-10}$ aralkyl, or $R^3$ and $R^4$, together with the nitrogen to which they are attached, form a nitrogen-containing $C_{4-6}$ aliphatic ring optionally comprising 1 further heteroatom selected from nitrogen, oxygen and sulfur;
- $Y^1$ is $CH_2$; and,
- $Y^2$ is $CH_2$, $CH_2$—$CH_2$, $CH(CH_3)$—$CH_2$ or $CH_2$—$CH_2$—$CH_2$;

and wherein the agent of Formula I comprises an atom which is a radioisotope suitable for in vivo imaging.

2. The in vivo imaging agent as defined in claim 1 wherein said radioisotope suitable for in vivo imaging is selected from $^{11}C$, $^{18}F$ and $^{123}I$.

3. The in vivo imaging agent as defined in claim 1 wherein $R^1$ is methyl or $C_{2-3}$ fluoroalkyl.

4. The in vivo imaging agent as defined in claim 1 wherein $R^2$ is hydrogen, halo, $C_{1-3}$ alkoxy or $C_{1-3}$ fluoroalkoxy.

5. The in vivo imaging agent as defined in claim 1 wherein $R^3$ and $R^4$ are independently methyl, ethyl or benzyl.

6. The in vivo imaging agent as defined in claim 1 wherein $R^3$ and $R^4$, together with the nitrogen to which they are attached, form a nitrogen-containing $C_{5-6}$ aliphatic ring.

7. The in vivo imaging agent as defined in claim 1 wherein $Y^2$ is $CH_2$—$CH_2$.

8. The in vivo imaging agent as defined in claim 1 which is of Formula Ia:

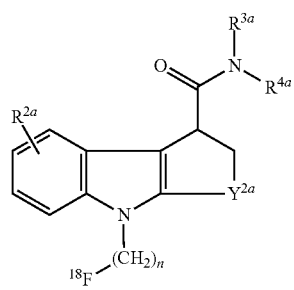

wherein:
- $R^{2a}$ is hydrogen, halo or $C_{1-3}$ alkoxy;
- $R^{3a}$ and $R^{4a}$ are independently methyl, ethyl or benzyl, or together with the nitrogen to which they are attached form a pyrrolidinyl, piperidinyl, azepanyl, or morpholinyl ring;

$Y^{2a}$ is $CH_2$, $CH_2$—$CH_2$, $CH(CH_3)$—$CH_2$, or $CH_2$—$CH_2$—$CH_2$; and;
n is 1, 2 or 3.

9. The in vivo imaging agent as defined in claim 8 wherein:
- $R^{3a}$ and $R^{4a}$ are both ethyl, or $R^{3a}$ is methyl and $R^{4a}$ is benzyl, or together with the nitrogen to which they are attached form an azepanyl ring;
- $R^{2a}$ is hydrogen, methoxy or fluoro;
- $Y^{2a}$ is $CH_2$—$CH_2$ or $CH(CH_3)$—$CH_2$; and,
- n is 2.

10. The in vivo imaging agent as defined in claim 9 which is of the following chemical structure:

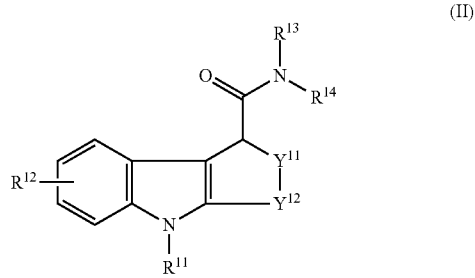

11. A method for the preparation of the in vivo imaging agent as defined in claim 1 comprising:
(i) providing a precursor compound of Formula II:

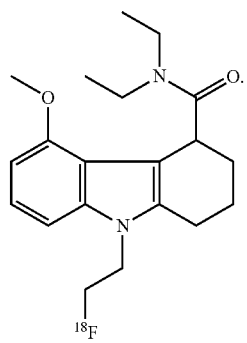 [SMILES: CCN(CC)C(=O)C1CCCc2c1c1c(OC)cccc1n2CC[18F]]

wherein if $R^{11}$ comprises a chemical group that reacts with a suitable source of a radioisotope suitable for in vivo imaging, then $R^{12}$ is hydrogen, hydroxyl, halo, cyano, $C_{1-3}$ alkyl, $C_{1-3}$ alkoxy, $C_{1-3}$ fluoroalkyl, or $C_{1-3}$ fluoroalkoxy, and optionally comprises a protecting group;

if $R^{12}$ comprises a chemical group that reacts with a suitable source of a radioisotope suitable for in vivo imaging, then $R^{11}$ is $C_{1-3}$ alkyl or $C_{1-3}$ fluoroalkyl, and optionally comprises a protecting group;

$R^{13}$ and $R^{14}$ are independently $C_{1-3}$ alkyl, $C_{7-10}$ aralkyl, or $R^{13}$ and $R^{14}$, together with the nitrogen to which they are attached, form a nitrogen-containing $C_{4-6}$ aliphatic ring optionally comprising 1 further heteroatom selected from nitrogen, oxygen and sulphur, and $R^{13}$ and $R^{14}$ optionally comprises a protecting group;

$Y^{11}$ is $CH_2$ and, $Y^{12}$ is $CH_2$, $CH_2$—$CH_2$, $CH(CH_3)$—$CH_2$ or $CH_2$—$CH_2$—$CH_2$, and optionally comprises a protecting group;

(ii) providing a suitable source of a radioisotope suitable for in vivo imaging;

(iii) reacting the precursor compound of step (i) with the radioisotope of step (ii) to obtain said in vivo imaging agent.

12. The method as defined in claim 11 which is automated.

13. A radiopharmaceutical composition comprising the in vivo imaging agent as defined in claim 1 together with a biocompatible carrier in a form suitable for mammalian administration.

14. An in vivo imaging method for determining the distribution and/or the extent of PBR expression in a subject comprising:
   (i) administering to said subject an in vivo imaging agent as defined in claim 1;
   (ii) allowing said in vivo imaging agent to bind to PBR in said subject;
   (iii) detecting by an in vivo imaging procedure signals emitted by the radioisotope of said in vivo imaging agent;
   (iv) generating an image representative of the location and/or amount of said signals; and,
   (v) determining the distribution and extent of PBR expression in said subject wherein said expression is directly correlated with said signals emitted by said in vivo imaging agent.

15. The in vivo imaging method as defined in claim 14 which is carried out repeatedly during the course of a treatment regimen for said subject, said regimen comprising administration of a drug to combat a PBR condition.

16. A method for diagnosis of a condition in which PBR is upregulated comprising the method of in vivo imaging as defined in claim 14, together with a further step (vi) of attributing the distribution and extent of PBR expression to a particular clinical picture.

* * * * *